United States Patent [19]

Bernstein et al.

[11] Patent Number: 5,254,558
[45] Date of Patent: Oct. 19, 1993

[54] SUBSTITUTED 1,3-DIAZINES AS LEUKOCYTE ELASTASE INHIBITORS

[75] Inventors: Peter R. Bernstein, Wallingford, Pa.; Philip D. Edwards, Claymont, Del.; Royston M. Thomas, Wilmington, Del.; Chris A. Veale, Newark, Del.; Peter Warner, Macclesfield, England; Donald J. Wolanin, Wilmington, Del.

[73] Assignee: Imperial Chemical Industries PLC, Millbank, England

[21] Appl. No.: 930,568

[22] Filed: Aug. 14, 1992

[30] Foreign Application Priority Data

Aug. 15, 1991 [GB] United Kingdom ................. 9117641
Apr. 16, 1992 [GB] United Kingdom ................. 9208378
Jul. 8, 1992 [GB] United Kingdom ................. 9214447

[51] Int. Cl.$^5$ .................... A61K 31/505; C07D 239/22
[52] U.S. Cl. ..................................... 514/269; 544/123; 544/243; 544/296; 544/319
[58] Field of Search ............... 544/123, 295, 296, 319, 544/243; 514/269

[56] References Cited

U.S. PATENT DOCUMENTS 4,910,190 3/1990 Bergeson et al. ................... 546/225

Primary Examiner—Mukund J. Shah
Assistant Examiner—Y. N. Gupta
Attorney, Agent, or Firm—Thomas E. Jackson

[57] ABSTRACT

The present invention relates to certain novel substituted heterocycles which are 1-pyrimidinylacetamide compounds of formula I, set out herein, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes intermediates useful in the synthesis of these substituted heterocycles, processes for preparing the substituted heterocycles, pharmaceutical compositions containing such substituted heterocycles and methods for their use.

16 Claims, No Drawings

SUBSTITUTED 1,3-DIAZINES AS LEUKOCYTE ELASTASE INHIBITORS

The present invention relates to certain substituted heterocycles, in particular, certain 1-pyrimidinylacetamide compounds, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. For example, HLE has been implicated in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as chronic bronchitis and cystic fibrosis. Also, HLE has been implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also includes intermediates useful in the synthesis of these heterocyclic amides, processes for preparing the heterocyclic amides, pharmaceutical compositions containing such heterocyclic amides and methods for their use.

In U.S. Pat. No. 4,910,190, of Mar. 20, 1990, assigned to ICI Americas Inc., there is disclosed a series of peptidoyl trifluoromethane derivatives which are HLE inhibitors. Disclosed herein is a series of substituted 2-(6-oxo-1,6-dihydro-1-pyrimidinyl)-N-[3,3,3-trifluoro-1-(lower alkyl)-2-oxopropyl]acetamide derivatives, which unexpectedly possess inhibitory properties against HLE, which provides the basis for the present invention.

According to the invention there is provided a Compound of the invention which is a compound of formula I (formula set out, together with other formulae referred to by Roman numerals, following the Examples) wherein:

$R^0$ is (1–5C)alkyl;

R is hydrogen; or

R is an acyl group of formula A.X.CO— in which A.X—, taken together, is hydrogen, trifluoromethyl, 2,2,2-trifluoroethoxy, amino, methoxyamino, 2,2,2-trifluoroethylamino, RbRcN.O—, RaOCONH—, $R^1SO_2NH$—, RaOCO—, RbRcNCO— or RaCO—; or R is an acyl group of formula A.X.CJ— in which J is oxygen or sulfur;

X is a direct bond, imino, oxy or thio; and

A is as defined below or

A is tetrahydropyran-4-yl, 1-methylpiperid-4-yl, or 5-methyl-1,3-dioxacyclohex-5-ylmethyl; or R is a sulfonyl group of formula $D.W.SO_2$— in which D.W—, taken together, is hydroxy, amino, di(-lower alkyl)amino, 2,2,2-trifluoroethylamino, 2,2,2-trifluoroethyl, 3,3,3-trifluoropropyl or trifluoromethyl; or W is a direct bond, imino, carbonylimino, oxycarbonylimino or iminocarbonylimino; and D is as defined below; or R is an alkyl, aryl or heteroaryl group G as defined below;

The group A, D or G is (1–6C)alkyl, (3–6C)cycloalkyl, (3–6C)cycloalkyl-(1–3C)alkyl, aryl, aryl(1–3C)alkyl, heteroaryl or heteroaryl(1–3C)alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, CONRbRc, $COO(CH_2)_2NReRf$, cyano, $SO_2R^1$, $CONRdSO_2R^1$, NReRf, NRgCHO, $NRgCOR^2$, $NRgCOOR^2$, NRhCQNRiRj, $NRkSO_2R^3$, $SO_2NRlRm$, $SO_2NRnCOR^4$ and $P(O)(ORa)_2$ in which Q is oxygen or sulfur;

Ra-Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^1$–$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl;

$R^6$ is (1–5C)alkyl which has no tertiary carbon, (3–7C)cycloalkyl, aryl or heteroaryl, which aryl or heteroaryl independently may bear one or more of the substituents defined for the group A or an aryl or heteroaryl moiety thereof; and provided that no aliphatic carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

In this specification, the following definitions are used, unless otherwise described: Halogeno is fluoro, chloro, bromo or iodo. Alkyl, alkoxy, etc. denote both straight and branched groups; but reference to an individual radical such "propyl" embraces only the straight chain ("normal") radical, a branched chain isomer such as "isopropyl" being specifically referred to. Lower alkyl and lower alkoxy refer to radicals containing one to about four carbon atoms. Lower acyloxy refers to a radical containing one to about five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof.

It will be appreciated that, owing to the asymmetrically substituted carbon atom at the chiral center indicated by "*" in formula I, a compound of formula I may exist in, and be isolated in, optically active and racemic forms. If a compound of formula I contains an additional chiral element, such compound of formula I may exist in, and be isolated in, the form of a diastereomeric mixture or as a single diastereomer. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. When $R^0$ is isopropyl, a compound of formula I may be viewed as an alanyl trifluoromethane derivative. In general, a compound of formula I having the (S)-configuration at the chiral center indicated by "*", which corresponds to the L-alanyl configuration, is preferred. Accordingly, it may be preferred to use the compound of formula I in a form which is characterized as containing, for example, at least 95%, 98% or 99% enantiomeric excess (ee) of the (S)-form. However, owing to the interconvertability of the (S)-isomer and the (R)-isomer by the facile epimerization of the chiral center indicated by "*" in formula I, it may be preferred to utilize a compound of formula I as a mixture of the (S)- and (R)-isomers at the center indicated by "*" in formula I.

As will be appreciated by those skilled in the art, a trifluoromethyl ketone of formula I can exist as a solvate, particularly a hydrate; and such a solvate of a compound of formula I is encompassed by the present invention.

A compound of formula I may exhibit polymorphism. The compound may form solvates in addition to a ketone solvate mentioned above. A compound may exist in more than one tautomeric form. It is to be understood, therefore, that the present invention encompasses any racemic or optically-active form, any polymorphic form, any tautomer or any solvate, or any mixture thereof, which form possesses inhibitory properties against HLE, it being well known in the art how to prepare optically active forms (for example, by resolution of the racemic form or by synthesis from optically-active starting materials) and how to determine the inhibitory properties against HLE by the standard tests described hereinafter.

It is preferred that the radicals $R^0$, R and $R^6$ not contain nor introduce an additional element of chirality into the molecule beyond the chiral center indicated by "*" in formula I.

Particular values are listed below for radicals, substituents and ranges for illustration only and they do not exclude other defined values or other values within defined ranges for the radicals and substituents.

A particular value for $R^0$ is methyl, ethyl, propyl, isopropyl or isobutyl.

A particular value for W is a direct bond or imino.

A particular value for G is (1-3C)alkyl, aryl(1-C)alkyl or heteroaryl(1-2C)alkyl which may bear one or more substituents as defined above for G or a part thereof.

A particular value of (1-6C)alkyl is methyl, ethyl, propyl, isopropyl, butyl, isobutyl, t-butyl, pentyl, 3-methylbutyl, 1-ethylpropyl, hexyl or 4-methylpentyl. A particular value of (3-6C)cycloalkyl is cyclopropyl, cyclopentyl or cyclohexyl. A particular value for the (1-3C)alkyl portion of (3-6C)cycloalkyl(1-3C)alkyl, aryl(1-3C)alkyl or heteroaryl(1-3C)alkyl is methylene, ethylene or trimethylene. A particular value for aryl is phenyl, indenyl or naphthyl. A particular value for heteroaryl is furyl, imidazolyl, tetrazolyl, pyridyl (or its N-oxide), thienyl, pyrimidinyl (or its N-oxide), indolyl or quinolinyl (or its N-oxide). A particular value for lower alkyl is methyl, ethyl, propyl, isopropyl, butyl, isobutyl or t-butyl. A particular value for lower acyloxy is acetoxy. A particular value for lower alkoxy is methoxy, ethoxy, propoxy, isoproxy or t-butoxy. A particular value for halogeno is bromo, chloro or fluoro.

A particular value for A.X—, taken together, is 2,2,2-trifluoroethoxy. A particular value for COORa is carboxy or methoxycarbonyl. A particular value for CONRbRc is carbamoyl or N,N-dimethylcarbamoyl. A particular value for $NRgCOR^2$ is trifluoroacetylamino. A particular value of $CONRdSO_2R^1$ is N-phenylsulfonylcarbamoyl or N-(4-chlorophenylsulfonyl)carbamoyl. A particular value for A.X— is tris(hydroxymethyl)methylamino, tris(acetoxymethyl)methylamino or 2,2-bis(hydroxymethyl)propoxy.

A particular value for D.W—, taken together, is 2,2,2-trifluoroethylamino or 3,3,3-trifluoropropyl.

A particular value for $R^6$ is, for example, isopropyl, cyclopentyl, cyclohexyl, phenyl, furyl, thienyl or pyridyl in which a phenyl or heteroaryl may bear one or two substituents as defined above.

A more particular value for $R^0$ is isopropyl. A more particular value for A.X—, taken together, is 2,2,2-trifluoroethoxy. A more particular value for J is oxygen. A more particular value for X is a direct bond, imino or oxy. A more particular value for A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for D.W-, taken together, is 2,2,2-trifluoroethylamino or 3,3,3-trifluoropropyl. A more particular value for D is methyl, ethyl, isopropyl, tert-butyl, cyclohexyl, phenyl, benzyl, phenethyl, pyridyl, thienyl, 5-tetrazolyl, thiazolyl, quinolinyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonylamino, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for G is methyl, ethyl, benzyl, phenethyl, pyridyl, pyridylmethyl, thenyl, 5-tetrazolylmethyl, or 2-(pyridyl)ethyl, wherein an alkyl carbon may bear an oxo group and wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

A particular value for R is, for example, hydrogen, formyl, trifluoroacetyl, 2,2,2-trifluoroethoxycarbonyl, hydroxyoxalyl, methoxycarbonyl, ethoxycarbonyl, isopropoxycarbonyl, 2-methoxyethoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxy-carbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, methylthiocarbonyl, sulfo, aminosulfonyl, dimethylaminosulfonyl, 2,2,2-trifluoroethylaminosulfonyl, 3,3,3-trifluoroethylsulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, formylamino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolinylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

A more particular value for R is, for example, hydrogen, formyl, trifluoroacetyl, 2,2,2-trifluoroethoxycarbonyl, methoxycarbonyl, ethoxycarbonyl, isopropoxycarbonyl, 2-methoxyethoxycarbonyl, 4-bromophenoxycarbonyl, benzyloxycarbonyl, 2,6-dimethylpyrid-4-ylmethoxy-carbonyl, methylthiocarbonyl, tert-butylaminosulfonyl, 4-acetylaminophenylsulfonyl, 4-{N-(4-chlorophenylsulfonyl)carbamoyl}phenylsulfonyl, benzylsulfonyl, benzylaminosulfonyl or ethyl.

A particular group of compounds of formula I is one in which $R^0$ and R have any of the values defined above and $R^6$ is 2-furyl, 2-thienyl, 3-pyridyl or phenyl in which the phenyl may bear one or two halogeno, trifluoromethyl, methyl, hydroxy, methoxy, tert-butoxy methoxycarbonyl or carboxy substituents; and, more particularly, $R^6$ is phenyl, 4-fluorophenyl or 2-thienyl.

A more particular group of compounds of formila I is one in which $R^0$ is isopropyl, R is hydrogen, formyl, 2,2,2-trifluoroethoxycarbonyl, isopropoxycarbonyl, methylthiocarbonyl or ethyl, and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents; and, more particularly, $R^6$ is phenyl, 4-fluorophenyl or 2-thienyl.

Specific compounds of formula I are described in the accompanying Examples. Of these, compounds of particular interest, along with their pharmaceutically acceptable salts, include those described in Examples 12, 15, 51, 82, 99, 100, 102, 106, 157 and 159, based upon their activity in in vivo tests.

A pharmaceutically acceptable salt of an acidic compound of formula I is one made with a base which affords a pharmaceutically acceptable cation, which incldes alkalai metal salts (especially calcium and magnesium), aluminum salts and ammonium salts, as well as salts made from appropriate organic bases such as triethylamine, morpholine, piperidine and triethanol amine. A pharmaceutically acceptable salt of a basic compound of formula I includes an acid-addition salt made with an acid which provides a pharmaceutically acceptable anion, including for example, a strong acid such as hydrochloric, sulfuric or phosphoric acid.

A compound of formula I may be made by processes which include processes known in the chemical art for the production of structurally analogous heterocyclic and peptidic compounds. Such processes and intermediates for the manufacture of a compound of formula I as defined above are provided as further features of the invention and are illustrated by the following procedures in which the meanings of generic radicals are as defined above:

(A) Oxidizing a corresponding alcohol of formula II. If R is hydrogen or a group G, it will be recognized that protection of the pyridone 3-amino substituent prior to oxidation and removal of the protecting group after oxidation may be preferred or required if the amino group is not stable to the oxidation conditions employed. A convenient method is the use of excess dimethyl sulfoxide and a water soluble carbodimide, with dichloroacetic acid as a catalyst, in a inert solvent such as toluene at about room temperature, for example as described in Example 1. Other methods which may be useful include the use of alkaline aqueous potassium permanganate solution; the use of oxalyl chloride, dimethyl sulfoxide and a tertiary amine; the use of acetic anhydride and dimethyl sulfoxide; the use of chromium trioxide pyridine complex in methylene chloride; and the use of a hypervalent iodine reagent, such as a periodinane, for example 1,1,1-triacetoxy-2,1-benzoxidol-3(3H)-one with trifluoroacetic acid in dichloromethane.

(B) For a compound of formula I which contains an N—H residue, removal by using a conventional method of the nitrogen protecting group of a corresponding compound bearing a conventional nitrogen protecting group to afford the compound of formula I which contains an amino N—H residue, particularly for a compound of formula I in which R is hydrogen, removal of a group from a corresponding compound of formula I, or for a compound of formula I in which R has a value of G, the removal of an activating/protecting group Rx from a corresponding compound of formula Vb. Rx is a group which protects and activates a primary amino group for substitution, such as for example benzyloxycarbonyl or trifluoroacetyl. Conventional methods include, for example, removal of a benzyloxycarbonyl group by hydrogenolysis, as described in Example 6; removal of a benzyloxycarbonyl by treatment with a strong acid, as described in Example 12, for example with trifluoromethanesulfonic acid in an inert solvent such as dichloromethane; and basic hydrolysis of a trifluoroacetyl group.

(C) For a compound of formula I wherein R is an acyl group, acylation of a corresponding amine of formula I wherein R is hydrogen. Convenient methods include those described below for acylation of an amine of formula XIII, for example, when J is oxygen, the use of an activated carboxylic acid derivative, such as an acid halide, the use of a carboxylic acid and a coupling reagent, the use of an isocyanate for a compound wherein X is imino, and the use of a diactivated carbonic acid derivative, for example, carbonyldiimidazole, phosgene, diphosgene (trichloromethyl chloroformate) or triphosgene (bis(trichloromethyl) carbonate) with an alcohol of formula A.OH, a thiol of formula A.SH or an amine of formula $A.NH_2$ and a base, such as triethylamine or, when J is sulfur, the use of an activated thiocarboxylic acid derivative, such as a thioyl chloride or a lower alkyl ester of a dithioic acid, the use of a thioic acid and a coupling reagent, the use of an isothiocyanate for a compound wherein X is imino, and the use of a diactivated thiocarbonic acid derivative, for example, dimethyl trithiocarbonate, with an alcohol of formula for example, dimethyl trithiocarbonate, with an alcohol of formula A.OH, a thiol of formula A.SH or an amine of formula $A.NH_2$. In addition, for a compound of formula I in which R is an acyl group of formula A.X.CO— and X is oxy or imino, the acylation may be carried out by converting the corresponding amine of formula I in which R is hydrogen into its corresponding isocyanate, followed by reaction of the isocyanate with an alcohol of formula A.OH or an amine of formula $A.NH_2$, respectively, using a method similar to that described for Example 7. For an acylation using an isocyanate, for example for a compound of formula I wherein X is amino and J is oxygen, using a catalyst, for example, cuprous chloride, as described in Example 113, may be preferred.

(D) For a compound of formula I wherein R is a sulfonyl group, sulfonylation of a corresponding amine of formula I wherein R is hydrogen with a corresponding sulfonic acid of formula $D.W.SO_2.OH$, or an activated derivative thereof, such as an acid halide, particularly a sulfonyl (or sulfamoyl) chloride of formula $D.W.SO_2.Cl$. The sulfonylation is conveniently carried out in an inert solvent or diluent, such as dichloromethane, tetrahydrofuran or toluene, at about ambient temperature, using an organic base such as, for example, triethylamine or pyridine, or an inorganic base, such as sodium or potassium carbonate, as an acid acceptor. If a sulfonyl chloride is not commercially available, it may be obtained by a conventional method.

(E) For a compound of formula I in which R is a group G, substitution of the group L of a corresponding compound of formula G-L, wherein L is a conventional leaving group, such as for example halogeno, methylsulfonyloxy, trifluoromethylsulfonyloxy or diazonium, with a corresponding amine of formula I wherein R is hydrogen, optionally using a conventional catalyst.

(F) For a compound of formula I which bears a hydroxy substituent on an aryl or heteroaryl group, cleaving the alkyl ether or acyloxy ester of a corresponding compound of formula I which bears a lower alkoxy or lower acyloxy substituent on an aryl or heteroaryl group. Convenient methods include, for example, the cleavage of a methoxy group using boron tribromide or pyridinium chloride and the cleavage of a t-butoxy group using trifluoroacetic acid for an alkyl ether, and the acidic or alkaline hydrolysis of an acyloxy group.

(G) For a compound of formula I which bears a group of formula COORa in which Ra is hydrogen (a carboxy group), decomposing the ester group of a corresponding ester made with a conveniently removed acid protecting group, for example a corresponding compound of formula I in which Ra is not hydrogen. The decomposition may be carried out using any one of the variety of procedures well known in organic chemistry, for example basic hydrolysis using lithium or sodium hydroxide, or by hydrogenolysis of a benzyl ester.

(H) For a compound of formula I bearing a moiety of formula COORa, CONRbRc, $COO(CH_2)_2NReRf$ or $CONRdSO_2R^1$, acylation of a corresponding compound of formula HORa, HNRbRc, $HO(CH_2)_2NReRf$ or $HNRdSO_2R^1$ with a corresponding acid of formula I bearing a moiety of formula COORa in which Ra is hydrogen, or an activated derivative thereof.

(I) For a compound of formula I bearing a lower acyloxy group or a group of formula NRgCHO, $NRgCOR^2$, $NRgCOOR^2$, NRhCQNRiRj or $NRkSO_2R^3$, acylation or sulfonylation of a corresponding compound of formula I bearing a hydroxy group or an amino group of formula NHRg, NHRh or NHRk (i.e. an amino group of formula NReRf is which Re is hydrogen and Rf is Rg, Rh or Rk) with an activated derivative of a corresponding acid of formula HOCHO, $HOCOR^2$, $HOCOOR^2$, HOCQNRiRj (including an isocyanate or isothiocyanate) or $HOSO_2R^3$, respectively, using a conventional method.

(J) For a compound of formula I which bears a heteroaryl N-oxide group, oxidation of a corresponding compound of formula I which bears a heteroaryl group using a conventional oxidant, such as for example with peracetic acid or with dioxirane in acetone.

(K) For a compound of formula I which bears a primary amino group, reduction of a corresponding compound bearing a nitro group using a conventional reducing method, such as for example, hydrogenation over a palladium catalyst, or reduction with tin(II) chloride or with iron in acetic acid.

Whereafter, for any of the above procedures, when a pharmaceutically acceptable salt of an acidic or basic compound of formula I is required, it may be obtained by reacting the acidic or basic form of such a compound of formula I with a base or acid affording a physiologically acceptable counterion or by any other conventional procedure.

If not commercially available, the necessary starting materials for the above procedures may be made by procedures which are selected from standard techniques of heterocyclic chemistry andpeptide chemistry, techniques which are analogous to the synthesis of known, structurally similar compounds, and techniques which are analogous to the above described procedures or the procedures described in the Examples. For uniformity and clarity, compounds herein are represented as the 6-pyrimidone, rather than the 6-hydroxypyrimidine, tautomers.

As will be clear to one skilled in the art, a variety of sequences is available for preparation of the starting materials. According to one of the available routes, a key intermediate pyrimidin-6-one-1-acetic acid of formula III may be prepared as shown in Scheme I (set out, together with other Schemes, following Examples) and as described in the Examples. In the Schemes, CBZ represents a benzyloxycarbonyl group.

In general, a nitrile of formula $R^6CN$ is converted into a corresponding imidic ester of formula IV wherein $R^7$ is methyl or ethyl, conveniently isolated as its hydrochloride, if the imidic ester is not commercially available. Reaction of the imidic ester with an amine of formula H₂NCH₂R⁸ in which $R^8$ is a latent or protected carboxaldehyde group, such as vinyl, dimethoxymethyl or diethoxymethyl, affords a corresponding amidine of formula V, conveniently isolated as its hydrochloride salt. Cyclization of an amidine of formula V with diethyl ethoxymethylenemalonate affords a corresponding ethyl 1,2-disubstitied-6-pyrimidone-5-carboxylate of formula VI which is hydrolyzed to the 1,2-disubstituted-6-pyrimidone-5-carboxylic acid of formula VII.

An acid of formula VII may be converted into a corresponding isocyanate of formula VIII by a conventional method, for example by using diphenylphosphoryl azide in an inert solvent, as described in the examples. Conveniently, the isocyanate is not isolated, but is converted into a benzyl urethane of formula IX as also is shown in Scheme I. It will be clear to one skilled in the art that, in general, treatment of an isocyanate of formula VIII with a selected alcohol or amine of formula A.X.H in which X is oxy or imino will provide a corresponding product of formula IXa in which X is oxy or imino, and that the product of formula IXa may be carried forward to a corresponding product of formula I using one of the routes outlined below.

Transformation of $R^8$ into a carboxaldehyde to afford a corresponding compound of formula X from a compound of formula IX is the next step. If $R^8$ is a vinyl group, the transformation may be carried out using N-methylmorpholine-N-oxide and osmium tetroxide, as described in Example 1, part e. If $R^8$ is a dimethoxymethyl or diethoxyethyl group, the acetal may be hydrolyzed with dilute hydrochloric acid, as described in Example 8, part f. Oxidation of an acetaldehyde derivative of formula X to provide a corresponding substituted acetic acid of formula III is conveniently carried out as described in Example if using sodium chlorite as the oxidant.

Elaboration of an acetic acid derivative of formula III into a corresponding intermediate alcohol of formula II or amine of formula Vb may be carried out as outlined in Scheme II. Thus, coupling a substituted acetic acid of formula III with an amino alcohol of formula XI, using, for example the method described in Example 1, part g, affords a corresponding alcohol of formula II in which R is benzyloxycarbonyl. Oxidation using a procedure as described above in process (A) provides a corresponding ketone of formula I in which R is benzyloxycarbonyl. As described above in process (B), by removing the benzyloxycarbonyl group, for example by hydrogenolysis as described in Example 6, an aminoketone of formula I in which R is hydrogen is obtained. Alternatively, an alcohol of formula II in which R is benzyloxycarbonyl may be converted into a corresponding compound of formula XII in which Rp represents an alcohol protecting group, conveniently tert-butyldimethylsilyl, for example as described in Example 2, part a. Removal of the benzyloxycarbonyl group of a compound of formula XII by a conventional method, for example as noted in process (B) above, affords a corresponding 5-amino pyrimidone derivative of formula XIII.

A 3-amino pyridone of formula XIII may then be acylated, sulfonylated or be substituted with a group G by using a conventional method to afford a corresponding pyridone of formula XIV. Conventional acylation and sulfonylation methods and methods for introducing a group R include those described above in processes (C), (D) and (E) for substituting an amine of formula I wherein R is hydrogen. (Should a portion of bis-sulfonylated product be obtained, treatment with aqueous base at an elevated temperature may be used to remove the more labile second sulfonyl group at a convenient stage in the synthesis.) Removal of a tert-butyldimethylsilyl group to provide a corresponding alcohol of formula II may be carried out using tetrabutylammonium fluoride in an inert solvent, for example as described in Example 2, part d; it may be preferred to use acetic acid to buffer the reaction conditions.

Alternatively, for preparation of an intermediate of formula Vb, oxidation of an alcohol of formula II wherein R is benzyloxycarbonyl, using a method similar to one described in process (A), affords a corresponding ketone of formula I wherein R is benzyloxycarbonyl. Removal of the nitrogen protecting group of a ketone of formula I wherein R is benxyloxycarbonyl by hydrogenolysis or by treatment with a strong acid affords a corresponding amine of formula I wherein R is hydrogen. A preferred method for introducing the substituent R when it is a group G, particularly when it is an alkyl or substituted alkyl group, is by the use of a corresponding compound in which the pyrimidone 5-amino substituent bears an activating/protecting group of formula Rx, for example, benzyloxycarbonyl or trifluoroacetyl. Thus, acylation of a compound of formula I wherein R is hydrogen with trifluoroacetic anhydride affords a corresponding compound of formula Va in which Rx is trifluoroacetyl, which compound also may be prepared by an alternative order of steps via the corresponding compound of formula XIII. It will be noted that each of a compound of formula Va in which Rx is benzyloxycarbonyl or trifluoroacetyl is also a compound of formula I in which R is an acyl group. Alkylation, using a corresponding reagent of formula G.L in which G is alkyl or substituted alkyl, then provides a corresponding intermediate of formula Vb.

The trifluoromethyl amino alcohols of Formula XI required for the synthesis routes described above may be prepared by known routes. For example, 3-amino-1,1,1-trifluoro-4-methyl-2-pentanol (as its hydrochloride salt) conveniently may be obtained as described in U.S. Pat. No. 4,910,190 in Example 4 (as a single diastereomer) or Example 6 (as a single enantiomer of a single diastereomer). If it is desired to carry out a chiral synthesis of a compound of formula I, using the single enantiomer in a substantially enantiomerically pure form and using methods and conditions which avoid epimerization at the center indicated by "*" in formula I provide such a synthesis.

It may be desired optionally to use a protecting group during all or portions of the above described processes; the protecting group then may be removed when the final compound or a required starting material is to be formed. As will be clear to one skilled in the art, the order of steps in the sequences leading to the starting materials and products of the invention may be altered if appropriate considerations relative to coupling methods, racemization, deprotection methods, etc. are followed.

The utility of a compound of the invention or a pharmaceutically acceptable salt thereof (hereinafter, collectively referred to as a "Compound") may be demonstrated by standard tests and clinical studies, including those described below.

INHIBITION MEASUREMENTS

The potency of a Compound to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of an inhibitor is evaluated by obtaining a kinetic determination of the dissociation constant, $K_i$, of the complex formed from the interaction of the inhibitor with HLE. If a Compound is found to be a "slow-binding" inhibitor of HLE, special methods of analysis to accurately determine $K_i$ values for the inhibition of HLE are carried out as described in U.S. Pat. No. 4,910,190. In general, the $K_i$ values for Compounds of the invention which were tested are generally on the order of $10^{-7}$M or much less. For example, a $K_i$ of 27 nM was determined for the Compound of the invention described as Example 51.

ACUTE LUNG INJURY MODEL

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 μg), or by dosing them intravenously or orally as solutions at various times prior to the HLE challenge (100 μg) to determine their utility in preventing an HLE lesion. A solution of a Compound is conveniently prepared using 10% polyethylene glycol 400/PBS or 10% polyethylene glycol 400/water. For a Compound which is acidic or basic, base (e.g. sodium hydroxide solution) or acid (e.g. hydrochloric acid) may be added as indicated to achieve solution. Compounds of this invention produced statistically significant reductions in wet lung weight and total lavagable cells relative to HLE alone.

ACUTE HEMORRHAGIC ASSAY

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et al., *American Review of Respiratory Disease* (1990), 141, 672–677, is as follows.

Compounds demonstrated to be HNE inhibitors in vitro are conveniently prepared for dosing as described above for the Acute Lung Injury Model. The compounds are then dosed by mouth to male Syrian hamsters at a fixed time, such as 30 or 90 min, prior to intratracheal administration of 50 μg/animal of HNE in 300 μL phosphate buffered saline (PBS) pH 7.4. Four hours enzyme administration, the animals are killed with an overdose of pentobarbital sodium, the thorax opened and the lungs and trachea removed. The excised lungs are lavaged with three changes of 2 mL normal saline via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 405 nm. The (μL blood equivalents)/(mL lavage) are determined by comparing the OD of the test samples with the OD of the standard curve prepared from whole hamster blood. The total μL equivalents of blood recovered is determined by multiplying recovered lavage volume by the (μL blood equivalents)/(mL lavage) for each sample. Results are reported as % inhibition of hemorrhage with respect to PBS treated controls when the test compound is given at a specified dose and time prior to administration of HNE. For example, the Compound of the invention described as Example 51 provided statistically significant inhibition of hemorrhage when administered at a dose of 2.5 mg/kg 30 or 90 min prior to administration of HNE.

No overt toxicity was observed when Compounds of the invention were administered in the above in vivo tests.

It will be appreciated that the implications of a Compound's activity in the Acute Lung Injury Model or Acute Hemorrhagic Assay are not limited to emphysema, but, rather, that the test provides evidence of general in vivo inhibition of HLE.

Compounds of the present invention which were tested exhibited activity in at least one of the tests described above under Inhibition Measurement, Acute Lung Injury Model and Acute Hemorrhagic Assay. It should be noted that there was not always a direct correlation between the activities of the compounds measured as $K_i$ values in the Inhibition Measurement test and the reduced values for total lavagable cells and wet lung weights relative to the administration of HLE alone obtained in the Acute Lung Injury Model test or inhibition of hemorrhage in the Acute Hemorragic Assay.

According to a further feature of the invention, there is provided a pharmaceutical composition comprising a pharmaceutically effective amount of a Compound and a pharmaceutically acceptable diluent or carrier. As noted above, another feature of the invention is a method of using a Compound of the invention in the treatment of a disease or condition in a mammal, especially a human, in which HLE is implicated.

A Compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. The preferred mode of administration may be via a powdered or liquid aerosol. In a powdered aerosol, a Compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a Compound of the invention with the remainder of the 20 mg capsule being a pharmaceutically acceptable carrier such as lactose. In aliquid aerosol, a Compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of a Compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of administration may be oral or parenteral, including subcutaneous deposit by means of an osmotic pump. A compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 mL intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

For parenteral administration or use in an aerosol, a 10 mg/mL aqueous formulation of an acidic Compound may be prepared, for example by dissolving the Compound (10 mg), dibasic sodium phosphate heptahydrate, USP (11.97 mg), monobasic sodium phosphate, USP (0.74 mg), sodium chloride, USP (4.50 mg) and sufficient 1N sodium hydroxide solution or 0.05M monobasic sodium phosphate solution to achieve pH 7.0–7.5 in sufficient water for injection, USP to afford 1.0 mL (1.01 g), followed by aseptic filtration, and sterile storage using standard procedures.

In general, a Compound of the invention will be administered to humans at a daily dose in the range of, for example, 5 to 100 mg of the Compound by aerosol or 50 to 1000 mg intravenously, or a combination of the two. However, it readily will be understood that it may be necessary to vary the dose of the Compound administered in accordance with well known medical practice to take account of the nature and severity of the disease under treatment, concurrent therapy, and the age, weight and sex of the patient receiving treatment. It similarly will be understood that generally equivalent amounts of a pharmaceutically acceptable salt of the Compound also may be used. Protocols for the administration of the HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and a Compound of the invention may be used similarly for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a Compound of the invention may conveniently be administered by a parenteral route, either alone or simultaneously or sequentially with other therapeutically active agents customarily administered for the condition.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous sodium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany); if "acidic silica gel" is indicated, material custom prepared by J. T. Baker Chemical Co., Phillipsburg, N. J., USA, and having a pH of about 6 when slurried in water was used; reversed phase chromatography means flash chromatography over octadecylsilane (ODS) coated support having a particle diameter of 32–74 $\mu$, know as "PREP-40-ODS" (Art 731740-100 from Bodman Chemicals, Aston, Pa., USA); thin layer chromatography (TLC) was carried out on 0.25 mm silica gel GHLF plates (Art 21521 from Analtech, Newark, Del., USA); reversed phase-TLC (RP-TLC) was carried out Whatman MKC$_{18}$F plates (Art 4803-110 from Bodman Chemicals);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 250 MHz using DMSO-d$_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported.

EXAMPLE 1

2-(5-Benzyloxycarbonylamino-6-oxo-2-phenyl-1,6-dihydro-1-pyrimidinyl)-N-(3,3,3-trifluoro-1-isopropyl-2-oxopropyl)acetamide To a solution of 2-(5-benzyloxycarbonylamino-6-oxo-2-phenyl-1,6-dihydro-1-pyrimidinyl)-N-(3,3,3-trifluoro-2-hydroxy-1-isopropylpropyl)acetamide (0.537 g), 1-(3-dimethylaminopropyl)-3-ethylcarbodiimide (1.9 g) in toluene (4 mL) and dimethyl sulfoxide (4 mL) was added dichloroacetic acid (0.33 mL) and the resulting solution was allowed to stir for 0.5 h. The reaction mixture was diluted with ethyl acetate, washed (saturated ammonium chloride, water), dried and evaporated to provide a white solid which was collected and washed with ether:hexane (1:1) to give 2-(5-benzyloxycarbonylamino-6-oxo-2-phenyl-1,6-dihydro-1-pyrimidinyl)-N-(3,3,3-trifluoro-1-isopropyl-2-oxopropyl)acetamide (0.330 g). Chromatography of the mother liquor with ethyl acetate:dichloromethane (5:95, 10:90) as the eluent gave additional 2-(5-benzyloxycarbonylamino-6-oxo-2-phenyl-1,6-dihydro-1-pyrimidinyl)-N-(3,3,3-trifluoro-1-isopropyl-2-oxopropyl)acetamide as a white solid (0.190 g); NMR (DMSO/D$_2$O): 8.46 (s,1), 7.44 (m,10), 5.20 (s,2), 4.54 (m,2), 4.05 (d,1), 2.23 (m,1), 0.85 (d,3), 0.75 (d,3); MS: m/z=531(M+1).

Analysis for C$_{26}$H$_{25}$F$_3$N$_4$O$_5$: Calculated: C, 58.8; H, 4.74; N, 10.5 Found: C, 58.4; H, 4.75; N, 10.6

The intermediate 2-(5-benzyloxycarbonylamino-6-oxo-2-phenyl-1,6-dihydro-1-pyrimidinyl)-N-(3,3,3-trifluoro-2-hydroxy-1-isopropylpropyl)acetamide was prepared as follows:

a. N-Allyl benzamidine hydrochloride

To a solution of ethyl benzimidate hydrochloride (20 g) in methanol at 0° C. was added allyl amine. The resulting solution was allowed to stand for 2 days at 5° C. before it was evaporated to yield a solid which was collected and washed with ether to give N-allyl benzamidine hydrochloride (21.5 g) as a white solid; 300 MHz NMR: 10.1 (s,1), 9.68 (s,1), 9.29 (s,1), 7.72 (s,5), 5.92 (m,1), 5.35 (d,2), 5.26 (d,2), 4.14 (s,2).

b. Ethyl 1-allyl-2-phenylpyrimidin-6(1H)-one-5-carboxylate

The free base of N-allyl benzamidine hydrochloride was generated by dissolving N-allyl benzamidine hydrochloride (79.7 g) in 1N sodium hydroxide. The free base was then extracted into dichloromethane, which was dried and evaporated to provide N-allyl benzamidine (65.2 g). This was added to diethyl ethoxymethylene malonate (78 mL) in ethanol (50 mL). The resulting solution was heated at 120° C. for 2 h. The solution was cooled, diluted with ethyl acetate, washed (saturated ammonium chloride, water), dried and evaporated to give a solid, which was collected and washed two times with ether:hexane (1:1), to provide ethyl 1-allyl-2-phenylpyrimidin-6(1H)-one-5-carboxylate as a white solid (62.5 g); 300 MHz NMR: 8.56 (s,1), 7.54 (m,5), 5.80 (m,1), 5.09 (d,1), 4.82 (d,1), 4.47 (d,2), 4.28 (q,2), 1.28 (t,3).

c. 1-Allyl-2-phenylpyrimidin-6(1H)-one-5-carboxylic acid

To a solution of ethyl 1-allyl-2-phenylpyrimidin-6(1H)-one-5-carboxylate (25.6 g) in tetrahydrofuran (300 mL) at 0° C. was added a solution of 0.5N sodium hydroxide (198 mL). The resulting solution was allowed to stir for 1 h, was poured into dichloromethane and the organic layer removed. The remaining basic aqueous fraction was extracted with dichloromethane, made acidic with 1N hydrochloric acid (to pH 2), and extracted with dichloromethane. The organic layers from the acidic extractions were dried and evaporated to give an oil which crystallized upon addition of ether. The resulting white solid was collected and washed with ether:hexane (1:1) to give 1-allyl-2-phenylpyrimidin-6(1H)-one-5-carboxylic acid (11.1 g); 300 MHz NMR: 13.0 (s broad,1), 8.69 (s,1), 7.58 (m,5), 5,82 (m,1), 5.16 (d,1), 4.87 (d,1), 4.51 (d,2).

d. 1-Allyl-5-benzyloxycarbonylamino-2-phenylpyrimid-6-(1H)-one

To a solution of 1-allyl-2-phenylpyrimidin-6(1H)-one-5-carboxylic acid (30.2 g) and triethylamine (32.8 mL) in dioxane (390 mL) was added diphenylphosphoryl azide (25.6 mL), and the resulting solution was heated at 100° C. for 2 h. Benzyl alcohol (24.5 mL) was added and the resulting solution was heated at 100° C. for 12 h. The solution was cooled and the solvent evaporated. The resulting residue was dissolved in ethyl acetate, washed (saturated ammonium chloride, 1N sodium hydroxide, water), dried, and evaporated to give an oil which crystallized upon addition of ether to give a white solid. The solid was collected and washed with ether to provide 1-allyl-5-benzyloxycarbonylamino-2-phenylpyrimid-6(1H)-one (25.1 g); 300 MHz NMR: 8.93 (s,1), 8.45 (s,1), 7.43 (m,10), 5.75 (m,1), 5.18 (s,2), 5.08 (d,1), 4.82 (d,1), 4.46 (d,2).

e. 5-Benzyloxycarbonylamino-6-oxo-2-phenyl-1,6-dihydro-1-pyrimidinylacetaldehyde To a solution of 1-allyl-5-benzyloxycarbonylamino-2-phenylpyrimid-6(1H)-one in tetrahydrofuran (200 mL) and water (30 mL) was added N-methylmorpholine-N-oxide (9.82 g) and osmium tetroxide (4.4 mL, 4% in water). The resulting solution was allowed to stir overnight. N-Methylmorpholine-N-oxide (1.65 g) was added and the solution was allowed to stir for 4 h. Sodium thiosulfate (saturated aqueous solution, 10 mL) and diatomoaceous earth (30 g) were added and the mixture was stirred for 0.5 h. The mixture was filtered and evaporated to give an oil. This oil was dissolved in ethyl acetate, washed (saturated aqueous sodium thiosulfate solution, 1N hydrochloric acid, brine), and evaporated to give an oil. This oil was dissolved in ethanol (230 mL) and a solution of sodium periodate (27 g) in water (40 mL) was added. The mixture was stirred for 2 h, filtered through diatomaceous earth and evaporated. The residue was dissolved in ethyl acetate and the solution was washed with water, dried, and evaporated to provide 5-benzyloxycarbonylamino-6-oxo-2-phenyl-1,6-dihydro-1-pyrimidinylacetaldehyde (25 g) as a white solid; TLC: ethyl acetate:diethyl ether (1:1), R$_f$=0.8.

f. 5-Benzyloxycarbonylamino-6-oxo-2-phenyl-1,6-dihydro-1-pyrimidinylacetic acid

To a solution of 5-benzyloxycarbonylamino-6-oxo-2-phenyl-1,6-dihydro-1-pyrimidinylacetaldehyde (25 g) in tert-butyl alcohol (175 mL), and 2-methyl-2-butene (148 mL) at 0° C. was added a solution of sodium chlorite (57 g) and sodium dihydrogen phosphate monohydrate (67 g) in water (190 mL). The mixture was allowed to stir for 3 h and was evaporated. The resulting material was diluted with ethyl acetate and extracted with 1N aqueous sodium hydroxide. The aqueous solution was acidified to pH 3 with hydrochloric acid and was extracted with dichloromethane. The organic extracts were dried and evaporated to give a white solid, which was washed with ether:hexane (1:1) to yield the acid (17.2 g); 300 MHz NMR: 13.3 (s,1), 9.04 (s,1), 8.48 (s,1), 7.43 (m,10), 5.19 (s,2), 4.51 (s,2).

g. 2-(5-Benzyloxycarbonylamino-6-oxo-2-phenyl-1,6-dihydro-1-pyrimidinyl)-N-(3,3,3-trifluoro-2-hydroxy-1-isopropylpropyl)acetamide To a solution of 5-benzyloxycarbonylamino-6-oxo-2-phenyl-1,6-dihydro-1-pyrimidinylacetic acid (12.9 g), 3-amino-1,1,1-trifluoro-4-methyl-2-pentanol hydrochloride (10.6 g), 1-hydroxybenzotriazole hydrate (9.2 g), and triethylamine (9.5 mL) in N,N-dimethylformamide (115 mL) at 25° C. was added 1-(3-dimethylaminopropyl)-3-ethylcarbodimide (7.8 g). The resulting solution was allowed to stir for two days, was diluted with ethyl acetate, washed (saturated ammonium chloride, 1N sodium hydroxide, water), dried, and evaporated to give a white solid, which was collected and washed with ether:hexane (1:1) to provide pure 2-(5-benzyloxycarbonylamino-6-oxo-2-phenyl-1,6-dihydro-1-pyrimidinyl)-N-(3,3,3-trifluoro-2-hydroxy-1-isopropylpropyl)acetamide (15.5 g); NMR: 8.95 (s,1), 8.45 (s,1), 8.00 (d,1), 7.45 (m,9), 8.51 (d,1), 5.18 (s,2), 4.46 (m,2), 4.10 (m,1), 3.82 (t,1), 1.72 (m,1), 0.86 (d,3), 0.73 (d,3); MS: m/z=533(M+1).

EXAMPLE 2

2-(5-Acetamido-6-oxo-2-phenyl-1,6-dihydro-1-pyrimidinyl)-N-(3,3,3-trifluoro-1-isopropyl-2-oxopropyl)acetamide.

To a solution of 2-(5-acetamido-6-oxo-2-phenyl-1,6-dihydro-1-pyrimidinyl)-N-(3,3,3-trifluoro-2-hydroxy-1-isopropylpropyl)acetamide (0.6 g) in toluene (4 mL) and dimethyl sulfoxide (4 mL) was added 1-(3-dimethylaminopropyl)-3-ethylcarbodimide (2.4 g) and dichloroacetic acid (0.41 mL). The resulting solution was allowed to stir for 1 h, was poured into 1N hydrochloric acid, and was extracted with ethyl acetate. The organic solution was washed (1N hydrochloric acid, water), dried, and evaporated. The resulting oil crystallized upon addition of ether to give a white solid, which was collected and washed with ether:hexane (1:1) to provide 2-(5-acetamido-6-oxo-2-phenyl-1,6-dihydro-1-pyrimidinyl)-N-(3,3,3-trifluoro-1-isopropyl-2-oxopropyl)acetemide (0.35 g); NMR (DMSO/D$_2$O): 8.77 (s,1), 7.50 (m,5), 4.80 (d,1), 4.53 (d,1), 4.03 (m,1), 2.24 (m,1), 2.18 (s,3), 0.84 (d,3), 0.77 (d,3).

Analysis for C$_{20}$H$_{21}$F$_3$N$_4$O$_7$: Calculated: C, 54.8; H, 4.82; N, 12.8. Found: C, 53.9; H, 4.77; N, 12.6.

The intermediate 2-(5-acetamido-6-oxo-2-phenyl-1,6-dihydro-1-pyrimidinyl)-N-(3,3,3-trifluoro-2-hydroxy-1-isopropylpropyl)acetamide was prepared as follows:

a. 2-(5-Benzyloxycarbonylamino-6-oxo-2-phenyl-1,6-dihydro-1-pyrimidinyl)-N-(2-tert-butyldimethylsilyloxy-3,3,3-trifluoro-1-isopropylpropyl)acetamide To a suspension of 2-(5-benzyloxycarbonylamino-6-oxo-2-phenyl-1,6-dihydro-1-pyrimidinyl)-N-(3,3,3-trifluoro-2-hydroxy-1-isopropylpropyl)acetamide (1.13 g) and 2,6-lutidine (0.5 mL) in dichloromethane (5 mL) at 0° C. was added tert-butyldimethylsilyl trifluoromethanesulfonate (0.73 mL). The mixture was allowed to stir for 1.5 h. over which time the suspension became a solution. The mixture was poured into 1N hydrochloric acid and extracted into ether. The organic layer was washed (water), dried and evaporated to give an oil, which crystallized upon addition of ether:hexane to give a white solid. The solid was collected and washed with hexane to yield 2-(5-benzyloxycarbonylamino-6-oxo-2-phenyl-1,6-dihydro-1-pyrimidinyl)-N-(2-tert-butyldimethylsilyloxy-3,3,3-trifluoro-1-isopropylpropyl)acetamide as a white solid (1.1 g); MS: m/z=647(M+1).

b. 2-(5-Amino-6-oxo-2-phenyl-1,6-dihydro-1-pyrimidinyl)-N-(2-tert-butyldimethylsilyloxy-3,3,3-trifluoro-1-isopropylpropyl)acetamide To a solution of 2-(5-benzyloxycarbonylamino-6-oxo-2-phenyl-1,6-dihydro-1-pyrimidinyl)-N-(2-tert-butyldimethylsilyloxy-3,3,3-trifluoro-1-isopropylpropyl)acetamide (12.4 g) in tetrahydrofuran (100 mL) and ethanol (60 mL) was added 10% (w/w) palladium on carbon (1 g) and the suspension was placed under a hydrogen atmosphere (3.4 bar) and shaken for 12 h. The solution was filtered through diatomaceous earth to give an oil which crystallized from ether to provide 2-(5-amino-6-oxo-2-phenyl-1,6-dihydro-1-pyrimidinyl)-N-(2-tert-butyldimethylsilyloxy-3,3,3-trifluoro-1-isopropylpropyl)acetamide as a white solid (8.7 g); MS: m/z=513(M+1).

c. 2-(5-Acetamido-6-oxo-2-phenyl-1,6-dihydro-1-pyrimidinyl)-N-(2-tert-butyldimethylsilyloxy-3,3,3-trifluoro-1-isopropylpropyl)acetamide To a solution of 2-(5-amino-6-oxo-2-phenyl-1,6-dihydro-1-pyrimidinyl)-N-(2-tert-butyldimethylsilyloxy-3,3,3-trifluoro-1-isopropylpropyl)acetamide (0.83 g) and triethylamine (0.45 mL) in tetrahydrofuran (10 mL) at 0° C. was added acetyl chloride (0.17 mL) and the resulting solution was allowed to stir for 0.5 h. The mixture was poured into ethyl acetate and the solution was washed (1N hydrochloric acid, water), dried, and evaporated to give 2-(5-acetamido-6-oxo-2-phenyl-1,6-dihydro-1-pyrimidinyl)-N-(2-tert-butyldimethylsilyloxy-3,3,3-trifluoro-1-isopropylpropyl)acetamide as a foamy solid (0.86 g); TLC: R$_f$=0.4, methanol:dichloromethane (5:95).

d. 2-(5-Acetamido-6-oxo-2-phenyl-1,6-dihydro-1-pyrimidinyl)-N-(3,3,3-trifluoro-2-hydroxy-1-isopropylpropyl)acetamide.

To a solution of 2-(5-acetamido-6-oxo-2-phenyl-1,6-dihydro-1-pyrimidinyl)-N-(2-tert-butyldimethylsilyloxy-3,3,3-trifluoro-1-isopropylpropyl)acetamide (0.86 g) in tetrahydrofuran (15 mL) at 0° C. was added tetrabutylammonium fluoride (1.95 mL, 1M in tetrahydrofuran) and the resulting solution was allowed to stir for 5 min. The mixture was poured into saturated aqueous ammonium chloride and the product extracted into ethyl acetate. The organic solution was washed (water), dried, and evaporated. The resulting white solid was collected and washed with ether:hexane to provide 2-(5-acetamido-6-oxo-2-phenyl-1,6-dihydro-1-pyrimidinyl)-N-(3,3,3-trifluoro-1-isopropyl-2-hydroxypropyl)acetamide (0.6 g); NMR: 8.87 (s,1), 8.07 (d,1), 7.57 (m,5), 4.62 (d,1), 4.42 (d,1), 4.10 (m,1), 3.68 (t,1), 2.18 (s,3), 1.80 (m,1), 0.89 (d,3), 0.82 (d,3).

EXAMPLE 3

2-[6-Oxo-2-phenyl-5-(4-pyridylmethoxycarbonylamino)-1,6-dihydro-1-pyrimidinyl]-N-(3,3,3-trifluoro-1-isopropyl-2-oxopropyl)acetamide The title compound was prepared from 2-[6-oxo-2-phenyl-5-(4-pyridylmethoxycarbonylamino)-1,6-dihydro-1-pyrimidinyl]-N-(3,3,3-trifluoro-2-hydroxy-1-isopropylpropyl)acetamide using a similar method to that described in Example 1 to obtain 2-[6-oxo-2-phenyl-5-(4-pyridylmethoxycarbonylamino)-1,6-dihydro-1-pyrimidinyl]-N-(3,3,3-trifluoro-1-isopropyl-2-oxopropyl)acetamide as a white solid (0.6 g); NMR (DMSO/D$_2$O): 8.89 (d,2), 8.49 (s,1), 8.12 (d,2), 7.49 (m,7), 5.49 (s,2), 4.67 (d,1), 4.49 (d,1), 4.04, (d,1), 2.23 (m,1), 0.82 (d,3), 0.74 (d,3).

Analysis for C$_{25}$H$_{24}$F$_3$N$_5$O$_5$: Calculated: C, 56.5; H, 4.55; N, 13.2. Found: C, 55.6; H, 4.68; N, 13.2.

The intermediate 2-[6-oxo-2-phenyl-5-(4-pyridylmethoxycarbonylamino)-1,6-dihydro-1-pyrimidinyl]-N-(3,3,3-trifluoro-2-hydroxy-1-isopropylpropyl)acetamide was prepared as follows:

a. 2-[6-Oxo-2-phenyl-5-(4-pyridylmethoxycarbonylamino)-1,6-dihydro-1-pyrimidinyl]-N-(2-tert-butyldimethylsilyloxy-3,3,3-trifluoro-1-isopropylpropyl)acetamide To a solution of 2-(5-amino-6-oxo-2-phenyl-1,6-dihydro-1-pyrimidinyl)-N-(2-tert-butyldimethylsilyloxy-3,3,3-trifluoro-1-isopropylpropyl)acetamide (1.1 g) and triphosgene (0.93 g) in dichloromethane at 0° C. was added triethylamine (2.0 mL) and the resulting solution was allowed to stir for 0.5 h. To this solution was added 4-pyridylcarbinol and the resulting solution allowed to stir overnight. The solution was poured into saturated aqueous sodium bicarbonate solution and the product was extracted into dichloromethane. The organic solution was washed (saturated aqueous sodium bicarbonate, water), dried, and evaporated. The resulting oil was purified by chromatography, with methanol:dichloromethane (5:95) as the eluent, to provide 2-[6-oxo-2-phenyl-5-(4-pyridylmethoxycarbonylamino)-1,6-dihydro-1-pyrimidinyl]-N-(2-tert-butyldimethylsilyloxy-3,3,3-trifluoro-1-isopropylpropyl)acetamide as a white solid (0.9 g); TLC: R$_f$=0.4, methanol:dichloromethane (5:95).

b. 2-[6-Oxo-2-phenyl-5-(4-pyridylmethoxycarbonylamino)-1,6-dihydro-1-pyrimidinyl]-N-(3,3,3-trifluoro-2-hydroxy-1-isopropylpropyl)acetamide This compound was prepared from 2-[6-oxo-2-phenyl-5-(4-pyridylmethoxycarbonylamino)-1,6-dihydro-1-pyrimidinyl]-N-(2-tert-butyldimethylsilyloxy-3,3,3-trifluoro-1-isopropylpropyl)acetamide by a method similar to that used in Example 2.d. to obtain pure 2-[6-oxo-2-phenyl-5-(4-pyridylmethoxycarbonylamino)-1,6-dihydro-1-pyrimidinyl]-N-(3,3,3-trifluoro-2-hydroxy-1-isopropylpropyl)acetamide as a white solid; 300 MHz NMR: 9.23 (s,1), 8.58 (d,2), 8.46 (s,1), 8.02 (d,1), 7.45 (m,7), 6.54 (d,1), 5.23 (s,2), 4.62 (d,1), 4.43 (d,1), 4.08 (m,1), 3.80 (t,1), 4.17 (m,1), 0.88 (d,3), 0.79 (d,3).

EXAMPLE 4

2-[6-Oxo-2-phenyl-5-[3-(3-pyridylmethyl)ureido]-1,6-dihydro-1-pyrimidinyl]-N-(3,3,3-trifluoro-1-isopropyl-2-oxo-propyl)acetamide 2-[6-Oxo-2-phenyl-5-[3-(3-pyridylmethyl)ureido]-1,6-dihydro-1-pyrimidinyl]-N-(3,3,3-trifluoro-2-hydroxy-1-isopropylpropyl)acetamide was subjected to conditions similar to those described in Example 1. Chromatography, with methanol:dichloromethane (5.95) as the eluent, gave 2-[6-oxo-2-phenyl-5-[3-(3-pyridylmethyl)ureido]-1,6-dihydro-1-pyrimidinyl]-N-(3,3,3-trifluoro-1-isopropyl-2-oxopropyl)acetamide as a white solid; NMR (DMSO/D$_2$O): 8.60 (s,1), 8.42 (m,3), 7.71 (m,1), 7.47 (m,5), 4.58 (d,1), 4.39 (d,1), 4.31 (s,2), 2.20 (m,1), 0.83 (d,3), 0.77 (d,3).

Analysis for C$_{25}$H$_{25}$F$_3$N$_6$O$_4$: Calculated: C, 56.6; H, 4.75; N, 15.8. Found: C, 56.1; H, 4.89; N, 15.5.

The intermediate 2-[6-oxo-2-phenyl-5-[3-(3-pyridylmethyl)ureido]-1,6-dihydro-1-pyrimidinyl]-N-(3,3,3-trifluoro-1-isopropyl-2-hydroxypropyl)acetamide was prepared as follows:

a. 2-[6-Oxo-2-phenyl-5-[3-(3-pyridylmethyl)ureido]-1,6-dihydro-1-pyrimidinyl]-N-(2-tert-butyldimethylsilyloxy-3,3,3-trifluoro-1-isopropylpropyl)acetamide 2-(5-Amino-6-oxo-2-phenyl-1,6-dihydro-1-pyrimidinyl)-N-(2-tert-butyldimethylsilyloxy-3,3,3-trifluoro-1-isopropylpropyl)acetamide and 3-aminomethylpyridine were subjected to a method similar to that described in Example 3.a. Chromatography, with methanol: dichloromethane (5:95) as the eluent, gave 2-[6-oxo-2-phenyl-5-[3-(3-pyridyl)methylureido]-1,6-dihydro-1-pyrimidinyl]-N-(2-tert-butyldimethysilyloxy-3,3,3-trifluoro-1-isopropylpropyl)acetamide as a white solid; MS: m/z=647(M+1).

b. 2-[6-Oxo-2-phenyl-5-[3-(3-pyridylmethyl)ureido]-1,6-dihydro-1-pyrimidinyl]-N-(3,3,3-trifluoro-2-hydroxy-1-isopropylpropyl)acetamide 2-[6-Oxo-2-phenyl-5-[3-(3-pyridylmethyl)ureido]-1,6-dihydro-1-pyrimidinyl]-N-(2-tert-butyldimethylsilyloxy-3,3,3-trifluoro-1-isopropylpropyl)acetamide was subjected to a method similar to that described in Example 2.d. Chromatography, with methanol:dichloromethane (5:95) as the eluent, gave 2-[6-oxo-2-phenyl-5-[3-(3-pyridyl)methylureido]-1,6-dihydro-1-pyrimidinyl]-N-(3,3,3-trifluoro-2-hydroxy-1-isopropylpropyl)acetamide as a white solid; MS: m/z=533(M+1).

EXAMPLE 5

2-[6-Oxo-2-phenyl-5-[3-(4-pyridylmethyl)ureido]-1,6-dihydro-1-pyrimidinyl]-N-(3,3,3-trifluoro-1-isopropyl-2-oxopropyl)acetamide 2-[6-Oxo-2-phenyl-5-[3-(4-pyridylmethyl)ureido]-1,6-dihydro-1-pyrimidinyl]-N-(3,3,3-trifluoro-2-hydroxy-1-isopropylpropyl)acetamide was subjected to a procedure similar to that described in Example 1. Chromatography, with methanol:dichloromethane (10:90) as the eluent, gave 2-[6-oxo-2-phenyl-5-[3-(4-pyridylmethyl)ureido]-1,6-dihydro-1-pyrimidinyl]-N-(3,3,3-trifluoro-1-isopropyl-2-oxopropyl)acetamide as a white solid; NMR (DMSO/D$_2$O): 8.58 (s,1), 8.46 (bs, 2), 7.41 (m,5), 7.27 (d,2), 4.56 (d,1), 4.37 (d,1), 4.32 (s,2), 4.00 (d,1), 2.20 (m,1), 0.79 (d,3), 0.73 (d,3); MS: m/z=531(M+1).

Analysis for C$_{25}$H$_{25}$F$_3$N$_6$O$_4$: Calculated: C, 56.6; H, 4.75; N, 15.8. Found: C, 55.0; H, 4.88; N, 14.8.

The intermediate 2-[6-oxo-2-phenyl-5-[3-(4-pyridylmethyl)ureido]-1,6-dihydro-1-pyrimidinyl]-N-(3,3,3-trifluoro-2-hydroxy-1-isopropylpropyl)acetamide was prepared as follows:

a. 2-[6-Oxo-2-phenyl-5-[3-(4-pyridylmethyl)ureido]-1,6-dihydro-1-pyrimidinyl]-N-(2-tert-butyldimethylsilyloxy-3,3,3-trifluoro-1-isopropylpropyl)acetamide 2-(5-Amino-6-oxo-2-phenyl-1,6-dihydro-1-pyrimidinyl)-N-(3,3,3-trifluoro-2-hydroxy-1-isopropylpropyl)acetamide and 4-aminomethylpyridine were subjected to a procedure similar to that described in Example 3.a. Chromatography, with methanol:dichloromethane (5:95) as the eluent, gave 2-[6-oxo-2-phenyl-5-[3-(4-pyridylmethyl)ureido]-1,6-dihydro-1-pyrimidinyl]-N-(2-tert-butyldimethylsilyloxy-3,3,3-trifluoro-1-isopropylpropyl)acetamide as a white solid; MS: m/z=647(M+1).

b. 2-[6-Oxo-2-phenyl-5-[3-(4-pyridylmethyl)ureido]-1,6-dihydro-1-pyrimidinyl]-N-(3,3,3-trifluoro-2-hydroxy-1-isopropylpropyl)acetamide 2-[6-Oxo-2-phenyl-5-[3-(4-pyridylmethyl)ureido]-1,6-dihydro-1-pyrimidinyl]-N-(2-tert-butyldimethylsilyloxy-3,3,3-trifluoro-1-isopropylpropyl)acetamide was subjected to a procedure similar to that described in Example 2.d. to provide 2-[6-oxo-2-phenyl-5-[3-(3-pyridylmethyl)ureido]-1,6-dihydro-1-pyrimidinyl]-N-(3,3,3-trifluoro-2-hydroxy-1-isopropylpropyl)acetamide as a white solid; MS: m/z=533(M+1).

EXAMPLE 6

2-(5-Amino-6-oxo-2-phenyl-1,6-dihydro-1-pyrimidinyl)-N-(3,3,3-trifluoro-1-isopropyl-2-oxopropyl)acetamide To a solution of 2-(5-benzyloxycarbonylamino-6-oxo-2-phenyl-1,6-dihydro-1-pyrimidinyl)-N-(3,3,3-trifluoro-1-isopropyl-2-oxopropyl)acetamide (1.9 g) in tetrahydrofuran (50 mL) and ethanol (50 mL) was added 10% (w/w) palladium on carbon (0.29 g) and the resulting solution was placed under a hydrogen atmosphere (0.75 bar) for 12 h. The catalyst was removed by filtration through diatomaceous earth and the solvent was evaporated. The resulting oil was crystallized from ether. The product was collected and washed with ether:hexane (1:1) to provide 2-(5-amino-6-oxo-2-phenyl-1,6-dihydro-1-pyrimidinyl)-N-(3,3,3-trifluoro-1-isopropyl-2-oxopropyl)acetamide (1.14 g) as a white solid; NMR (DMSO/D$_2$O): 7.38 (m,6), 4.55 (d,1), 4.37 (d,1), 3.98 (m,1), 2.17 (m,1), 0.79 (d,3), 0.72 (d,3).

Analysis for C$_{18}$H$_{19}$F$_3$N$_4$O$_3$: Calculated: C, 54.5; H, 4.83; N, 14.1. Found: C, 52.2; H, 5.17; N, 13.5.

EXAMPLE 7

2-[6-Oxo-2-phenyl-5-(2-pyridylmethoxycarbonylamino)-1,6-dihydro-1-pyrimidinyl]-N-(3,3,3-trifluoro-1-isopropyl-2-oxopropyl)acetamide 2-(5-Amino-6-oxo-2-phenyl-1,6-dihydro-1-pyrimidinyl)-N-(3,3,3-trifluoro-1-isopropyl-2-oxopropyl)acetamide and 2-pyridylcarbinol were subjected to a procedure similar to that described in Example 3.a. Chromatography, with methanol:dichloromethane (gradient, 3:97, 5:95) as the eluent, gave 2-[6-oxo-2-phenyl-5-(2-pyridylmethoxycarbonylamino)-1,6-dihydro-1-pyrimidinyl]-N-(3,3,3-trifluoro-1-isopropyl-2-oxopropyl)acetamide as a tan solid; 300 MHz NMR (DMSO/D$_2$O): 8.53 (d,1), 8.43 (d,1), 7.80 (t,1), 7.4 (m,7), 5.21 (s,2), 4.57 (d,1), 4.47 (d,1), 4.02 (s,1), 2.20 (m,1), 0.81 (d,3), 0.73 (d,3).

Analysis for C$_{25}$H$_{24}$F$_3$N$_5$O$_5$: Calculated: C, 56.5; H, 4.55; N, 13.1. Found: C, 55.9; H, 4.62; N, 13.0.

EXAMPLE 8

2-[5-Benzyloxycarbonylamino-2-(4-fluorphenyl)-6-oxo-1,6-dihydro-1-pyrimidinyl]-N-(3,3,3-trifluoro-1-isopropyl-2-oxopropyl)acetamide 2-[5-Benzyloxycarbonylamino-2-(4-fluorophenyl)-6-oxo-1,6-dihydro-1-pyrimidinyl]-N-(3,3,3-trifluoro-1-isopropyl-2-hydroxy-propyl)acetamide was oxidized by a procedure similar to that described in Example 1 to afford 2-[5-benzyloxycarbonylamino-2-(4-fluorophenyl)-6-oxo-1,6-dihydro-1-pyrimidinyl]-N-(3,3,3-trifluoro-1-isopropyl-2-oxopropyl)acetamide as a white solid; NMR: 8.42 (s,1), 7.38 (9), 5.17 (s,2), 4.69 (d,1), 4.41 (d,1), 4.00 (s,1), 2.19 (m,1), 0.81 (d,3), 0.70 (d,3).

Analysis for C$_{26}$H$_{24}$F$_4$N$_4$O$_5$: Calculated: C, 56.9; H, 4.41; N, 10.2. Found: C, 56.0; H, 4.43; N, 10.0.

The intermediate 2-[5-benzyloxycarbonylamino-2-(4-fluorophenyl)-6-oxo-1,6-dihydro-1-pyrimidinyl]-N-(3,3,3-trifluoro-2-hydroxy-1-isopropylpropyl)acetamide was prepared as follows:

a. Ethyl 4-fluorobenzimidate hydrochloride

A solution of 4-fluorobenzonitrile (50 g) in tetrahydrofuran (300 mL) and ethanol (60.5 mL) at 0° C. was saturated with anhydrous hydrogen chloride gas and the resulting solution was allowed to stand overnight. The solvent was evaporated and the resulting solid was collected and washed with ether to provide ethyl 4-fluorobenzimidate hydrochloride as a white solid (20 g); NMR: 8.27 (m,2), 7.51 (m,2), 4.63 (q,2), 1.47 (t,3).

b. N-(2,2-Diethoxyethyl)-4-fluorobenzamidine

To a solution of ethyl 4-fluorobenzimidate hydrochloride (18.5 g) in ethanol (90 mL) at 0° C. was added aminoacetaldehyde diethyl acetal (14.5 mL) and the resulting solution was kept at 5° C. overnight. The solvent was evaporated, the resulting oil was dissolved in 1N sodium hydroxide (200 mL), and the solution was extracted with dichloromethane. The organic extracts were dried and evaporated to yield N-(2,2-diethoxyethyl)-4-fluorobenzamidine as an oil (21 g); MS: m/z=255(M+1).

c. Ethyl 1-(2,2-diethoxyethyl)-2-(4-fluorophenyl)-pyrimin-6(1H)-one-5-carboxylate This compound was prepared from diethyl ethoxymethylenemalonate and N-(2,2-diethoxyethyl)-4-fluorobenzamidine by a procedure similar to that described in Example 1.b. to obtain ethyl 1-(2,2-diethoxyethyl)-2-(4-fluorophenyl)pyrimidin-6(1H)-one-5-carboxylate as an oil; MS: m/z=379(M+1).

d. 1-(2,2-Diethoxyethyl)-2-(4-fluorophenyl)pyrimidin-6(1H)-one-5-carboxylic acid This compound was prepared from ethyl 1-(2,2-diethoxyethyl)-2-(4-fluorophenyl)pyrimidin-6(1H)-one-5-carboxylate by a procedure similar to that describe in Example 1.c. to obtain the title compound as a white solid; 300 MHz NMR: 8.66 (s,1), 7.69 (m,2), 7.40 (m,2), 4.69 (t,1), 4.05 (d,2), 3.39 (m,4), 0.99 (t,6).

e. 5-Benzyloxycarbonylamino-2-(4-fluorophenyl)-6-oxo-1,6-dihydro-1-pyrimidinylacetaldehyde diethyl acetal This compound was prepared from 1-(2,2-diethoxyethyl)-2-(4-fluorophenyl)pyrimidin-6(1H)-one-5-carboxylic acid by a procedure similar to that used in Example 1.d. to obtain 5-benzyloxycarbonylamino-2-(4-fluorophenyl)-6-oxo-1,6-dihydro-1-pyrimidinylacetaldehyde diethyl acetal as a white solid; TLC: R$_f$=0.6, ether:hexane (75:25).

f. 5-Benzyloxycarbonylamino-2-(4-fluorophenyl)-6-oxo-1,6-dihydro-1-pyrimidinylacetaldehyde A solution of 5-benzyloxycarbonylamino-2-(4-fluorophenyl)-6-oxo-1,6-dihydro-1-pyrimidinylacetaldehyde diethylacetal in tetrahydrofuran (7 mL) and 1N hydrochloric acid (5 mL) was heated at 60° C. for 18 h. The solution was cooled and neutralized with saturated aqueous sodium bicarbonate solution (pH 6). The solution was extracted with ethyl acetate and the organic extracts were dried and evaporated to give 5-benzyloxycarbonylamino-2-(4-fluorophenyl)-6-oxo-1,6-dihydro-1-pyrimidinylacetaldehyde as a white solid; NMR: 9.51 (s,1), 9.03 (s,1), 8.47 (s,1), 7.43 (m,9), 5.19 (s,2), 4.76 (s,2).

g. 5-Benzyloxycarbonylamino-2-(4-fluorophenyl)-6-oxo-1,6-dihydro-1-pyrimidinylacetic acid This compound was prepared from 5-benzyloxycarbonylamino-2-(4-fluorophenyl)-6-oxo-1,6-dihydro-1-pyrimidinylacetaldehyde by a procedure similar to that described in Example 1.f. to provide 5-benzyloxycarbonylamino-2-(4-fluorophenyl)-6-oxo-1,6-dihydro-1-pyrimidinylacetic acid as a white solid; 300 MHz NMR: 9.06 (s,1), 8.46 (s,1), 7.42 (m,9), 5.19 (s,2), 4.52 (s,2).

h. 2-[5-Benzyloxycarbonylamino-2-(4-fluorophenyl)-6-oxo-1,6-dihydro-1-pyrimidinyl]-N-(3,3,3-trifluoro-2-hydroxy-1-isopropylpropyl)acetamide The title compound was prepared from 5-benzyloxycarbonylamino-2-(4-fluorophenyl)-6-oxo-1,6-dihydro-1-pyrimidinylacetic acid and 3-amino-1,1,1-trifluoro-4-methyl-2-pentanol hydrochloride by a procedure similar to that described in Example 1.g. to provide 2-[5-benzyloxycarbonylamino-2-(4-fluorophenyl)-6-oxo-1,6-dihydro-1-pyrimidinyl]-N-(3,3,3-trifluoro-2-hydroxy-1-isopropylpropyl)acetamide as a white solid; NMR: 8.94 (s,1), 8.44 (s,1), 7.97 (d,1), 7.4 (m,9), 6.50 (d,1), 5.18 (s,2), 4.65 (d,1), 4.38 (d,1), 4.08 (m,1), 3.80 (t,1), 1.72 (m,1), 0.85 (d,3), 0.78 (d,3).

EXAMPLE 9

2-[2-(4-Fluorophenyl)-6-oxo-5-(4-pyridylmethoxycarbonylamino)-1,6-dihydro-1-pyrimidinyl]-N-(3,3,3-trifluoro-1-isopropyl-2-oxopropyl)acetamide.

2-[2-(4-Fluoropheny)-6-oxo-5-(4-pyridylmethoxycarbonylamino)-1,6-dihydro-1-pyrimidinyl]-N-(3,3,3-trifluoro-2-hydroxy-1-isopropylpropyl)acetamide was subjected to a procedure similar to that described in Example 1. Chromatography, with methanol:dichloromethane (gradient, 5:95, 7:93) as the eluent, gave 2-[2-(4-fluorophenyl)-6-oxo-5-(4-pyridylmethoxycarbonylamino)-1,6-dihydro-1-pyrimidinyl]-N-(3,3,3-trifluoro-1-isopropyl-2-oxopropyl)acetamide as a white solid; NMR (DMSO/D₂O): 8.54 (d,2), 8.44 (s,1), 7.53 (m,2), 7.44 (d,2), 7.22 (t,2), 5.22 (s,2), 4.70 (d,1), 4.49 (d,1), 4.01, (d,1), 2.20 (m,1), 0.85 (d,3), 0.72 (d,3).

Analysis for $C_{25}H_{23}F_4N_3O_5$: Calculated: C, 54.6; H, 4.22; N, 12.7. Found: C, 53.6; H, 4.29; N, 12.5.

The intermediate 2-[2-(4-fluorophenyl)-6-oxo-5-(4-pyridylmethoxycarbonylamino)-1,6-dihydro-1-pyrimidinyl]-N-(3,3,3-trifluoro-2-hydroxy-1-isopropylpropyl)acetamide was prepared as follows:

a. 2-[5-Benzyloxycarbonylamino-2-(4-fluorophenyl)-6-oxo-1,6-dihydro-1-pyrimidinyl]-N-(2-tert-butyldimethylsilyloxy-3,3,3-trifluoro-1-isopropylpropyl)acetamide.

2-[5-Benzyloxycarbonylamino-2-(4-fluorophenyl)-6-oxo-1,6-dihydro-1-pyrimidinyl]-N-(3,3,3-trifluoro-2-hydroxy-1-isopropylpropyl)acetamide was subjected to a procedure similar to that described in Example 2.a. to provide 2-[5-benzyloxycarbonylamino-2-(4-fluorophenyl)-6-oxo-1,6-dihydro-1-pyrimidinyl]-N-(2-tert-butyldimethylsilyloxy-3,3,3-trifluoro-1-isopropylpropyl)acetamide as a white solid; MS: m/z=665(M+1).

b. 2-[5-Amino-2-(4-fluorophenyl)-6-oxo-1,6-dihydro-1-pyrimidinyl]-N-(2-tert-butyldimethylsilyloxy-3,3,3-trifluoro-1-isopropylpropyl)acetamide.

2-[5-Benzyloxycarbonylamino-2-(4-fluorophenyl)-6-oxo-1,6-dihydro-1-pyrimidinyl]-N-(2-tert-butyldimethylsilyloxy-3,3,3-trifluoro-1-isopropylpropyl)acetamide was subjected to a procedure similar to that described in Example 2.b. to provide 2-[5-amino-2-(4-fluorophenyl)-6-oxo-1,6-dihydro-1-pyrimidinyl]-N-(2-tert-butyldimethylsilyloxy-3,3,3-trifluoro-1-isopropylpropyl)acetamide as a gray-white solid; MS: m/z=531(M+1).

c. 2-[2-(4-Fluorophenyl)-6-oxo-5-(4-pyridylmethoxycarbonylamino)-1,6-dihydro-1-pyrimidinyl]-N-(2-tert-butyldimethylsilyloxy-3,3,3-trifluoro-1-isopropylpropyl)acetamide.

2-[5-Amino-2-(4-fluorophenyl)-6-oxo-1,6-dihydro-1-pyrimidinyl]-N-(2-tert-butyldimethylsilyloxy-3,3,3-trifluoro-1-isopropylpropyl)acetamide and 4-pyridylcarbinol were subjected to a procedure similar to that described in Example 3.a. Chromatography, with methanol:dichloromethane (5:95) as the eluent, gave 2-[2-(4-fluorophenyl)-6-oxo-5-(4-pyridylmethoxycarbonylamino)-1,6-dihydro-1-pyrimidinyl]-N-(2-tert-butyldimethylsilyloxy-3,3,3-trifluoro-1-isopropylpropyl)acetamide as a yellow solid; MS: m/z=666(M+1).

d. 2-[2-(4-Fluorophenyl)-6-oxo-5-(4-pyridylmethoxycarbonylamino)-1,6-dihydro-1-pyrimidinyl]-N-(3,3,3-trifluoro-2-hydroxy-1-isopropylpropyl)acetamide.

2-[2-(4-Fluorophenyl)-6-oxo-5-(4-pyridylmethoxycarbonylamino)-1,6-dihydro-1-pyrimidinyl]-N-(2-tert-butyldimethylsilyloxy-3,3,3-trifluoro-1-isopropylpropyl)acetamide was subjected to a procedure similar to that described in Example 2.d. Chromatography with methanol:dichloromethane (gradient, 5:95, 7:93) as the eluent, gave 2-[2-(4-fluorophenyl)-6-oxo-5-(4-pyridylmethoxycarbonylamino)-1,6-dihydro-1-pyrimidinyl]-N-(3,3,3-trifluoro-2-hydroxy-1-isopropylpropyl)acetamide as a white solid; MS: m/z=552(M+1).

EXAMPLE 10

2-[2-(4-Fluorophenyl)-6-oxo-5-(2-pyridylmethoxycarbonylamino)-1,6-dihydro-1-pyrimidinyl]-N-(3,3,3-trifluoro-1-isopropyl-2-oxopropyl)acetamide 2-[2-(4-Fluorophenyl)-6-oxo-5-(2-pyridylmethoxycarbonylamino)-1,6-dihydro-1-pyrimidinyl]-N-(3,3,3-trifluoro-2-hydroxy-1-isopropylpropyl)acetamide was subjected to a procedure similar to that described in Example 1. Chromatography, with methanol:dichloromethane (gradient, 0:100, 5:95, 7:93) as the eluent, gave 2-[2-(4-fluorophenyl)-6-oxo-5-(2-pyridylmethoxycarbonylamino)-1,6-dihydro-1-pyrimidinyl]-N-(3,3,3-trifluoro-1-isopropyl-2-oxopropyl)acetamide as a white solid; NMR (DMSO/H₂O): 8.54 (d,2), 8.43 (s,1), 7.82 (m,1), 7.53 (m,3), 7.30 (m,3), 5.22 (s,2), 4.62 (d,1), 4.42 (d,1), 4.00, (d,1), 2.19 (m,1), 0.81 (d,3), 0.70 (d,3).

Analysis for $C_{25}H_{23}F_4N_3O_5$: Calculated: C, 54.6; H, 4.22; N, 12.7. Found: C, 54.0; H, 4.56; N, 12.2.

The intermediate 2-[2-(4-fluorophenyl)-6-oxo-5-(2-pyridylmethoxycarbonylamino)-1,6-dihydro-1-pyrimidinyl]-N-(3,3,3-trifluoro-2-hydroxy-1-isopropylpropyl)acetamide was prepared as follows:

a. 2-[2-(4-Fluorophenyl)-6-oxo-5-(2-pyridylmethoxycarbonylamino)-1,6-dihydro-1-pyrimidinyl]-N-(2-tert-butyldimethylsilyloxy-3,3,3-trifluoro-1-isopropylpropyl)acetamide 2-[5-Amino-2-(4-fluorophenyl)-6-oxo-1,6-dihydro-1-pyrimidinyl]-N-(2-tert-butyldimethylsilyloxy-3,3,3-trifluoro-1-isopropylpropyl)acetamide and 2-pyridylcarbinol were subjected to a procedure similar to that described in Example 3.a. Chromatography, with methanol:dichloromethane (gradient, 2:98, 5:95) as the eluent, gave 2-[2-(4-fluorophenyl)-6-oxo-5-(2-pyridylmethoxycarbonylamino)-1,6dihydro-1-pyridmidinyl]-N-(2-tert-butyldimethylsilyloxy-3,3,3-trifluoro-1-isopropylpropyl)acetamide as a gum; MS: m/z=666(M+1).

b. 2-[2-(4-Fluorophenyl)-6-oxo-5-(2-pyridylmethoxycarbonylamino)-1,6-dihydro-1-pyrimidinyl]-N-(3,3,3-trifluoro-2-hydroxy-1-isopropylpropyl)acetamide.

2-[2-(4-Fluorophenyl)-6-oxo-5-(2-pyridylmethoxycarbonylamino)-1,6-dihydro-1-pyrimidinyl]-N-(2-tert-butyldimethylsilyloxy-3,3,3-trifluoro-1-isopropylpropyl)acetamide was subjected to a procedure similar to that described in Example 2.d. to provide 2-[2-(4-fluorophenyl)-6-oxo-5-(2-pyridylmethoxycarbonylamino)-1,6-dihydro-1-pyrimidinyl]-N-(3,3,3-trifluoro-2-hydroxy-1-isopropylpropyl)acetamide as a white solid; MS: m/z=552(M+1).

EXAMPLE 11

2-[5-Benzyloxycarbonylamino-6-oxo-2-(2-thienyl)-1,6-dihydro-1-pyrimidinyl]-N-(3,3,3-trifluoro-1-isopropyl-2-oxopropyl)acetamide 2-[5-Benzyloxycarbonylamino-6-oxo-2-(2-thienyl)-1,6-dihydro-1-pyrimidinyl)-N-(3,3,3-trifluoro-2-hydroxy-1-isopropylpropyl]acetamide was oxidized using a procedure similar to that described in Example 1. Chromatography, with ethyl acetate:dichloromethane (gradient, 15:85, 30:70) as the eluent, gave 2-[5-benzyloxycarbonylamino-6-oxo-2-(2-thienyl)-1,6-dihydro-1-pyrimidinyl)-N-(3,3,3-trifluoro-1-isopropyl-2-oxopropyl]acetamide as a white solid; 300 MHz NMR (DMSO/D2O): 8.41 (s,1), 7.79 (d,1), 7.35 (m,6), 7.10 (m,1), 5.17 (s,2), 4.90 (d,1), 4.76 (d,1), 4.08 (d,1), 2.25 (m,1), 0.90 (d,3), 0.75 (d,3).

Analysis for $C_{24}H_{23}F_3N_4O_5S$: Calculated: C, 53.7; H, 4.32; N, 10.4. Found: C, 52.4; H, 4.49; N, 10.2.

The intermediate 2-[5-benzyloxycarbonylamino-6-oxo-2-(2-thienyl)-1,6-dihydro-1-pyrimidinyl]-N-(3,3,3-trifluoro-2-hydroxy-1-isopropylpropyl)acetamide was prepared as follows:

a. Ethyl 2-thiophenecarboximidate hydrochloride

2-Thiophenecarbonitrile was subjected to a procedure similar to that described in Example 8.a. to provide ethyl 2-thiophenecarboximidate hydrochloride as a white solid; MS: m/z=156(M+1).

b. N-(2,2-Dimethoxyethyl)-2-thiophenecarboximidine

Ethyl 2-thiophenecarboximidate hydrochloride and aminoacetaldehyde dimethyl acetal were subjected to a procedure similar to that described in Example 8.b. to provide N-(2,2-dimethoxyethyl)-2-thiophenecarboximidate as a white solid; 300 MHz NMR (DMSO/D2O): 8.07 (m,1), 7.91 (m,1), 7.33 (m,1), 4.67 (t,1), 3.84 (s,6), 3.60 (d,2).

c. Ethyl 1-(2,2-dimethoxyethyl)-2-(2-thienyl)pyrimidin-6(1H)-one-5-carboxylate

N-(2,2-Dimethoxyethyl)-2-thiophenecarboximidate and diethyl ethoxymethylenemalonate were subjected to a procedure similar to that described in Example 1.b. to provide ethyl 1-(2,2-dimethoxyethyl)-2-(2-thienyl)-pyrimidin-6(1H)-one-5-carboxylate as a yellow solid; MS: m/z=339(M+1).

d. 1-(2,2-Dimethoxyethyl)-2-(2-thienyl)pyrimidin-6(1H)-one-5-carboxylic acid

To a solution of ethyl 1-(2,2-dimethoxyethyl)-2-(2-thienyl)pyrimidin-6(1H)-one-5-carboxylate in pyridine (33 mL) was added lithium iodide (3.32 g) and the resulting mixture was heated at 110° C. overnight. The pyridine was evaporated and residual traces of pyridine were removed by evaporation with toluene. The residue was dissolved in 1N hydrochloric acid and the product was extracted into ethyl acetate. The solution was dried and evaporated to give an oil which crystallized from ether to provide 1-(2,2-dimethoxyethyl)-2-(2-thienyl)pyrimidin-6(1H)-one-5-carboxylic acid as a brown solid; MS: m/z=311(M+1).

e. 5-Benzyloxycarbonylamino-6-oxo-2-(2-thienyl)-1,6-dihydro-1-pyrimidinylacetaldehyde dimethyl acetal 1-(2,2-Dimethoxyethyl)-2-(2-thienyl)pyrimidin-6(1H)-one-5-carboxylic acid was subjected to a procedure similar to that described in Example 1.d. Chromatography, with ether:hexane (gradient, 25:75, 80:20) as the eluent, gave 5-benzyloxycarbonylamino-6-oxo-2-(2-thienyl)-1,6-dihydro-1-pyrimidinylacetaldehyde dimethyl acetal as a yellow solid; MS: m/z=416(M+1).

f. 5-Benzyloxycarbonylamino-6-oxo-2-(2-thienyl)-1,6-dihydro-1-pyrimidinylacetaldehyde 5-Benzyloxycarbonylamino-6-oxo-2-(2-thienyl)-1,6-dihydro-1-pyrimidinylacetaldehyde dimethyl acetal was subjected to a procedure similar to that described in Example 8.f. to provide 5-benzyloxycarbonylamino-6-oxo-2-(2-thienyl)-1,6-dihydro-1-pyrimidinylacetaldehyde as a yellow foam; MS: m/z=370(M+1).

g. 5-Benzyloxycarbonylamino-6-oxo-2-(2-thienyl)-1,6-dihydro-1-pyrimidinylacetic acid 5-Benzyloxycarbonylamino-6-oxo-2-(2-thienyl)-1,6-dihydro-1-pyrimidinylacetaldehyde was subjected to a procedure similar to that described in Example 1.f. to provide 5-benzyloxycarbonylamino-6-oxo-2-(2-thienyl)-1,6-dihydro-1-pyrimidinylacetic acid as a yellow solid; MS: m/z=386(M+1).

h. 2-[5-Benzyloxycarbonylamino-6-oxo-2-(2-thienyl)-1,6-dihydro-1-pyrimidinyl]-N-(3,3,3-trifluoro-2-hydroxy-1-isopropylpropyl)acetamide 5-Benzyloxycarbonylamino-6-oxo-2-(2-thienyl)-1,6-dihydro-1-pyrimidinylacetic acid and 3-amino-1,1,1-trifluoro-4-methyl-2-pentanol hydrochloride were subjected to a procedure similar to that described in Example 1.g. to provide 2-[5-benzyloxycarbonylamino-6-oxo-2-(2-thienyl)-1,6-dihydro-1-pyrimidinyl]-N-(3,3,3-trifluoro-1-isopropyl-2-hydroxypropyl)acetamide as a yellow solid; MS: m/z=539(M+1).

EXAMPLE 12

2-[5-Amino-6-oxo-2-(2-thienyl)-1,6-dihydro-1-pyrimidinyl]-N-(3,3,3-trifluoro-1-isopropyl-2-oxopropyl)acetamide To a solution of 2-[5-benzyloxycarbonylamino-6-oxo-2-(2-thienyl)-1,6-dihydro-1-pyrimidinyl]-N-(3,3,3-trifluoro-1-isopropyl-2-oxopropyl)acetamide in dichloromethane (35 mL) and anisole (1.2 mL) at 0° C. was added trifluoromethanesulfonic acid, and the resulting suspension was stirred for 15 minutes. The reaction was quenched by addition of sodium bicarbonate and the product extracted into ethyl acetate. The organic layer was washed (brine) and dried. The solvent was removed and the residue was purified by chromatography, with methanol:dichloromethane (gradient, 5:95, 7:93) as the eluent, to provide 2-[5-amino-6-oxo-2-(2-thienyl)-1,6-dihydro-1-pyrimidinyl]-N-(3,3,3-trifluoro-1-isopropyl-2-oxopropyl)acetamide as a yellow solid; 300 MHz NMR (DMSO/D$_2$O): 7.94 (d,1), 7.65 (d,1), 7.30 (s,1), 7.22 (d,1), 7.02 (m,1), 4.84 (d,1), 4.69 (d,1), 4.07 (d,1), 2.24 (m,1), 0.89(d,3), 0.76 (d,3).

Analysis for C$_{16}$H$_{17}$F$_3$N$_4$O$_3$S: Calculated: C, 47.7; H, 4.26; N, 13.9. Found: C, 56.8; H, 4.58; N, 13.3.

EXAMPLE 13

2-[5-Benzyloxycarbonylamino-6-oxo-2-(3-pyridyl)-1,6-dihydro-1-pyrimidinyl]-N-(3,3,3-trifluoro-1-isopropyl-2-oxopropyl)acetamide 2-[5-Benzyloxycarbonylamino-6-oxo-2-(3-pyridyl)-1,6-dihydro-1-pyrimidinyl]-N-(3,3,3-trifluoro-2-hydroxy-1-isopropylpropyl)acetamide was subjected to a procedure similar to that described in example 1 to obtain pure 2-[5-benzyloxycarbonylamino-6-oxo-2-(3-pyridyl)-1,6-dihydro-1-pyrimidinyl]-N-(3,3,3-trifluoro-1-isopropyl-2-oxopropyl)acetamide as a white solid; NMR (DMSO/D$_2$O): 8.84 (m,2), 8.44 (s,1), 7.86 (m,1), 7.39 (m,5), 5.18 (s,2), 4.63 (d,1), 4.45 (d,1), 3.97, (d,1), 2.15 (m,1), 0.77 (d,3), 0.65 (d,3).

Analysis for C$_{25}$H$_{24}$F$_3$N$_5$O$_5$: Calculated: C, 56.5; H, 4.55; N, 13.2. Found: C, 55.0; H, 4.60; N, 12.85.

The intermediate 2-[5-benzyloxycarbonylamino-6-oxo-2-(3-pyridyl)-1,6-dihydro-1-pyrimidinyl]-N-(3,3,3-trifluoro-2-hydroxy-1-isopropylpropyl)acetamide was prepared as follows:

a. Ethyl 3-pyridinecarboximidate hydrochloride

To a solution of ethanol (200 mL) in chloroform (100 mL) at 0° C. was added acetyl chloride (190 mL) and a solution of 3-cyanopyridine (25 g) in (300 mL) of chloroform. The solution was allowed to warm to 25° C. and to stand for 1 day. A white solid separated from solution. The solvent was removed and the white solid collected and washed with ether to provide pure ethyl 3-pyridine-carboximidate hydrochloride as a white solid; MS: m/z=152(M+1).

b. N-(2,2-Dimethoxyethyl)-3-pyridinecarboxamidine

Ethyl 3-pyridinecarboximidate hydrochloride and aminoacetaldehyde dimethyl acetal were subjected to a procedure similar to that described in Example 8.b. to provide pure N-(2,2-dimethoxyethyl)-3-pyridinecarboxamidine as an oil; MS: m/z=210(M+1).

c. Methyl 1-(2,2-dimethoxyethyl)-2-(3-pyridyl)-pyrimidin-6(1H)-one-5-carboxylate Dimethyl methoxymethylenemalonate and N-(2,2-dimethoxy-ethyl) -3-pyridinecarboxamidine were subjected to a procedure similar to that described in Example 1.b. Chromatography, with methanol:diethyl ether (gradient, 0:100, 10:90) as the eluent, gave methyl 1-(2,2-dimethoxy-ethyl)-2-(3-pyridyl)pyrimidin-6(1H)-one-5-carboxylate as an oil; MS: m/z=320(M+1); TLC: R$_f$=0.4, methanol:diethyl ether (5:95).

d. 5-Benzyloxycarbonylamino-6-oxo-2-(3-pyridyl)-1,6-dihydro-1-pyrimidinylacetaldehyde dimethyl acetal.

To a solution of methyl 1-(2,2-dimethoxyethyl)-2-(3-pyridyl)pyrimidin-6(1H)-one-5-carboxylate in pyridine (200 mL) was added lithium iodide (48 g) and the mixture heated at 100° C. for 3 h. The solvent was evaporated and residual pyridine removed by addition of toluene (200 mL) followed by evaporation. The resulting material was diluted with water and the pH adjusted to pH 5. The product was extracted into ethyl acetate, dried and evaporated. The resulting crude acid was dissolved in dioxane (260 mL), and to this solution were added triethylamine (22 mL) and diphenylphosphorylazide (18 mL). The solution was heated at 100° C. for 2 h and benzyl alcohol (17 mL) was added. The resulting solution was heated overnight at 100° C., the solvent was removed, and the resulting material was redissolved in ethyl acetate. The solution was washed (1N sodium hydroxide, water, brine), dried, and evaporated. Chromatography, with ethyl acetate:methanol (gradient, 100:0, 70:30) as the eluent, gave 5-benzyloxycarbonylamino-6-oxo-2-(3-pyridyl)-1,6-dihydro-1-pyrimidinylacetaldehyde dimethyl acetal as an oil; MS: m/z=365(M+1).

e. 5-Benzyloxycarbonylamino-6-oxo-2-(3-pyridyl)-1,6-dihydro-1-pyrimidinylacetaldehyde 5-Benzyloxycarbonylamino-6-oxo-2-(3-pyridyl)-1,6-dihydro-1-pyrimidinylacetaldehyde dimethyl acetal was subjected to a procedure similar to that described in Example 8.f. to provide 5-benzyloxycarbonylamino-6-oxo-2-(3-pyridyl)-1,6-dihydro-1-pyrimidinylacetaldehyde as a tan solid; TLC: R$_f$=0.45, methanol:dichloromethane (5:95).

f. 5-Benzyloxycarbonylamino-6-oxo-2-(3-pyridyl)-1,6-dihydro-1-pyrimidinylacetic acid 5-Benzyloxycarbonylamino-6-oxo-2-(3-pyridyl)-1,6-dihydro-1-pyrimidinylacetaldehyde was subjected to a procedure similar to that described in Example 1.f. to provide a white solid which was washed with ether to give 5-benzyloxycarbonylamino-6-oxo-2-(3-pyridyl)-1,6-dihydro-1-pyrimidinylacetic acid as a white solid; NMR: 13.5 (s broad,1), 9.11 (s,1), 8.73 (m,2), 8.51 (s,1), 7.96 (d,1), 7.47 (m,5), 5.20 (s,2), 4.57 (s,2).

g. 2-[5-Benzyloxycarbonylamino-6-oxo-2-(3-pyridyl)-1,6-dihydro-1-pyrimidinyl]-N-(3,3,3-trifluoro-2-hydroxy-1-isopropylpropyl)acetamide 5-Benzyloxycarbonylamino-6-oxo-2-(3-pyridyl)-1,6-dihydro-1-pyrimidinylacetic acid and 3-amino-1,1,1-trifluoro-4-methyl-2-pentanol hydrochloride was subjected to a procedure similar to that described in Example 1.g. Chromatography, with methanol:dichloromethane (5:95) as the eluent, gave 2-[5-benzyloxycarbonylamino-6-oxo-2-(3-pyridyl)-1,6-dihydro-1-pyrimidinyl]-N-(3,3,3-trifluoro-2-hydroxy-1-isopropylpropyl)acetamide as a white solid; MS: m/z=534(M+1).

EXAMPLE 14

2-[5-Amino-6-oxo-2-(3-pyridyl)-1,6-dihydro-1-pyrimidinyl]-N-(3,3,3-trifluoro-1-isopropyl-2-oxopropyl)acetamide 2-[5-Benzyloxycarbonylamino-6-oxo-2-(3-pyridyl)-1,6-dihydro-1-pyrimidinyl]-N-(3,3,3-trifluoro-1-isopropyl-2-oxopropyl)acetamide was subjected to a procedure similar to that described in Example 15 to provide 2-[5-amino-6-oxo-2-(3-pyridyl)-1,6-dihydro-1-pyrimidinyl]-N-(3,3,3-trifluoro-1-isopropyl-2-oxopropyl)acetamide as a white solid; 300 MHz NMR (DMSO/D20): 8.56 (m,2), 7.78 (m,1), 7.41 (m,1), 7.34 (s,1), 4.56 (d,1), 4.48 (d,1), 3.94 (m,1), 2.13 (m,1), 0.75 (d,3), 0.64 (d,3).

Analysis for C$_{17}$H$_{18}$F$_3$N$_5$O$_3$: Calculated: C, 51.38; H, 4.56; N, 17.62. Found: C, 50.79; H, 4.68; N, 17.35.

EXAMPLE 15

2-[5-Amino-2-(4-fluorophenyl)-6-oxo-1,6-dihydro-1-pyrimidinyl]-N-(3,3,3-trifluoro-1-isopropyl-2-oxopropyl)acetamide To a solution of 2-[5-benzyloxycarbonylamino-2-(4-fluorophenyl)-6-oxo-1,6-dihydro-1-pyrimidinyl]-N-(3,3,3-trifluoro-1-isopropyl-2-oxopropyl)acetamide (1.03 g) in ethanol (45 mL) and tetrahydrofuran (22 mL) was added 10% (w/w) palladium on carbon (15% by weight). This mixture was shaken under a hydrogen atmosphere (3 bar), filtered, and additional 10% (w/w) palladium on carbon was added. The mixture was again shaken under hydrogen (3 bar). The solution was filtered and the solvent evaporated. The resulting material was purified by chromatography, with methanol:dichloromethane (gradient, 5:95, 12:88) as the eluent, to give a white solid which was collected and washed with ether to provide 2-[5-amino-2-(4-fluorophenyl)-6-oxo-1,6-dihydr-1-pyrimidinyl]-N-(3,3,3-trifluoro-1-isopropyl-2-oxopropyl)acetamide as a white solid; mp 200°–203° C.; 300 MHz NMR (DMSO/D$_2$O): 7.76 (d,1), 7.47 (m,2), 7.31 (s,1), 7.20 (t,2), 4.56 (d,1), 4.37 (d,1), 4.01 (m,1), 2.20 (m,1), 0.82 (d,3), 0.72 (d,3).

Analysis for C$_{18}$H$_{18}$F$_4$N$_4$O$_3$·0.75H$_2$O: Calculated: C, 50.53; H, 4.59; N, 13.09. Found: C, 50.41; H, 4.69; N, 13.09.

EXAMPLE 16

2-[5-(N,N-Dimethylaminosulfonylamino)-6-oxo-2-phenyl-1,6-dihydro-1-pyrimidinyl]-N-(3,3,3-trifluoro-1-isopropyl-2-oxopropyl)acetamide To a solution of 2-(5-amino-6-oxo-2-phenyl-1,6-dihydro-1-pyrimidinyl)-N-(3,3,3-trifluoro-1-isopropyl-2-oxopropyl)acetamide (0.298 g) in tetrahydrofuran (3 mL) containing sodium carbonate (0.161 g) was added dimethylsulfamoyl chloride (0.1 mL). The mixture was stirred at 60° C. overnight and more sodium carbonate (0.170 g) and dimethylsulfamoyl chloride (0.1 mL) were added. The solution was allowed to stir for 1 day. The reaction was diluted with ethyl acetate and the solution was washed (1N hydrochloric acid, water, 10% aqueous sodium bicarbonate, brine), dried, and evaporated. The resulting oil was purified by chromatography, with tetrahydrofuran:dichloromethane (10:90) as the eluent, to provide 2-[5-(N,N-dimethylsulfamoylamino)-6-oxo-2-phenyl-1,6-dihydro-1-pyrimidinyl]-N-(3,3,3-trifluoro-1-isopropyl-2-oxopropyl)acetamide as a white solid (0.117 g); NMR (DMSO/D$_2$O): 9.29 (s,1), 8.84 (d,1), 7.99 (s,1), 7.48 (m,5), 2.72 (s,3), 2.16 (m,1), 0.89 (d,3), 0.83 (d,3).

Analysis for C$_{20}$H$_{24}$F$_3$N$_5$O$_5$S: Calculated: C, 47.7; H, 4.80; N, 13.9. Found: C, 47.6; H, 4.93; N, 13.5.

EXAMPLE 17

2-(5-Methylsulfonylamino-6-oxo-2-phenyl-1,6-dihydro-1-pyrimidinyl)-N-(3,3,3-trifluoro-1-isopropyl-2-oxopropyl)acetamide To a solution of 2-(5-amino-6-oxo-2-phenyl-1,6-dihydro-1-pyrimidinyl)-N-(3,3,3-trifluoro-1-isopropyl-2-oxopropyl)acetamide (0.345 g) in tetrahydrofuran (7 mL) and triethylamine (0.36 mL) at 0° C. was added methanesulfonoyl chloride (0.19 mL) and the resulting solution was allowed to stir overnight. The mixture was diluted with ethyl acetate and the solution washed (1N hydrochloric acid, water, 5% sodium bicarbonate). The organic layer was dried and evaporated. The residue was dissolved in tetrahydrofuran (1 mL), and to it was added 3N aqueous potassium hydroxide (0.07 mL). The solution was allowed to stir for 12 h. The reaction was quenched by addition of 1N hydrochloric acid and the product was extracted into ethyl acetate. The organic layer was washed (water, brine), and the solution was dried and evaporated. The resulting material was purified by chromatography, with tetrahydrofuran:dichloromethane (10:90) as the eluent, to provide 2-(5-methylsulfonylamino-6-oxo-2-phenyl-1,6-dihydro-1-pyrimidinyl)-N-(3,3,3-trifluoro-1-isopropyl-2-oxopropyl)acetamide as a white solid (0.146 g); NMR (DMSO/D$_2$O): 9.35 (s,1), 8.84 (d,1), 8.01 (s,1), 7.50 (m,5), 4.68 (m,2), 4.55 (d,1), 3.10 (s,3), 2.16 (m,1), 0.89 (d,3), 0.83 (d,3).

Analysis for C$_{19}$H$_{21}$F$_3$N$_4$O$_5$S: Calculated: C, 47.7; H, 4.52; N, 11.7. Found: C, 47.7; H, 4.62; N, 11.5.

EXAMPLES 18–25

Using a procedure similar to that described in Example 1, the following compounds of formula I wherein R$^0$ is isopropyl, R is benzyloxycarbonyl, and R$^6$ is the indicated group were prepared by oxidation of the corresponding alcohols of formula II.

EXAMPLE 18

R$^6$=4-nitrophenyl: Chromatography solvent: ethyl acetate:dichloromethane (gradient, 30:70 to 50:50); TLC: R$_f$=0.6, methanol:dichloromethane (5:95); NMR (DMSO/D$_2$O): 8.44 (s,1), 8.26 (d,2), 7.70 (d,2), 7.36 (m,5), 5.15 (s,2), 4.51 (m,2), 3.97 (d,1), 2.14 (m,1), 0.74 (d,3), 0.63 (d,3).

Analysis for C$_{26}$H$_{24}$F$_3$N$_5$O$_7$: Calculated: C, 54.2; H, 4.20; N, 12.1. Found: C, 54.1; H, 4.23; N, 12.2.

EXAMPLE 19

R$^6$=4-trifluoromethylphenyl: Chromatography solvent: ethyl acetate:hexane (50:50); TLC: R$_f$=0.41, diethyl ether; NMR (DMSO/D$_2$O): 9.07 (s,1), 8.79 (d,1), 8.48 (s,1), 7.84 (d,2), 7.69 (d,2), 7.39 (m,5), 5.17 (s,2), 4.80 (m,3), 2.12 (m,1), 0.83 (d,3), 0.77 (d,3).

Analysis for C$_{27}$H$_{24}$F$_6$N$_4$O$_5$: Calculated: C, 54.2; H, 4.04; N, 9.36. Found: C, 54.1; H, 4.07; N, 9.41.

EXAMPLE 20

R$^6$=3,5-difluorophenyl: Chromatography solvent: tetrahydrofuran:dichloromethane (gradient, 5:95 to 10:90); TLC: R$_f$=0.31, tetrahydrofuran:dichloromethane (8:92); NMR (DMSO/D$_2$O): 8.45 (s,1), 7.20–7.48 (m,8), 5.18 (s,2), 4.67 (d,1), 4.43 (d,1), 4.01 (d,1), 2.22 (m,1), 0.84 (d,3), 0.73 (d,3).

Analysis for C$_{26}$H$_{23}$F$_5$N$_4$O$_5$: Calculated: C, 55.1; H, 4.09; N, 9.89. Found: C, 55.2; H, 4.13; N, 9.89.

EXAMPLE 21

R$^6$=4-methoxyphenyl: Chromatography solvent: ethyl acetate:dichloromethane (20:80); TLC: R$_f$=0.28, methanol:dichloromethane (20:80); NMR: 8.95 (s,1), 8.85 (d,1), 8.43 (s,1), 7.40 (m,7), 6.99 (d,2), 5.18 (s,2), 4.67 (t,1), 4.58 (d,1), 3.81 (s,3), 2.16 (m,1), 0.90 (d,3), 0.84 (d,3).

Analysis for C$_{27}$H$_{27}$F$_3$N$_4$O$_6$: Calculated: C, 57.9; H, 4.85; N, 9.99. Found: C, 57.6; H, 4.91; N, 9.94.

EXAMPLE 22

R$^6$=4-chlorophenyl: Chromatography solvent: methanol:dichloromethane (5:95); TLC: R$_f$=0.4, methanol:dichloromethane (5:95); NMR (DMSO/D$_2$O): 8.39 (s,1), 7.36 (m,9), 5.14 (s,2), 4.49 (m,2), 3.97 (d,2), 2.16 (m,1), 0.77 (d,3), 0.66 (d,3).

Analysis for C$_{26}$H$_{24}$ClF$_3$N$_4$O$_5$: Calculated: C, 55.2; H, 4.28; N, 9.91. Found: C, 55.1; H, 4.23; N, 9.91.

EXAMPLE 23

R$^6$=3,5-bis(trifluoromethyl)phenyl: Chromatography solvent: ethyl acetate:dichloromethane (gradient, 30:70, 50:50); TLC: R$_f$=0.6, methanol:dichloromethane (5:95); NMR (DMSO/D$_2$O): 8.44 (s,1), 8.26 (d,2), 7.70 (d,2), 7.36 (m,5), 5.15 (s,2), 4.51 (m,2), 3.97 (d,1), 2.14 (m,1), 0.74 (d,3), 0.63 (d,3).

Analysis for C$_{26}$H$_{24}$F$_3$N$_5$O$_7$: Calculated: C, 54.2; H, 4.20; N, 12.1. Found: C, 54.1; H, 4.23; N, 12.2.

EXAMPLE 24

R$^6$=cyclohexyl: Chromatography solvent: ethyl acetate:dichloromethane (15:85); TLC: R$_f$=0.55, methanol:dichloromethane (5:95); NMR (DMSO/D$_2$O): 8.22 (s,1), 7.32 (m,5), 5.10 (s,2), 4.79 (m,2), 4.01 (d,1), 2.50 (m,1), 2.25 (m,1), 1.7-1.14 (m,10), 0.92 (d,3), 0.75 (d,3).

Analysis for C$_{26}$H$_{31}$F$_3$N$_4$O$_5$: Calculated: C, 58.2; H, 5.82; N, 10.4. Found: C, 57.9; H, 4.84; N, 10.3.

EXAMPLE 25

R$^6$=isopropyl: Chromatography solvent: ethyl acetate:dichloromethane (gradient, 10:90 to 25:75); TLC: R$_f$=0.4, methanol:dichloromethane (5:95); NMR (DMSO/D$_2$O): 8.23 (s,1), 7.32 (m,5), 5.10 (s,2), 4.78 (m,2), 4.00 (d,1), 2.75 (m,1), 2.20 (m,1), 1.11 (d,6), 0.88 (d,3), 0.73 (d,3).

Analysis for C$_{23}$H$_{27}$F$_3$N$_4$O$_5$: Calculated: C, 55.6; H, 5.48; N, 11.3. Found: C, 55.6; H, 5.53; N, 11.3.

The intermediate alcohols used in Examples 18-25 were prepared as follows.

EXAMPLES 18.a.-25.a.

Using a procedure similar to that described in Example 8.a., the following imidates of formula IV wherein R$^7$ is ethyl and R$^6$ is the indicated group were prepared from the indicated nitrile, and isolated as their hydrochloride salts.

EXAMPLE 18.a.

R$^6$=4-nitrophenyl, from 4-nitrobenzonitrile. Purification method: trituration from diethyl ether; MS: m/z=195(M+1-HCl).

EXAMPLE 19.a.

R$^6$=4-trifluoromethylphenyl, from 4-trifluoromethylbenzonitrile. Purification method: trituration from diethyl ether; MS: m/z=218(M+1-HCl).

EXAMPLE 20.a.

R$^6$=3,5-difluorophenyl, from 3,5-difluorobenzonitrile. Purification method: trituration from diethyl ether; MS: m/z=186(M+1-HCl).

EXAMPLE 21.a.

R$^6$=4-methoxyphenyl, from 4-methoxybenzonitrile. Purification method: trituration from diethyl ether; MS: m/z=180(M+1-HCl).

EXAMPLE 22.a.

R$^6$=4-chlorophenyl, from 4-chlorobenzonitrile. Purification method: trituration from diethyl ether; MS: m/z=169(M+1-HCl).

EXAMPLE 23.a.

R$^6$=3,5-bis(trifluoromethyl)phenyl, from 3,5-bis(trifluoromethyl)benzonitrile. Purification method: trituration from diethyl ether; MS: m/z=286(M+1-HCl).

EXAMPLE 24.a.

R$^6$=cyclohexyl, from cyclohexanecarbonitrile. Purification method: trituration from diethyl ether; MS: m/z=156(M+1-HCl).

EXAMPLE 25.a.

R$^6$=isopropyl, from isopropylnitrile. Purification method: trituration from diethyl ether; MS: m/z=115(M+1-HCl).

EXAMPLES 18.b.-25.b.

Using a procedure similar to that described in Example 8.b. the following compounds of formula V wherein R$^8$ is dimethoxymethyl and R$^6$ is the indicated group were prepared from the corresponding imidate hydrochlorides of formula IV and aminoacetaldehyde dimethyl acetal.

EXAMPLE 18.b.

R$^6$=4-nitrophenyl; MS: m/z=254(M+1).

EXAMPLE 19.b.

R$^6$=4-trifluoromethylphenyl; MS: m/z=277(M+1).

EXAMPLE 20.b.

R$^6$=3,5-difluorophenyl; MS: m/z=245(M+1)

EXAMPLE 21.b.

R$^6$=4-methoxyphenyl; MS: m/z=239(M+1).

EXAMPLE 22.b.

R$^6$=4-chlorophenyl; MS: m/z=243(M+1).

EXAMPLE 23.b.

R$^6$=3,5-bis(trifluoromethyl)phenyl; MS: m/z=345(M+1).

EXAMPLE 24.b.

R$^6$=cyclohexyl; MS: m/z=215(M+1).

EXAMPLE 25.b.

R$^6$=isopropyl; MS: m/z=175(M+1).

EXAMPLES 18.c.-25.c.

Using a procedure similar to that described in Example 1.b., the following pyrimidone esters of formula VI wherein R$^8$ is dimethoxymethyl and R$^6$ is the indicated group were prepared from the corresponding amidines of formula V and dimethylmethoxy methylenemalonate.

EXAMPLE 18.c.

R$^6$=4-nitrophenyl; yellow solid; TLC: R$_f$=0.3, diethyl ether; MS: m/z=364(M+1).

EXAMPLE 19.c.

$R^6$=4-trifluoromethylphenyl; TLC: $R_f$=0.37, diethyl ether; MS: m/z=387(M+1).

EXAMPLE 20.c.

$R^6$=3,5-difluorophenyl; TLC: $R_f$=0.28, diethyl ether:hexane (80:20); MS: m/z=355(M+1).

EXAMPLE 21.c.

$R^6$=4-methoxyphenyl; TLC: $R_f$=0.37, ethyl acetate; MS: m/z=349(M+1).

EXAMPLE 22.c.

$R^6$=4-chlorophenyl; TLC: $R_f$=0.5, ethyl acetate; MS: m/z=353(M+1).

EXAMPLE 23.c.

$R^6$=3,5-bis(trifluoromethyl)phenyl; TLC: $R_f$=0.6, ethyl acetate; MS: m/z=455(M+1).

EXAMPLE 24.c.

$R^6$=cyclohexyl; TLC: $R_f$=0.6, diethyl ether; MS: m/z=325(M+1).

EXAMPLE 25.c.

$R^6$=2-propyl; TLC: $R_f$=0.35, diethyl ether; MS: m/z=285(M+1).

EXAMPLES 18.d.-25.d.

Using a procedure similar to that described in Example 11.d., the pyrimidone acids of formula VII wherein $R^8$ is dimethoxymethyl and $R^6$ is the indicated group were prepared from the corresponding pyrimidone esters of formula VI.

EXAMPLE 18.d.

$R^6$=4-nitrophenyl; yellow solid; TLC: $R_f$=0.1, ethyl acetate; MS: m/z=350(M+1).

EXAMPLE 19.d.

$R^6$=4-trifluoromethylphenyl; TLC: $R_f$=0.24, methanol:dichloromethane (10:90); MS: m/z=373(M+1).

EXAMPLE 20.d.

$R^6$=3,5-difluorophenyl; TLC: $R_f$=0.40, methanol:dichloromethane (15:85); MS: m/z=341(M+1)

EXAMPLE 21.d.

$R^6$=4-methoxyphenyl; TLC: $R_f$=0.45, methanol:dichloromethane (5:95); MS: m/z=335(M+1).

EXAMPLE 22.d.

$R^6$=4-chlorophenyl; TLC: $R_f$=0.2, methanol:dichloromethane (10:90); MS: m/z=339(M+1).

EXAMPLE 23.d.

$R^6$=3,5-bis(trifluoromethyl)phenyl; TLC: $R_f$=0.3, methanol:dichloromethane (20:80); MS m/z=441(M+1).

EXAMPLE 24.d.

$R^6$=cyclohexyl; TLC: $R_f$=0.2, diethyl ether; MS: m/z=311(M+1).

EXAMPLE 25.d.

$R^6$=2-propyl; TLC: $R_f$=0.8, diethyl ether; MS: m/z=376(M+1).

EXAMPLES 18.e.-25.e.

Using a procedure similar to that described in Example 1.d, the following compounds of formula IX wherein $R^8$ is dimethoxymethyl and $R^6$ is the indicated group were prepared from the corresponding acids of formula VII.

EXAMPLE 18.e.

$R^6$=4-nitrophenyl; white solid; TLC: $R_f$=0.8, ethyl acetate; NMR: 9.08 (s,1), 8.49 (s,1), 8.34 (d,2), 7.85 (d,2), 7.38 (m,5), 5.21 (s,2), 4.51 (t,1), 4.02 (d,2).

EXAMPLE 19.e.

$R^6$=4-trifluoromethylphenyl; TLC: $R_f$=0.36, ethyl acetate:dichloromethane (5:95); MS: m/z=478(M+1).

EXAMPLE 20.e.

$R^6$=3,5-difluorophenyl; TLC: $R_f$=0.74, diethyl ether:hexane (80:20); MS: m/z=446(M+1).

EXAMPLE 21.e.

$R^6$=4-methoxyphenyl; TLC: $R_f$=0.71, ethyl acetate; MS: m/z=440(M+1).

EXAMPLE 22.e.

$R^6$=4-chlorophenyl; TLC: $R_f$=0.8, diethyl ether; MS m/z=444(M+1).

EXAMPLE 23.e.

$R^6$=3,5-bis(trifluoromethyl)phenyl; TLC: $R_f$=0.61, ethyl acetate:dichloromethane (5:95); MS: m/z=546(M+1).

EXAMPLE 24.e.

$R^6$=cyclohexyl; oil; TLC: $R_f$=0.8, diethyl ether; MS: m/z=416(M+1).

EXAMPLE 25.e.

$R^6$=isopropyl; TLC: $R_f$=0.8, diethyl ether; MS: m/z=376(M+1).

EXAMPLES 18.f.-25.f.

Using a procedure similar to that described in Example 8.f., the following aldehydes of formula X wherein $R^6$ is the indicated group were prepared from the corresponding compounds of formula IX.

EXAMPLE 18.f.

$R^6$=4-nitrophenyl; yellow solid; TLC: $R_f$=0.5, diethyl ether; MS: m/z=409(M+1).

EXAMPLE 19.f.

$R^6$=4-trifluoromethylphenyl; TLC: $R_f$=0.27, ethyl acetate:dichloromethane (5:95); MS: m/z=432(M+1).

EXAMPLE 20.f.

$R^6$=3,5-difluorophenyl; TLC: $R_f$=0.38, diethyl ether:hexane (70:30); MS: m/z=400(M+1).

EXAMPLE 21.f.

$R^6$=4-methoxyphenyl; TLC: $R_f$=0.65, ethyl acetate; MS: m/z=394(M+1).

EXAMPLE 22.f.

$R^6$=4-chlorophenyl; TLC: $R_f$=0.5, diethyl ether; MS: m/z=398(M+1).

EXAMPLE 23.f.

$R^6$=3,5-bis(trifluoromethyl)phenyl; TLC: $R_f$=0.72, methanol:dichloromethane (5:95); MS: m/z=500(M+1).

EXAMPLE 24.f.

$R^6$=cyclohexyl; TLC: $R_f$=0.3, ethyl acetate; MS m/z=369(M+1).

EXAMPLE 25.f.

$R^6$=isopropyl; TLC: $R_f$=0.2, diethyl ether; MS: m/z=330(M+1).

EXAMPLES 18.g.–25.g.

Using a procedure similar to that described in Example 1.f., the following acids of formula III wherein $R^6$ is the indicated group were prepared from the corresponding aldehydes of structure X.

EXAMPLE 18.g.

$R^6$=4-nitrophenyl; yellow solid; TLC: $R_f$=0.1, ethyl acetate; MS: m/z=425(M+1).

EXAMPLE 19.g.

$R^6$=4-trifluoromethylphenyl; TLC: $R_f$=0.3, methanol:dichloromethane (20:80); MS: m/z=448(M+1).

EXAMPLE 20.g.

$R^6$=3,5-difluorophenyl; TLC: $R_f$=0.35, methanol:dichloromethane (20:80); MS: m/z=416(M+1).

EXAMPLE 21.g.

$R^6$=4-methoxyphenyl; TLC: $R_f$=0.27, methanol:dichloromethane (20:80); MS: m/z=410(M+1).

EXAMPLE 22.g.

$R^6$=4-chlorophenyl; TLC: $R_f$=0.2, methanol:dichloromethane (10:90); MS: m/z=414(M+1).

EXAMPLE 23.g.

$R^6$=3,5-bis(trifluoromethyl)phenyl; TLC: $R_f$=0.30, methanol:dichloromethane (10:90); MS: m/z=516(M+1).

EXAMPLE 24.g.

$R^6$=cyclohexyl; TLC: $R_f$=0.1, ethyl acetate; MS: m/z=385(M+1).

EXAMPLE 25.g.

$R^6$=isopropyl; TLC: $R_f$=0.2, ethyl acetate; MS: m/z=345(M+1).

EXAMPLES 18.h.–25.h.

Using a procedure similar to that described in Example 1.g., the following alcohols of formula II wherein R is benzyloxycarbonyl and $R^6$ is the indicated group were prepared from the corresponding acids of formula III with exceptions as noted.

EXAMPLE 18.h.

$R^6$=4-nitrophenyl: Purified by chromatography, with methanol:dichloromethane (gradient, 3:97, 10:90) as the eluent, to give a yellow solid; TLC: $R_f$=0.2, methanol:dichloromethane (3:97); MS: m/z=578(M+1).

EXAMPLE 19.h.

$R^6$=4-trifluoromethylphenyl; TLC: $R_f$=0.65, diethyl ether; MS: m/z=601(M+1).

EXAMPLE 20.h.

$R^6$=3,5-difluorophenyl; TLC: $R_f$=0.67, tetrahydrofuran:dichloromethane (15:85); MS: m/z=569(M+1).

EXAMPLE 21.h.

$R^6$=4-methoxyphenyl; TLC: $R_f$=0.63, ethyl acetate; MS: m/z=563(M+1).

EXAMPLE 22.h.

$R^6$=4-chlorophenyl; TLC: $R_f$=0.5, ethyl acetate; MS: m/z=567(M+1).

EXAMPLE 23.h.

$R^6$=3,5-bis(trifluoromethyl)phenyl; TLC: $R_f$=0.61, ethyl acetate; MS: m/z=669(M+1).

EXAMPLE 24.h.

$R^6$=cyclohexyl; TLC: $R_f$=0.6, methanol:dichloromethane (5:95); MS: m/z=539(M+1).

EXAMPLE 25.h.

$R^6$=isopropyl; TLC: $R_f$=0.45, diethyl ether; MS: m/z=499(M+1).

EXAMPLES 26–31

Using a procedure similar to that described in Example 6, the following compounds of formula I wherein $R^0$ is isopropyl, R is hydrogen, and $R^6$ is the indicated group were prepared from the corresponding compounds of formula I wherein R is benzyloxycarbonyl.

EXAMPLE 26

$R^6$=4-trifluoromethylphenyl: Chromatography solvent: ethyl acetate; TLC: $R_f$=0.31, ethyl acetate; NMR (DMSO/D$_2$O): 7.71 (d,2), 7.60 (d,2), 7.35 (s,1), 4.55 (m,2), 4.04 (d,2), 2.14 (m,1), 0.76 (d,3), 0.63 (d,3).

Analysis for $C_{19}H_{18}F_6N_4O_3 \cdot 0.5H_2O$: Calculated: C, 48.2; H, 4.05; N, 11.8. Found: C, 48.1; H, 4.38; N, 11.6.

EXAMPLE 27

$R^6$=3,5-difluorophenyl: Chromatography solvent: methanol:dichloromethane (gradient, 5:95, 12:88); TLC: $R_f$=0.18, tetrahydrofuran:dichloromethane (10:90); 300 MHz NMR (DMSO/D$_2$O): 7.35 (m,1), 7.31 (s,1), 7.14 (m,2), 4.65 (d,1), 4.40 (d,1), 4.02 (m,1), 2.22 (m,1), 0.85 (d,3), 0.74 (d,3).

Analysis for $C_{19}H_{18}F_6N_4O_3 \cdot 0.5H_2O$: Calculated: C, 48.2; H, 4.05; N, 11.8. Found: C, 48.1; H, 4.38; N, 11.6.

EXAMPLE 28

$R^6$=4-methoxyphenyl: Chromatography solvent: ethyl acetate; TLC: $R_f$=0.24, ethyl acetate; NMR (DMSO/D$_2$O): 7.54 (d,2), 7.53 (s,1), 6.91 (d,2), 4.50 (m,2), 4.01 (d,2), 3.76 (s,3), 2.20 (m,1), 0.82 (d,3), 0.75 (d,3).

Analysis for $C_{19}H_{21}F_3N_4O_4$: Calculated: C, 53.5; H, 4.96; N, 13.1. Found: C, 53.5; H, 5.04; N, 13.1.

EXAMPLE 29

$R^6$=isopropyl: NMR (DMSO/D$_2$O): 7.23 (s,1), 4.75 (m,2), 4.03 (d,2), 2.72 (m,1), 2.22 (m,1), 1.06 (d,6), 0.89 (d,3), 0.75 (d,3).

Analysis for $C_{15}H_{21}F_3N_4O_3$: Calculated: C, 49.7; H, 5.84; N, 15.5. Found: C, 49.5; H, 5.84; N, 15.2.

EXAMPLE 30

$R^6$ = 3,5-bis(trifluoromethyl)phenyl: NMR: 8.91 (d,1), 8.24 (s,1), 8.16 (s,2), 7.36 (s,1), 5.44 (s,2), 4.65 (m,3), 2.13 (m,1), 0.83 (d,3), 0.80 (d,3).

Analysis for $C_{20}H_{17}F_9N_4O_3$: Calculated: C, 45.1; H, 3.22; N, 10.5. Found: C, 45.6; H, 3.37; N, 10.7.

EXAMPLE 31

$R^6$ = cyclohexyl: Chromatography solvent: methanol:dichloromethane (5:95); TLC: $R_f$=0.17, methanol:dichloromethane (5:95); NMR (DMSO/D$_2$O): 7.22 (s,1), 4.81 (m,2), 4.02 (d,1), 2.27 (m,2), 1.66 (m,5), 1.38 (m,2), 1.15 (m,3), 0.92 (d,3), 0.78 (d,3).

Analysis for $C_{18}H_{25}F_3N_4O_3 \cdot 0.5H_2O$: Calculated: C, 52.6; H, 6.37; N, 13.6. Found: C, 52.6; H, 6.26; N, 13.5.

EXAMPLES 32–33

Using a procedure similar to that described in Example 12, the following compounds of formula I wherein $R^0$ is isopropyl, R is hydrogen, and $R^6$ is the indicated group were prepared from the corresponding compounds of formula I wherein R is benzyloxycarbonyl.

EXAMPLE 32

$R^6$ = 4-chlorophenyl: Chromatography solvent: methanol:dichloromethane (gradient, 5:95, 20:80); TLC: $R_f$=0.2, methanol:dichloromethane (5:95); NMR (DMSO/D$_2$O): 7.34 (m,5), 4.49 (m,2), 3.99 (d,2), 2.15 (m,1), 0.78 (d,3), 0.67 (d,3).

Analysis for $C_{18}H_{18}ClF_3N_4O_3$: Calculated: C, 50.2; H, 4.21; N, 13.0 Found: C, 50.0; H, 4.44; N, 12.8

EXAMPLE 33

$R^6$ = 4-nitrophenyl: Chromatography solvent: tetrahydrofuran:dichloromethane (gradient, 30:70, 50:50); NMR (DMSO/D$_2$O): 8.21 (d,2), 7.63 (d,2), 7.35 (s,1), 4.49 (m,2), 3.99 (d,2), 2.14 (m,1), 0.76 (d,3), 0.63 (d,3).

Analysis for $C_{18}H_{18}F_3N_5O_5 \cdot 1.1H_2O$: Calculated: C, 46.9; H, 4.41; N, 15.2. Found: C, 46.9; H, 4.25; N, 15.2.

EXAMPLE 34

2-[5-Amino-2-(4-aminophenyl)-6-oxo-1,6-dihydro-1-pyrimidinyl]-N-(3,3,3-trifluoro-1-isopropyl-2-oxopropyl)acetamide 2-[5-Benzyloxycarbonylamino-2-(4-nitrophenyl)-6-oxo-1,6-dihydro-1-pyrimidinyl]-N-(3,3,3-trifluoro-1-isopropyl-2-oxopropyl)acetamide was subjected to a procedure similar to that described in Example 6 to give a brown solid; chromatography solvent: methanol:dichloromethane (gradient, 5:95, 10:90); NMR (DMSO/D$_2$O): 7.29 (s,1), 7.01 (d,2), 6.49 (d,2), 4.52 (m,2), 4.10 (d,2), 2.25 (m,1), 0.88 (d,3), 0.80 (d,3).

Analysis for $C_{18}H_{20}F_3N_5O_3$: Calculated: C, 52.6; H, 4.90; N, 17.0. Found: C, 52.4; H, 4.96; N, 16.7.

EXAMPLE 35

2-[5-Acetylamino-6-oxo-2-(2-thienyl)-1,6-dihydro-1-pyrimidinyl]-N-(3,3,3-trifluoro-1-isopropyl-2-oxopropyl)acetamide To a solution of 2-[5-amino-6-oxo-2-(2-thienyl)-1,6-dihydro-1-pyrimidinyl]-N-(3,3,3-trifluoro-1-isopropyl-2-oxopropyl)acetamide (0.3 g) in tetrahydrofuran (7 mL) was added sodium carbonate (0.4 g) and the mixture cooled in an ice bath to 0° C. Acetyl chloride (0.11 mL) was added and the solution warmed to room temperature and let stir for 1 h. The mixture was poured into ethyl acetate and washed (1N HCl, a saturated solution of sodium carbonate, and H$_2$O). The resulting solution was dried and the solvent removed by evaporation. The resulting material was purified by chromatography, eluting with methanol:dichloromethane (gradient, 5:95, 12:88) to give the title compound (0.46 g) as a light yellow powder; TLC: $R_f$=0.47, methanol:dichloromethane (5:95); NMR (DMSO/D$_2$O): 8.77 (s,1), 7.81 (d,1), 7.36 (d,1), 7.09 (t,1), 4.83 (m,2), 4.09 (d,1), 2.26 (m,1), 2.13 (s,3), 0.93 (d,3), 0.80 (d,3).

Analysis for $C_{18}H_{19}F_3N_4O_4S \cdot 0.25H_2O$: Calculated: C, 48.2; H, 4.38; N, 12.5. Found: C, 48.0; H, 4.35; N, 12.4.

This procedure will be referred to as Acylation Method A.

EXAMPLES 36–74

The following compounds of formula I wherein $R^0$ is isopropyl and R and $R^6$ have the indicated values were prepared from the corresponding compounds of formula I wherein R is hydrogen using Acylation Method A and the required acyl chloride.

EXAMPLE 36

R=acetyl, $R^6$=4-fluorophenyl; chromatography solvent: methanol:dichloromethane (gradient, 0:100, 7:93); TLC: $R_f$=0.27, ethyl acetate:dichloromethane (35:65); NMR (DMSO/D$_2$O): 9.51 (s,1), 8.8 (s,1), 7.55 (m,2), 7.26 (m,2), 4.66 (broad d,1), 4.52 (m,2), 4.01 (d,1), 2.24 (m,1), 2.14 (s,3), 0.85 (d,3), 0.75 (d,3).

Analysis for $C_{20}H_{20}F_4N_4O_4 \cdot 1.0H_2O$: Calculated: C, 50.6; H, 4.67; N, 11.8. Found: C, 50.4; H, 4.63; N, 11.8.

EXAMPLE 37

R=acetyl, $R^6$=3-pyridyl; tan solid; chromatography solvent: methanol:dichloromethane (gradient, 5:95, 10:90); TLC: $R_f$=0.4, methanol:dichloromethane (10:90); 300 MHz NMR (DMSO/D$_2$O): 8.58 (m,2), 7.81 (m,1), 7.40 (m,1), 7.34 (s,1), 4.59 (m,2), 3.98 (d,1), 2.16 (m,1), 0.90 (d,3), 0.68 (d,3).

Analysis for $C_{19}H_{20}F_3N_5O_4 \cdot 0.7H_2O$: Calculated: C, 50.5; H, 4.77; N, 15.5. Found: C, 50.6; H, 4.75; N, 15.3.

EXAMPLE 38

R=methoxycarbonyl, $R^6$=3-pyridyl; white solid; purified by trituration from diethyl ether:hexane (50:50); TLC: $R_f$=0.6, methanol:dichloromethane (10:90); NMR (DMSO/D$_2$O): 8.62 (m,2), 8.44 (s,1), 7.86 (m,1), 4.62 (m,2), 3.95 (d,1), 3.66 (s,3), 2.15 (m,1), 0.78 (d,3), 0.64 (d,3).

Analysis for $C_{19}H_{20}F_3N_5O_5 \cdot 1.0H_2O$: Calculated: C, 48.2; H, 4.68; N, 14.8. Found: C, 48.5; H, 4.87; N, 14.2.

EXAMPLE 39

R=4-methoxyphenoxycarbonyl, $R^6$=3-pyridyl; white solid; chromatography solvent: methanol:dichloromethane (5:95); TLC: $R_f$=0.4, methanol:dichloromethane (7:93); 300 MHz NMR (DMSO/D$_2$O): 8.65 (m,2), 8.43 (s,1), 7.88 (m,1), 7.44 (m,1), 7.10 (d,2), 6.92 (d,2), 4.55 (m,2), 3.97 (d,1), 3.62 (s,3), 2.17 (m,1), 0.78 (d,3), 0.67 (d,3).

Analysis for $C_{25}H_{24}F_3N_5O_6$: Calculated: C, 54.8; H, 4.41; N, 12.8. Found: C, 54.2; H, 4.43; N, 12.5.

EXAMPLE 40

R=methoxycarbonyl, $R^6$=4-methoxyphenyl; white solid; purified by recrystallization from ethyl acetate; TLC: $R_f$=0.46, ethyl acetate; NMR (DMSO/$D_2O$): 8.85 (d,1), 8.79 (s,1), 7.42 (d,2), 6.99 (d,2), 4.66 (t,1), 4.58 (dd,1), 3.81 (s,1), 3.68 (s,3), 2.16 (m,1), 0.90 (d,3), 0.84 (d,3).

Analysis for $C_{21}H_{23}F_3N_4O_6$: Calculated: C, 52.1; H, 4.79; N, 11.6. Found: C, 51.9; H, 4.82; N, 11.5.

EXAMPLE 41

R=4-fluorophenoxycarbonyl, $R^6$=phenyl; white solid; chromatography solvent: ethyl acetate:dichloromethane (gradient, 25:75, 40:60); TLC: $R_f$=0.8, tetrahydrofuran:dichloromethane (20:80); NMR (DMSO/$D_2O$): 8.42 (s,1), 7.48 (m,5), 7.25 (d,4), 4.65 (d,1), 4.48 (d,1), 4.05 (d,1), 2.23 (m,1), 0.85 (d,3), 0.77 (d,3).

Analysis for $C_{25}H_{22}F_4N_4O_5$: Calculated: C, 56.2; H, 4.15; N, 10.5. Found: C, 56.3; H, 4.31; N, 10.4.

EXAMPLE 42

R=methoxycarbonyl, $R^6$=phenyl; white solid; chromatography solvent: tetrahydrofuran:dichloromethane (gradient, 5:95 to 20:80); TLC: $R_f$=0.38, tetrahydrofuran:dichloromethane (10:90); NMR (DMSO/$D_2O$): 8.79 (d,1), 8.43 (s,1), 7.49 (m,5), 4.60 (m,2), 4.02 (s,1), 3.67 (s,3), 2.23 (m,1), 0.80 (overlaping d,6).

Analysis for $C_{20}H_{21}F_3N_4O_5$: Calculated: C, 52.9; H, 4.66; N, 12.3. Found: C, 52.8; H, 4.65; N, 12.3.

EXAMPLE 43

R=methoxycarbonyl, $R^6$=4-fluorophenyl; white solid; chromatography solvent: methanol:dichloromethane (5:95); TLC: $R_f$=0.37, methanol:dichloromethane (5:95); NMR: 8.88 (s,1), 8.83 (s,1), 8.44 (s,1), 7.53 (dd,2), 7.31 (dd,2), 4.64 (t,1), 4.57 (dd,2), 3.66 (s,3), 2.15 (m,1), 0.87 (d,3), 0.82 (d,3).

Analysis for $C_{20}H_{20}F_4N_4O_5$: Calculated: C, 50.9; H, 4.27; N, 11.9. Found: C, 51.0; H, 4.32; N, 11.9.

EXAMPLE 44

R=methoxycarbonyl, $R^6$=4-chlorophenyl; white solid; chromatography solvent: methanol:dichloromethane (5:95); TLC: $R_f$=0.41, methanol:dichloromethane (5:95); NMR: 8.88 (s,1), 8.83 (d,1), 8.45 (s,1), 7.54 (d,2), 7.49 (d,2), 4.64 (t,1), 4.57 (dd,2), 3.68 (s,3), 2.15 (m,1), 0.88 (d,3), 0.81 (d,3).

Analysis for $C_{20}H_{20}ClF_3N_4O_5$: Calculated: C, 49.1; H, 4.12; N, 11.4. Found: C, 48.8; H, 4.16; N, 11.3.

EXAMPLE 45

R=cyclopentyloxycarbonyl, $R^6$=4-fluorophenyl; using cyclopentyl chloroformate; white solid; chromatography solvent; methanol:dichloromethane (5:95); NMR: 8.84 (d,1), 8.53 (s,1), 8.42 (s,1), 7.53 (dd,2), 7.31 (dd,2), 5.10 (m,1), 4.58 (m,3), 2.14 (m,1), 1.61 (m,8), 0.68 (d,3), 0.62 (d,3).

Analysis for $C_{24}H_{26}F_4N_4O_5$: Calculated: C, 54.8; H, 4.98; N, 10.6. Found: C, 54.6; H, 4.97; N, 10.5.

EXAMPLE 46

R=cyclopentyloxycarbonyl, $R^6$=4-chlorophenyl; using cyclopentyl chloroformate; white solid; chromatography solvent: methanol:dichloromethane (5:95); TLC: $R_f$=0.45, methanol:dichloromethane (5:95); NMR: 8.85 (d,1), 8.53 (s,1), 8.43 (s,1), 7.55 (d,2), 7.49 (d,2), 5.10 (m,1), 4.65 (t,1), 4.58 (dd,2), 2.16 (m,1), 1.71 (m,8), 0.88 (d,3), 0.83 (d,3).

Analysis for $C_{24}H_{26}ClF_3N_4O_5$: Calculated: C, 53.1; H, 4.83; N, 10.3. Found: C, 53.1; H, 4.88; N, 10.2.

EXAMPLE 47

R=cyclopentyloxycarbonyl, $R^6$=phenyl; white solid; chromatography solvent: methanol:dichloromethane (5:95); TLC: $R_f$=0.35, methanol:dichloromethane (5:95); NMR: 8.84 (d,1), 8.52 (s,1), 8.43 (s,1), 7.48 (m,5), 5.10 (m,1), 4.67 (t,1), 4.55 (dd,2), 2.16 (m,1), 1.71 (m,8), 0.89 (d,3), 0.83 (d,3).

Analysis for $C_{24}H_{27}F_3N_4O_5$: Calculated: C, 56.7; H, 5.35; N, 11.0. Found: C, 56.7; H, 5.49; N, 10.9.

EXAMPLE 48

R=isopropoxycarbonyl, $R^6$=phenyl; white solid; chromatography solvent: methanol:dichloromethane (5:95); TLC: $R_f$=0.38, methanol:dichloromethane (5:95); NMR (DMSO/$D_2O$): 8.39 (s,1), 7.43 (m,5), 4.85 (m,1), 4.52 (dd,2), 4.00 (d,1), 2.19 (m,1), 1.22 (d,6), 0.81 (d,3), 0.73 (d,3).

Analysis for $C_{22}H_{25}F_3N_4O_5 \cdot 0.1H_2O$: Calculated: C, 54.7; H, 5.27; N, 11.5. Found: C, 54.2; H, 5.50; N, 11.2.

EXAMPLE 49

R=isopropoxycarbonyl, $R^6$=4-fluorophenyl; white solid; chromatography solvent: methanol:dichloromethane (5:95); TLC: $R_f$=0.33, methanol:dichloromethane (5:95); 300 MHz NMR (DMSO/$D_2O$): 8.38 (s,1), 7.50 (dd,2), 7.23 (t,2), 4.86 (m,1), 4.55 (dd,2), 3.98 (d,1), 2.15 (m,1), 1.22 (d,6), 0.80 (d,3), 0.70 (d,3).

Analysis for $C_{22}H_{24}F_4N_4O_5 \cdot 0.5H_2O$: Calculated: C, 51.9; H, 4.95; N, 11.0. Found: C, 51.9; H, 4.95; N, 10.8.

EXAMPLE 50

R=cyclopentyloxycarbonyl, $R^6$=2-thienyl; white solid; chromatography solvent: ethyl acetate:dichloromethane (15:85); TLC: $R_f$=0.28, ethyl acetate:dichloromethane (15:85); NMR (DMSO/$D_2O$): 8.40 (s,1), 7.79 (d,1), 7.38 (d,1), 7.13 (t,1), 5.09 (m,1), 4.88 (dd,2), 4.09 (d,1), 2.27 (m,1), 1.68 (m,8), 0.93 (d,3), 0.79 (d,3).

Analysis for $C_{22}H_{25}F_3N_4O_5S$: Calculated: C, 51.4; H, 4.90; N, 10.9. Found: C, 51.1; H, 4.93; N, 10.8.

EXAMPLE 51

R=isopropoxycarbonyl, $R^6$=2-thienyl; white solid; chromatography solvent: ethyl acetate:dichloromethane (15:85); TLC: $R_f$=0.22, ethyl acetate:dichloromethane (15:85); NMR (DMSO/$D_2O$): 8.41 (s,1), 7.79 (d,1), 7.39 (d,1), 7.14 (t,1), 4.87 (m,2), 4.09 (d,1), 2.27 (m,1), 1.26 (d,6), 0.94 (d,3), 0.79 (d,3).

Analysis for $C_{20}H_{23}F_3N_4O_5S$: Calculated: C, 49.2; H, 4.75; N, 11.4. Found: C, 49.1; H, 4.76; N, 11.4.

EXAMPLE 52

R=methoxycarbonyl, $R^6$=2-thienyl; white solid; chromatography solvent: methanol:dichloromethane (5:95); TLC: $R_f$=0.31, methanol:dichloromethane (5:95); 300 MHz NMR (DMSO/$D_2O$): 8.43 (s,1), 7.79 (d,1), 7.39 (d,1), 7.13 (dd,1), 4.88 (dd,2), 4.09 (d,1), 3.70 (s,3), 2.29 (m,1), 0.93 (d,3), 0.79 (d,3).

Analysis for $C_{18}H_{19}F_3N_4O_5S$: Calculated: C, 47.0; H, 4.16; N, 12.2. Found: C, 46.7; H, 4.16; N, 12.1.

EXAMPLE 53

R=isopropoxycarbonyl, $R^6$=4-chlorophenyl; white solid; chromatography solvent: ethyl acetate:dichloromethane (gradient, 10:90, 15:85); TLC: $R_f$=0.43, methanol:dichloromethane (5:95); NMR (DMSO/D$_2$O): 8.44 (s,1), 7.51 (m,4), 4.90 (m,1), 4.60 (dd,2), 4.02 (d,1), 2.22 (m,1), 1.26 (d,6), 0.85 (d,3), 0.73 (d,3).

Analysis for $C_{22}H_{24}ClF_3N_4O_5 \cdot 0.75H_2O$: Calculated: C, 49.8; H, 4.85; N, 10.6. Found: C, 50.1; H, 4.73; N, 10.5.

EXAMPLE 54

R=cyclopentyloxycarbonyl, $R^6$=4-methoxyphenyl; white solid; chromatography solvent: methanol:dichloromethane (5:95); TLC: $R_f$=0.31, methanol:dichloromethane (5:95); NMR (DMSO/D$_2$O): 8.40 (s,1), 7.44 (d,2), 6.99 (d,2), 5.09 (m,1), 4.60 (dd,2), 4.04 (d,1), 3.81 (s,3), 2.23 (m,1), 1.69 (m,8), 0.77 (d,3), 0.66 (d,3).

Analysis for $C_{25}H_{29}F_3N_4O_6$: Calculated: C, 55.8; H, 5.43; N, 10.4. Found: C, 55.8; H, 5.52; N, 10.4.

EXAMPLE 55

R=isopropoxycarbonyl, $R^6$=4-methoxyphenyl; white solid; chromatography solvent: methanol:dichloromethane (5:95); TLC: $R_f$=0.28, methanol:dichloromethane (5:95); NMR (DMSO/D$_2$O): 8.42 (s,1), 7.46 (d,2), 7.00 (d,2), 4.91 (m,1), 4.68 (dd,2), 4.07 (d,1), 3.82 (s,3), 2.25 (m,1), 1.28 (d,6), 0.87 (d,3), 0.79 (d,3).

Analysis for $C_{23}H_{27}F_3N_4O_6$: Calculated: C, 53.9; H, 5.31; N, 10.9. Found: C, 54.1; H, 5.43; N, 10.

EXAMPLE 56

R=4-fluorobenzyloxycarbonyl, $R^6$=4-methoxyphenyl; white solid; chromatography solvent: methanol:dichloromethane (5:95) TLC: $R_f$=0.22, methanol:dichloromethane (5:95); NMR (DMSO/D$_2$O): 8.37 (s,1), 7.41 (m,4), 7.18 (t,2), 6.93 (d,2), 5.64 (m,2), 5.11 (s,2), 4.00 (d,1), 3.75 (s,3), 2.18 (m,1), 0.81 (d,3), 0.72 (d,3).

Analysis for $C_{27}H_{26}F_4N_4O_6$: Calculated: C, 56.1; H, 4.53; N, 9.68. Found: C, 56.0; H, 4.62; N, 9.51.

The intermediate 4-fluorobenzyloxy chloroformate was prepared as follows.

To a solution of triphosgene (0.53 g) in diethyl ether (2 mL) which had been cooled to 0° C. was added 4-fluorobenzyl alcohol (0.63 g) and quinoline (0.65 g). The solution was allowed to stir for for 5 minutes and then additional ether was added (2 mL). A solid separated from solution and was removed by filtration. The solvent was evaporated and the resulting oil was then used without further purification.

EXAMPLE 57

R=4-fluorobenzyloxycarbonyl, $R^6$=phenyl; white solid; chromatography solvent: ethyl acetate:dichloromethane (25:75); TLC: $R_f$=0.41, ethyl acetate:dichloromethane (25:75); 300 MHz NMR: 9.01 (s,1), 8.83 (d,1), 8.45 (s,1), 7.48 (m,7), 7.22 (t,2), 5.17 (s,2), 4.66 (t,1), 4.55 (dd,2), 2.15 (m,1), 0.89 (d,3), 0.82 (d,3).

Analysis for $C_{26}H_{24}F_4N_4O_5$: Calculated: C, 57.0; H, 4.41; N, 10.2. Found: C, 56.9; H, 4.39; N, 10.2.

EXAMPLE 58

R=4-fluorobenzyloxycarbonyl, $R^6$=4-chlorophenyl; white solid; chromatography solvent: ethyl acetate:dichloromethane (25:75); TLC: $R_f$=0.46, ethyl acetate:dichloromethane (25:75); 300 MHz NMR: 9.03 (s,1), 8.84 (d,1), 8.45 (s,1), 7.52 (m,6), 7.27 (t,2), 5.17 (s,2), 4.64 (t,1), 4.58 (dd,2), 2.15 (m,1), 0.88 (d,3), 0.82 (d,3).

Analysis for $C_{26}H_{23}ClF_4N_4O_5$: Calculated: C, 53.6; H, 3.97; N, 9.61. Found: C, 53.7; H, 4.09; N, 9.56.

EXAMPLE 59

R=4-fluorobenzyloxycarbonyl, $R^6$=4-fluorophenyl; white solid; chromatography solvent: ethyl acetate:dichloromethane (25:75); TLC: $R_f$=0.39, ethyl acetate:dichloromethane (25:75); 300 MHz NMR: 9.02 (s,1), 8.84 (d,1), 8.45 (s,1), 7.51 (m,4), 7.32 (t,2), 5.17 (s,2), 4.65 (t,1), 4.57 (dd,2), 2.15 (m,1), 0.88 (d,3), 0.82 (d,3).

Analysis for $C_{26}H_{23}F_5N_4O_5$: Calculated: C, 55.1; H, 4.09; N, 9.89. Found: C, 55.0; H, 4.04; N, 9.83.

EXAMPLE 60

R=4-fluorobenzyloxycarbonyl, $R^6$=2-thienyl; white solid; chromatography solvent: ethyl acetate:dichloromethane (25:75); TLC: $R_f$=0.51, ethyl acetate:dichloromethane (25:75); 300 MHz NMR: 9.04 (d,1), 9.03 (s,1), 8.43 (s,1), 7.85 (d,1), 7.50 (t,2), 7.33 (d,1), 7.18 (m,3), 5.19 (s,2), 4.88 (dd,2), 4.75 (t,1), 2.22 (m,1), 0.94 (d,3), 0.91 (d,3).

Analysis for $C_{24}H_{22}F_4N_4O_5S$: Calculated: C, 52.0; H, 4.00; N, 10.1. Found: C, 51.7; H, 3.96; N, 10.0.

EXAMPLE 61

R=ethoxycarbonyl, $R^6$=phenyl; white solid; chromatography solvent: ethyl acetate:dichloromethane (25:75); TLC: $R_f$=0.32, methanol:dichloromethane (5:95); 300 MHz NMR: 8.83 (d,1), 8.67 (s,1), 8.44 (s,1), 7.48 (m,5), 4.64 (m,1), 4.55 (dd,2), 4.15 (m,2), 2.16 (m,1), 1.24 (t,3), 0.89 (d,3), 0.83 (d,3).

Analysis for $C_{21}H_{23}F_3N_4O_5$: Calculated: C, 53.9; H, 4.95; N, 12.0. Found: C, 53.8; H, 4.97; N, 11.9.

EXAMPLE 62

R=ethoxycarbonyl, $R^6$=4-methoxyphenyl; white solid; chromatography solvent: methanol:dichloromethane (5:95); TLC: $R_f$=0.29, methanol:dichloromethane (5:95); 300 MHz NMR: 8.85 (d,1), 8.62 (s,1), 8.41 (s,1), 7.42 (d,2), 7.00 (d,2), 4.66 (m,1), 4.58 (m,2), 4.14 (q,2), 3.81 (s,3), 2.17 (m,1), 1.23 (t,3), 0.90 (d,3), 0.84 (d,3).

Analysis for $C_{22}H_{25}F_3N_4O_6$: Calculated: C, 53.0; H, 5.06 N, 11.2. Found: C, 53.0; H, 5.08; N, 11.2.

EXAMPLE 63

R=ethoxycarbonyl, $R^6$=4-trifluoromethylphenyl; white solid; chromatography solvent: methanol:dichloromethane (5:95); TLC: $R_f$=0.36, methanol:dichloromethane (5:95); 300 MHz NMR: 8.80 (d,1), 8.75 (s,1), 8.46 (s,1), 7.85 (d,2), 7.70 (d,2), 4.60 (m,3), 4.15 (q,2), 2.13 (m,1), 1.24 (t,3), 0.84 (d,3), 0.77 (d,3).

Analysis for $C_{22}H_{22}F_6N_4O_5$: Calculated: C, 49.3; H, 4.13; N, 10.4. Found: C, 49.3; H, 4.23; N, 10.4.

EXAMPLE 64

R=ethoxycarbonyl, $R^6$=3,5-difluorophenyl; yellow solid; chromatography solvent: methanol:dichloromethane (5:95); TLC: $R_f$=0.33, methanol:dichloromethane (5:95); NMR (DMSO/D$_2$O): 8.39 (s,1), 7.35 (m,1), 7.14 (d,2), 4.52 (dd,2), 4.10 (q,2), 3.97 (d,1), 2.17 (m,1), 1.19 (t,3), 0.79 (d,3), 0.69 (d,3).

Analysis for $C_{21}H_{21}F_5N_4O_5$: Calculated: C, 50.0; H, 4.20; N, 11.1. Found: C, 49.7; H, 4.38; N, 10.9.

EXAMPLE 65

R=ethoxycarbonyl, $R^6$=4-fluorophenyl; white solid; chromatography solvent: methanol:dichloromethane (5:95); TLC: $R_f$=0.28, methanol:dichloromethane (5:95); NMR (DMSO/D$_2$): 8.44 (s,1), 7.53 (dd,2), 7.27 (dd,2), 4.58 (dd,2), 4.16 (q,2), 4.00 (d,1), 2.21 (m,1), 1.25 (t,3), 0.84 (d,3), 0.74 (d,3).

Analysis for $C_{21}H_{22}F_4N_4O_5$: Calculated: C, 51.9; H, 4.56; N, 11.5. Found: C, 51.8; H, 4.55; N, 11.5.

EXAMPLE 66

R=isobutoxycarbonyl, $R^6$=2-thienyl; yellow solid; chromatography solvent: methanol:dichloromethane (5:95); TLC: $R_f$=0.40, methanol:dichloromethane (5:95); NMR: 9.03 (d,1), 8.77 (s,1), 8.41 (s,1), 7.83 (d,1), 7.32 (d,1), 7.15 (t,1), 4.86 (dd,2), 4.74 (m,1), 3.87 (d,2), 2.20 (m,1), 1.90 (m,1), 0.91 (m,12).

Analysis for $C_{21}H_{25}F_3N_4O_5S$: Calculated: C, 50.2; H, 5.01; N, 11.2. Found: C, 50.3; H, 5.06; N, 10.9.

EXAMPLE 67

R=ethoxycarbonyl, $R^6$=2-thienyl; yellow solid; chromatography solvent: methanol:dichloromethane (5:95); TLC: $R_f$=0.21, methanol:dichloromethane (5:95); NMR: 9.03 (d,1), 8.70 (s,1), 8.40 (s,1), 7.84 (d,1), 7.32 (d,1), 7.15 (dd,1), 4.86 (dd,2), 4.73 (t,1), 4.14 (q,2), 2.21 (m,1), 1.22 (t,3), 0.93 (d,3), 0.89 (d,3).

Analysis for $C_{19}H_{21}F_3N_4O_5S$: Calculated: C, 48.1; H, 4.46; N, 11.8. Found: C, 48.1; H, 4.54; N, 11.8.

EXAMPLE 68

R=isopropoxycarbonyl, $R^6$=4-trifluoromethylphenyl; yellow solid; chromatography solvent: methanol:dichloromethane (5:95); TLC: $R_f$=0.36, methanol:dichloromethane (5:95); NMR: 8.81 (d,1), 8.59 (s,1), 8.45 (s,1), 7.85 (d,2), 7.70 (d,2), 4.90 (m,1), 4.62 (m,3), 2.13 (m,1), 1.26 (d,6), 0.84 (d,3), 0.78 (d,3).

Analysis for $C_{23}H_{24}F_6N_4O_5S$: Calculated: C, 50.2; H, 4.39; N, 10.2. Found: C, 50.1; H, 4.55; N, 9.96.

EXAMPLE 69

R=2-methoxyethoxycarbonyl, $R^6$=3,5-difluorophenyl; white solid; chromatography solvent: methanol:dichloromethane (5:95); TLC: $R_f$=0.33, methanol:dichloromethane (5:95); 300 MHz NMR: 8.89 (d,1), 8.42 (s,1), 7.49 (t,1), 7.23 (d,2), 4.68 (m,1), 4.52 (dd,2), 4.23 (t,2), 3.56 (t,2), 3.29 (s,3), 2.16 (m,1), 0.88 (d,3), 0.83 (d,3).

Analysis for $C_{22}H_{23}F_5N_4O_6$: Calculated: C, 49.4; H, 4.34; N, 10.5. Found: C, 49.1; H, 4.29; N, 10.4.

EXAMPLE 70

R=2-methoxyethoxycarbonyl, $R^6$=phenyl; white solid; chromatography solvent: methanol:dichloromethane (5:95); TLC: $R_f$=0.26, methanol:dichloromethane (5:95); 300 MHz NMR: 8.83 (d,1), 8.77 (s,1), 8.42 (s,1), 7.50 (m,5), 4.67 (t,1), 4.55 (dd,2), 4.23 (t,2), 3.57 (t,2), 3.29 (s,3), 2.16 (m,1), 0.89 (d,3), 0.83 (d,3).

Analysis for $C_{22}H_{25}F_3N_4O_6$: Calculated: C, 53.0; H, 5.06; N, 11.2. Found: C, 53.0; H, 5.02; N, 11.2.

EXAMPLE 71

R=2-methoxyethoxycarbonyl, $R^6$=4-methoxyphenyl; white solid; chromatography solvent: methanol:dichloromethane (5:95); TLC: $R_f$=0.20, methanol:dichloromethane (5:95); 300 MHz NMR: 8.87 (d,1), 8.74 (s,1), 8.40 (s,1), 7.44 (d,2), 7.02 (d,2), 4.68 (t,1), 4.60 (dd,2), 4.24 (t,2), 3.83 (s,3), 3.58 (t,2), 3.30 (s,3), 2.18 (m,1), 0.91 (d,3), 0.86 (d,3).

Analysis for $C_{23}H_{27}F_3N_4O_7$: Calculated: C, 52.3; H, 5.15; N, 10.6. Found: C, 52.0; H, 5.13; N, 10.5.

EXAMPLE 72

R=isopropoxycarbonyl, $R^6$=3,5-difluorophenyl; white solid; chromatography solvent: methanol:dichloromethane (2.5:97.5); TLC: $R_f$=0.31, methanol:dichloromethane (5:95); NMR: 8.89 (d,1), 8.60 (s,1), 8.43 (s,1), 7.49 (t,1), 7.22 (d,2), 4.90 (m,1), 4.64 (m,3), 2.17 (m,1), 1.25 (d,6), 0.87 (d,3), 0.82 (d,3).

Analysis for $C_{22}H_{23}F_5N_4O_5$: Calculated: C, 51.0; H, 4.47; N, 10.8. Found: C, 50.7; H, 4.44; N, 10.7.

EXAMPLE 73

R=2-methoxyethoxycarbonyl, $R^6$=2-thienyl; yellow solid; chromatography solvent: methanol:dichloromethane (5:95); TLC: $R_f$=0.37, methanol:dichloromethane (5:95); 300 MHz NMR: 9.04 (d,1), 8.80 (s,1), 8.39 (s,1), 7.85 (d,1), 7.33 (d,1), 7.16 (t,1), 4.88 (dd,2), 4.74 (t,1), 4.22 (t,2), 3.56 (t,2), 3.28 (s,3), 2.21 (m,1), 0.94 (d,3), 0.90 (d,3).

Analysis for $C_{20}H_{23}F_3N_4O_6S$: Calculated: C, 47.6; H, 4.60; N, 11.1. Found: C, 47.7; H, 4.61; N, 10.9.

EXAMPLE 74

R=2-methoxyethoxycarbonyl, $R^6$=4-fluorophenyl; white solid; chromatography solvent: methanol:dichloromethane (5:95); TLC: $R_f$=0.34, methanol:dichloromethane (5:95); 300 MHz NMR: 8.86 (d,1), 8.81 (s,1), 8.41 (s,1), 7.54 (m,2), 7.33 (t,2), 4.60 (m,3), 4.24 (m,2), 3.57 (m,2), 3.29 (s,3), 2.16 (m,1), 0.89 (d,3), 0.83 (d,3).

Analysis for $C_{22}H_{24}F_3N_4O_6$: Calculated: C, 51.2; H, 4.68; N, 10.9. Found: C, 51.1; H, 4.67; N, 10.9.

EXAMPLE 75

2-[5-Trifluoroacetylamino-2-(4-fluorophenyl)-6-oxo-1,6-dihydro-1-pyrimidinyl]-N-(3,3,3-trifluoro-1-isopropyl-2-oxopropyl)acetamide To a cooled (−5° C.) solution of the product of Example 15 (0.104 g) in dichloromethane was added trifluoroacetic anhydride (50 μL). The reaction mixture was allowed to warm to room temperature. After 1 h a further charge of trifluoroacetic anhydride (25 μL) was made. After stirring for 1 h, the mixture was evaporated and the residue was purified by chromatography, eluting with dichloromethane:methanol (gradient, 99.5:0.5, 98.5:1.5) to afford the title compound; TLC: $R_f$=0.44, dichloromethane:methanol (98:2); NMR: 0.7–1.0 (m,6), 2.03–2.30 (m,1), 3.97–4.80 (m,3), 7.23–7.40 (m,2), 7.53–7.70 (m,2), 8.43 (s,1), 8.87 (d,1), 10.96 (s,1);

MS: m/z=511(M+1).

Analysis for $C_{20}H_{17}F_7N_4O_4 \cdot 0.5\ H_2O$: Calculated: C, 46.25; H, 3.49; N, 10.78. Found: C, 46.22; H, 3.57; N, 10.62.

EXAMPLES 76–79

Using procedures similar to that described in Example 75, the following compounds of formula I wherein $R^O$ is isopropyl, R is trifluoroacetyl and $R^6$ is the indicated group were prepared from the corresponding compounds of formula I wherein R is hydrogen, with exceptions as noted.

EXAMPLE 76

$R^6$=phenyl: Chromatography solvent: dichloromethane:methanol (gradient, 99.5:0.5, 98.5:1.5); TLC: $R_f$=0.40, dichloromethane:methanol (98:2); NMR: 0.7–0.97 (m,6), 2.07–2.33 (m,1), 4.00–4.77 (m,3), 7.40–7.67 (m,5), 8.45 (s,1), 8.86 (d,1), 10.96 (d,1); MS: m/z=493(M+1).

Analysis for $C_{20}H_{18}F_6N_4O_4.0.6\ H_2O$: Calculated: C, 47.74; H, 3.84; N, 11.13. Found: C, 47.69; H, 3.83; N, 10.91.

EXAMPLE 77

$R^6$=4-methoxyphenyl: Chromatography solvent: dichloromethane:methanol (gradient, 99.5:0.5, 98.5:1.5); TLC: $R_f$=0.52, dichloromethane:methanol (98:2); NMR: 0.70–0.97 (m,6), 2.03–2.27 (m,1), 3.81 (s,3), 4.00–4.77 (m,3), 6.97–7.07 (m,2), 7.47–7.57 (m,2), 8.40 (s,1), 8.88 (d,1), 10.92 (d,1);

MS: m/z=523(M+1).

Analysis for $C_{21}H_{20}F_6N_4O_5.0.6\ H_2O$: Calculated: C, 47.30; H, 4.00; N, 10.50. Found: C, 47.27; H, 4.00; N, 10.32.

EXAMPLE 78

$R^6$=2-thienyl: Omitting the second addition of trifluoroacetic anhydride and stirring overnight: Chromatography solvent: dichloromethane:methanol (gradient, 99.5:0.5, 99.2:0.8); TLC: $R_f$=0.44, dichloromethane:methanol (98:2); NMR: 0.83–1.0 (m,6), 2.20–2.30 (m,1), 4.73–5.03 (m,3), 7.10–8.47 (m,4), 9.06 (d,1), 10.90 (d,1); MS: m/z=499(M+1).

Analysis for $C_{18}H_{16}F_6N_4O_4S$: Calculated: C, 43.37; H, 3.23; N, 11.24. Found: C, 43.20; H, 3.57; N, 11.12.

EXAMPLE 79

$R^6$=3,5-difluorophenyl: Omitting the second addition of trifluoroacetic anhydride and stirring overnight: Chromatography solvent: dichloromethane:methanol (gradient, 99.5:0.5, 99:1); TLC: $R_f$=0.46, dichloromethane:methanol (98:2); NMR: 0.83–0.97 (m,6), 2.10–2.30 (m,1), 4.43–4.80 (m,3), 7.27–7.37 (m,2), 7.47–7.60 (m,1), 8.44 (s,1), 8.90 (d,1), 11.03 (d,1); MS: m/z=529(M+1).

Analysis for $C_{20}H_{16}F_8N_4O_4$: Calculated: C, 45.46; H, 3.05; N, 10.60. Found: C, 45.51; H, 3.25; N, 10.44.

EXAMPLE 80

2-[5-Ethylamino-2-(4-fluorophenyl)-6-oxo-1,6-dihydro-1-pyrimidinyl]-N-(3,3,3-trifluoro-1-isopropyl-2-oxopropyl)acetamide To a solution of the product of Example 15 (0.40 g) in dimethylformamide (6 mL) was added 2,6-lutidine (0.14 mL) followed by ethyl iodide (0.12 mL). The reaction mixture was stirred at room temperature for 5 days over which time further aliquots (4) of 2,6-lutidine (0.14 mL) and ethyl iodide (0.12 mL) were added. Ethyl acetate was added and the reaction mixture was washed ($H_2O$, saturated aqueous copper sulfate, brine), dried ($MgSO_4$) and evaporated. The residue was purified by chromatography, with dichloromethane:methanol (gradient, 99.5:0.5, 98.5:1.5) as the eluent, to give the title compound; NMR: 0.83–0.91 (dd,6), 1.19 (t,3), 2.07–2.27 (m,1), 4.43–4.73 (m,3), 5.45 (t,1), 7.12 (s,1), 7.20–7.37 (m,2), 7.43–7.63 (m,2), 8.82 (d,1); MS: m/z=443(M+1).

Analysis for $C_{20}H_{22}F_4N_4O_3$: Calculated: C, 54.29; H, 5.01; N, 12.66. Found: C, 54.36; H, 5.19; N, 12.50.

EXAMPLES 81–83

Using procedures similar to that described in Example 80, the following compounds of formula I wherein $R^O$ is isopropyl, R is ethyl and $R^6$ is the indicated group were prepared from the corresponding compounds of formula I wherein R is hydrogen.

EXAMPLE 81

$R^6$=phenyl: Chromatography solvent: dichloromethane:methanol (gradient, 99.5:0.5, 99.3:0.7); TLC: $R_f$=0.37, dichloromethane:methanol (98:2); NMR: 0.73–1.00 (m,6), 1.17 (t,3), 2.07–2.30 (m,1), 3.03–3.23 (m,2), 4.40–4.70 (m,3), 5.40 (t,1), 7.12 (s,1), 7.33–7.57 (m,5), 8.79 (d,1); MS: m/z=425(M+1).

Analysis for $C_{20}H_{23}F_3N_4O_3$: Calculated: C, 56.59; H, 5.46; N, 13.20. Found: C, 56.69; H, 5.53; N, 13.08.

EXAMPLE 82

$R^6$=2-thienyl: Chromatography solvent: dichloromethane:methanol (gradient, 99.5:0.5, 99.3:0.7); TLC: $R_f$=0.37, dichloromethane:methanol (98:2); NMR: 0.83–1.07 (m,6), 1.10–2.23 (t,3), 2.13–3.13 (m,1), 3.03–3.17 (m,2), 4.67–4.87 (m,3), 5.55 (t,1), 7.03–7.20 (m,3), 7.69 (d,1), 8.97 (d,1); MS: m/z=431(M+1).

Analysis for $C_{18}H_{21}F_3N_4O_3S$: Calculated: C, 50.22; H, 4.91; N, 13.01. Found: C, 50.13; H, 5.00; N, 12.93.

EXAMPLE 83

$R^6$=3,5-difluorophenyl: Chromatography solvent: dichloromethane:methane (two columns, gradient, 99.5:0.5, 99.3:0.7); TLC: $R_f$=0.47, dichloromethane:methanol (98:2); NMR: 0.80–1.0 (m,6), 1.17 (t,3), 2.10–2.30 (m,1), 3.03–3.20 (m,2), 4.47–4.73 (m,3), 5.57 (t,1), 7.07–7.23 (m,3), 7.33–7.50 (m,1), 8.86 (d,1); MS: m/z=461(M+1).

Analysis for $C_{20}H_{21}F_5N_4O_3$: Calculated: C, 52.17; H, 4.59; N, 12.16. Found: C, 52.00; H, 4.84; N, 11.80.

EXAMPLE 84

2-[2-(4-Fluorophenyl)-5-methylamino-6-oxo-1,6-dihydro-1-pyrimidinyl]-N-(3,3,3-trifluoro-1-isopropyl-2-oxopropyl)acetamide To a solution of 2-[2-(4-fluorophenyl)-5-(N-trifluoroacetyl-N-methylamino)-6-oxo-1,6-dihydro-1-pyrimidinyl]-N-(3,3,3,-trifluoro-1-isopropyl-2-oxopropyl)acetamide (0.58 g) in tetrahydrofuran (5 mL) was added water (10 mL) followed by potassium carbonate (0.76 g). The mixture was stirred overnight, extracted into dichloromethane, washed (water, brine), dried ($MgSO_4$) and evaporated. The residue was purified by chromatography, with dichloromethane:methanol (gradient, 99.5:0.5, 98.5:1.5) as the eluent, to give the title compound; TLC: $R_f$=0.34, dichloromethane:methanol (98:2); NMR: 0.70–1.0 (m,6), 2.03–2.33 (m,1), 2.71 (d,3), 4.00–4.70 (m,3), 5.63–5.73 (m,1), 7.03 (s,1), 7.17–7.30 (m,2), 7.43–7.60 (m,2), 8.81 (d,1); MS: m/z=429(M+1).

Analysis for $C_{19}H_{20}F_4N_4O_3.0.4H_2O$: Calculated: C, 52.39; H, 4.81; N, 12.86. Found: C, 52.38; H, 4.76; N, 12.76.

The intermediate N-trifluoroacetyl-N-methylamino compound was prepared as follows.

To a solution of the product of Example 75 (0.57 g) in dimethylformamide was added $Na_2CO_3$ (0.32 g), followed by methyl iodide (0.52 mL). The mixture was stirred overnight. Dichloromethane was added and the mixture was filtered. The filtrates were washed (H₂O, brine), dried (MgSO₄), and evaporated. The residue was purified by chromatography, with dichloromethane:acetone (gradient, 95:5, 90:10) as the eluent, to give the N-trifluoroacetyl-N-methylamino compound; TLC: $R_f$=0.33, dichloromethane:acetone (90:10); MS: m/z=525(M+1).

EXAMPLES 85–88

Using procedures similar to that described in Example 84, the following compounds of formula I wherein $R^0$ is isopropyl, R is methyl and $R^6$ is the indicated group were prepared from the corresponding 2-[2-aryl-5-(N-trifluoroacetyl-N-methylamino)-6-oxo-1,6-dihydro-1-pyrimidinyl]-N-(3,3,3-trifluoro-1-isopropyl-2-oxopropyl)acetamides wherein $R^6$ is the indicated aryl group.

EXAMPLE 85

$R^6$=phenyl: Chromatography solvent: dichloromethane:methanol (gradient, 99.5:0.5, 98.5:1.5); TLC: $R_f$=0.36, dichloromethane:methanol (98:2); NMR: 0.73–1.0 (m,6), 2.07–2.33 (m,1), 2.73 (d,3), 4.07–4.73 (m,3), 5.63–5.73 (m,1), 7.05 (s,1), 7.37–7.53 (m,5), 8.81 (d,1); MS: m/z=411(M+1).

Analysis for C₁₉H₂₁F₃N₄O₃.0.3H₂O: Calculated: C, 54.88; H, 5.23; N, 13.47. Found: C, 54.93; H, 5.20; N, 13.48.

EXAMPLE 86

$R^6$=4-methoxyphenyl: Chromatography solvent: dichloromethane:methanol (gradient, 99.5:0.5, 98.5:1.5); TLC: $R_f$=0.41, dichloromethane:methanol (98:2); NMR: 0.80–1.00 (m,6), 2.07–2.27 (m,1), 2.71 (d,3), 3.79 (s,3), 4.40–4.70 (m,3), 5.58 (d,1), 6.90–7.00 (m,2), 7.03 (s,1), 7.27–7.40 (m,2), 8.79 (d,1); MS: m/z=441(M+1).

Analysis for C₂₀H₂₃F₃N₄O₄: Calculated: C, 54.54; H, 5.26; N, 12.72. Found: C, 54.16; H, 5.42; N, 12.49.

EXAMPLE 87

$R^6$=2-thienyl: Chromatography solvent: dichloromethane:methanol (gradient, 99.5:0.5, 99.3:0.7); TLC: $R_f$=0.30, dichloromethane:methanol (98:2); NMR: 0.73–1.0 (m,6), 2.17–2.33 (m,1), 2.71 (s,3), 4.07–4.33 (m,1), 4.67–4.97 (m,2), 5.70–5.87 (m,1), 7.07–7.30 (m,3), 7.63–7.73 (m,1), 8.06 (d,1); MS: m/z=417(M+1).

Analysis for C₁₇H₁₉F₃N₄O₃S.0.6CH₃OH.0.5H₂O: Calculated: C, 47.54; H, 5.07; N, 12.60. Found: C, 48.06; H, 5.04; N, 12.23.

EXAMPLE 88

$R^6$=3,5-difluorophenyl: Chromatography solvent: dichloromethane:methanol (gradient, 99.5:0.5, 99.3:0.7); TLC: $R_f$=0.30, dichloromethane:methanol (98:2); NMR: 0.70–0.97 (m,6), 2.07–2.27 (m,1), 2.71 (d,3), 4.37–4.73 (m,3), 5.77–5.90 (m,1), 7.03 (s,1), 7.10–7.23 (m,2), 7.33–7.47 (m,1), 8.85 (d,1); MS: m/z=447(M+1).

Analysis for C₁₉H₁₉F₅N₄O₃: Calculated: C, 51.12; H, 4.29; N, 12.55. Found: C, 51.06; H, 4.37; N, 12.38.

EXAMPLES 85.a.–88.a.

Using procedures similar to that described in Example 84.a., the following 2-[2-aryl-5-(N-trifluoroacetyl-N-methylamino)-6-oxo-1,6-dihydro-1-pyrimidinyl]-N-(3,3,3-trifluoro-1-isopropyl-2-oxopropyl)acetamides wherein $R^6$ is the indicated aryl group were prepared from the corresponding compounds of formula I wherein R is trifluoroacetyl, which were prepared in Examples 76–79.

Example 85.a.

$R^6$=phenyl: Chromatography solvent: dichloromethane:acetone (gradient, 95.0:5.0, 90.0:10.0); TLC: $R_f$=0.30, dichloromethane:acetone (90:10); MS: m/z=507(M+1).

Example 86.a.

$R^6$=4-methoxyphenyl: Chromatography solvent: dichloromethane:methanol (gradient, 99.5:0.5, 98.5:1.5); TLC: $R_f$=0.33, dichloromethane:methanol (98:2); MS: m/z=537(M+1).

Example 87.a.

$R^6$=2-thienyl: Chromatography solvent: dichloromethane:methanol (gradient, 99.5:0.5, 99.0:1.0); TLC: $R_f$=0.37, dichloromethane:methanol (98:2); MS: m/z=513(M+1).

Example 88.a.

$R^6$=3,5-difluorophenyl: Chromatography solvent: dichloromethane:methanol (gradient 99.5:0.5, 99.3:0.7); TLC: $R_f$=0.39, dichloromethane:methanol (98:2); MS: m/z=543(M+1).

EXAMPLE 89

2-[2-(3,5-Difluorophenyl)-5-formamido-6-oxo-1,6-dihydro-1-pyrimidinyl]-N-(3,3,3-trifluoro-1-isopropyl-2-oxopropyl)acetamide The title compound was prepared using the method described in Chen and Benoiton, *Synthesis* (1979), 709.

To a suspension of 1-(3-dimethylaminopropyl)-3-ethylcarbodiimide hydrochloride (0.193 g) in dichloromethane (8 mL) was added 90% formic acid (1 mL). This mixture was stirred at room temperature for 10 min. To this mixture was then added N-methylmorpholine (0.10 mL) followed by the product from Example 27 (0.40 g). After 3 days, the reaction was diluted with dichloromethane, washed (brine), dried (MgSO₄) and evaporated. The residue was purified by chromatography, with dichloromethane:methanol (gradient, 99.5:0.5, 98:2) as the eluent, to give the title compound; TLC: $R_f$=0.53, dichloromethane:acetone (70:30); NMR: 0.67–1.00 (m,6), 2.07–2.30 (m,1), 4.33–4.83 (m,3), 7.17–7.30 (m,2), 7.43–7.57 (m,1), 8.38 (s,1), 8.83–8.97 (m,2), 10.12 (s,1); MS: m/z=461(M+1).

Analysis for C₁₉H₁₇F₅N₄O₄.0.4H₂O: Calculated: C, 48.80; H, 3.83; N, 11.98. Found: C, 48.81; H, 3.94; N, 11.77.

EXAMPLE 90

2-[2-(4-Fluorophenyl)-6-oxo-5-(2,2,2-trifluoroethoxycarbonylamino)-1,6-dihydro-1-pyrimidinyl]-N-(3,3,3-trifluoro-1-isopropyl-2-oxopropyl)acetamide To a solution of the compound from Example 15 (414 mg) in tetrahydrofuran (8 mL) and dichloromethane (8 mL) at 0° C. was added pyridine (320 mg) followed by 2,2,2-trifluoroethyl chloroformate (300 uL). After 1 h the reaction mixture was diluted with diethyl ether and quenched with ice. The phases were separated and the organic phase was washed (dilute hydrochloric acid, brine), dried, and evaporated to afford a gummy solid. This solid was triturated with diethyl ether:hexanes (10 mL, 1:1) to afford a white powder, which was collected by filtration and dried under vacuum to yield the title compound (460 mg); $R_f=0.48$, chloroform:methanol (20:1); NMR DMSO/D$_2$O): 8.40 (s,1), 7.56 (m,2), 7.28 (m,2), 4.83–4.56 (mm,4), 2.22 (m,1), 0.80 (dd,6); MS: m/z=541(M+1).

Analysis for $C_{21}H_{19}F_7N_4O_5\cdot 0.5H_2O$: Calculated: C, 45.91; H, 3.67; N, 10.20. Found: C, 46.05; H, 3.52; N, 10.25.

The intermediate 2,2,2-trifluoroethyl chloroformate was prepared using a procedure similar to that described in U.S. Pat. No. 3,852,464, except that bis(trichloromethyl) carbonate was used in place of phosgene.

EXAMPLES 91–108

Using procedures similar to that described in Example 90 and using the required acyl, sulfonyl, or aminosulfonyl chloride, the following compounds of formula I wherein $R^0$ is isopropyl and R and $R^6$ have the indicated values were prepared from the corresponding compounds of formula I wherein R is hydrogen.

EXAMPLE 91

R=cyclohexylaminosulfonyl, $R^6$=4-fluorophenyl: Purified by trituration with methyl tert-butyl ether:diethyl ether; TLC: $R_f=0.33$, tetrahydrofuran:dichloromethane (1:9); NMR: 8.92 (s,1), 8.82 (d,1), 7.96 (s,1), 7.64 (d,1), 7.51 (m,2), 7.31 (t,2), 4.61 (m,3), 1.78–1.18 (m,10), 0.88 (d,3), 0.82 (d,3); MS: m/z=576(M+1).

Analysis for $C_{24}H_{29}F_4N_5O_5S$: Calculated: C, 50.08; H, 5.08; N, 12.17. Found: C, 50.11; H, 5.20; N, 11.90.

EXAMPLE 92

R=benzylaminosulfonyl, $R^6$=4-fluorophenyl: Chromatography solvent: dichloromethane:methanol (30:1); TLC: $R_f=0.29$, dichloromethane:methanol (20:1); NMR: 9.15 (s,1), 8.85 (d,1), 8.2 (m,1), 7.95 (s,1), 7.53 (m,2), 7.30 (m,7), 4.67 (t,1), 4.13 (d,2), 2.2 (m,1), 0.83 (dd,6); MS: m/z=584(M+1).

Analysis for $C_{25}H_{25}F_4N_5O_5S$: Calculated: C, 51.46; H, 4.32; N, 12.00. Found: C, 51.35; H, 4.49; N, 11.86.

EXAMPLE 93

R=cyclohexylaminosulfonyl, $R^6$=phenyl: Purified by trituration with diethyl ether; TLC: $R_f=0.31$, dichloromethane:methanol (20:1); NMR (DMSO/D$_2$O): 8.0 (s,1), 7.5 (mm,5), 4.60 (dd,2), 4.0 (m,1), 3.1 (m,1), 2.2 (m,1), 1.7–1.4 (mm,4), 1.3–1.1 (mm,6), 0.82 (qd,6); MS: m/z=558(M+1).

Analysis for $C_{24}H_{30}F_3N_5O_5S\cdot 0.5H_2O$: Calculated: C, 50.87; H, 5.51; N, 12.36. Found: C, 59.92; H, 5.46; N, 12.18.

EXAMPLE 94

R=benzylaminosulfonyl, $R^6$=phenyl: Chromatography solvent: dichloromethane:methanol (30:1); TLC: $R_f=0.28$, dichloromethane:methanol (20:1); NMR: 9.10 (s,1), 8.84 (d,1), 8.15 (m,1), 7.95 (s,1), 7.47 (m,5), 7.29 (m,5), 4.68 (dd,1), 4.53 (2d,2), 4.12 (d,2), 2.17 (m,1), 0.89 (dd,6); MS: m/z=566(M+1).

Analysis for $C_{25}H_{26}F_3N_5O_5S$: Calculated: C, 52.26; H, 4.74; N, 12.19. Found: C, 52.15; H, 4.69; N, 12.10.

EXAMPLE 95

R=benzylsulfonyl, $R^6$=4-fluorophenyl: Chromatography solvent: dichloromethane:methanol (99:1); TLC: $R_f=0.44$, dichloromethane:methanol (20:1); NMR (DMSO/D$_2$O): 7.72 (s,1), 7.55–7.26 (mm,9), 4.6 (s,2), 4.58 (dd,2), 2.24 (m,1), 0.86 (d,3), 0.76 (d,3); MS: m/z=569(M+1).

Analysis for $C_{25}H_{24}F_4N_4O_5S$: Calculated: C, 52.81; H, 4.25; N, 9.85. Found: C, 53.01; H, 4.36, N, 9.69.

EXAMPLE 96

R=benzylsulfonyl, $R^6$=phenyl: Chromatography solvent: dichloromethane:acetonitrile (9:1), followed by trituration with diethyl ether; TLC: $R_f=0.44$, dichloromethane:methanol (95:5); NMR: 9.33 (s,1), 8.86 (d,1), 7.77 (s,1), 7.58–7.33 (m,10), 4.69 (m,1), 4.60 (s,2), 2.50 (m,1), 0.90 (d,3), 0.88 (d,3); MS: m/z=551(M+1).

Analysis for $C_{25}H_{25}F_3N_4O_5S$: Calculated: C, 54.54; H, 4.58; N, 10.18. Found: C, 54.80; H, 4.53; N, 10.09.

EXAMPLE 97

R=isopropylaminosulfonyl, $R^6$=phenyl: Chromatography solvent: dichloromethane:methanol (98:2), followed by trituration with diethyl ether; TLC: $R_f=0.28$, dichloromethane:methanol (20:1); NMR: 8.96 (s,1), 8.2 (d,1), 7.96 (s,1), 7.51 (m,5), 5.55 (dd,2), 3.42 (m,1), 2.34 (m,1), 1.05 (d,6), 0.88 (d,3), 0.82 (d,3); MS: m/z=518(M+1).

Analysis for $C_{21}H_{26}F_3N_5O_5S$: Calculated: C, 48.74; H, 5.06; N, 13.53. Found: C, 48.53; H, 5.11; N, 13.45.

EXAMPLE 98

R=methoxycarbonyl, $R^6$=3,5-difluorophenyl: Chromatography solvent: dichloromethane:methanol (96:4); TLC: $R_f=0.47$, dichloromethane:methanol (95:5); NMR: 8.46 (s,1), 7.43 (t,1), 7.22 (d,2), 4.71 (d,1), 4.45 (d,1), 4.02 (d,1), 3.70 (s,3), 2.24 (m,1), 0.85 (d,3), 0.75 (d,3); MS: m/z=491(M+1).

Analysis for $C_{20}H_{19}F_5N_4O_5$: Calculated: C, 48.98; H, 3.90; N, 11.42. Found: C, 49.22; H, 3.93; N, 11.52.

EXAMPLE 99

R=2,2,2-trifluoroethoxycarbonyl, $R^6$=phenyl: Purified by trituration with diethyl ether:hexanes (1:5); TLC: $R_f=0.42$, chloroform:methanol (20:1); NMR (DMSO/D$_2$O): 8.41 (s,1), 7.5 (m,5), 4.79 (m,2), 4.67 (dd,2), 2.24 (m,1), 0.82 (dd,6); MS: m/z=523(M+1).

Analysis for $C_{21}H_{20}F_6N_4O_5\cdot 0.7H_2O$: Calculated: C, 47.14; H, 4.03; N, 10.47. Found: C, 47.03; H, 4.07; N, 10.32.

EXAMPLE 100

R=methylthiocarbonyl, $R^6$=phenyl: Purified by trituration with diethyl ether:hexanes (1:5); TLC: $R_f=0.38$, dichloromethane:methanol (20:1); NMR: 9.98 (s,1), 8.85 (d,1), 8.60 (s,1), 7.50 (m,5), 4.68 (t,1), 4.55 (dd,2), 2.30 (s,3), 2.18 (m,1), 0.87 (dd,6); MS: m/z=471(M+1).

Analysis for $C_{20}H_{21}F_3N_4O_4S$: Calculated: C, 51.06; H, 4.50; N, 11.91. Found: C, 51.04; H, 4.64; N, 11.59.

EXAMPLE 101

R=ethylthiocarbonyl, $R^6$=phenyl: Purified by trituration with diethyl ether:hexanes (1:5); TLC: $R_f=0.41$, dichloromethane:methanol (20:1); NMR: 9.88 (d,1), 8.86 (d,1), 8.59 (s,1), 7.49 (m,5), 4.69 (t,1), 4.55 (m,2), 2.85 (q,2), 2.17 (m,1), 1.25 (t,3), 0.88 (dd,6); MS: m/z=485(M+1).

Analysis for $C_{21}H_{23}F_3N_4O_4S\cdot 0.35H_2O$: Calculated: C, 51.39; H, 4.87; N, 11.42. Found: C, 51.36; H, 4.93; N, 11.34.

EXAMPLE 102

R=methylthiocarbonyl, $R^6$=4-fluorophenyl: Purified by trituration with diethyl ether:hexanes (1:5); TLC: $R_f$=0.44, dichloromethane:methanol (20:1); NMR: 10.0 (s,1), 8.85 (d,1), 8.58 (s,1), 7.55 (dd, ), 7.35 (dd,2), 4.66 (t,1), 4.59 (dd,2), 2.29 (s,3), 2.18 (m,1), 0.88 (dd,6); MS: m/z=489(M+1).

Analysis for $C_{20}H_{20}F_4N_4O_4S$: Calculated: C, 49.18; H, 4.13; N, 11.47. Found: C, 49.23; H, 4.19; N, 11.47.

EXAMPLE 103

R=ethylthiocarbonyl, $R^6$=4-fluorophenyl: Purified by trituration with diethyl ether:hexanes (1:5); TLC: $R_f$=0.45, dichloromethane:methanol (20:1); NMR: 9.90 (s,1), 8.85 (d,1), 8.55 (s,1), 7.55 (m,2), 7.32 (m,2), 4.67 (t,1), 4.59 (m,2), 2.85 (q,2), 2.15 (m,1), 1.25 (t,3), 0.86 (dd,6); MS: m/z=503(M+1).

Analysis for $C_{21}H_{22}F_4N_4O_4S.0.4H_2O$: Calculated: C, 49.49; H, 4.51; N, 10.99. Found: C, 49.54; H, 4.53; N, 11.07.

EXAMPLE 104

R=methylthiocarbonyl, $R^6$=2-thienyl: Purified by trituration with diethyl ether:hexanes (1:5); TLC: $R_f$=0.48, dichloromethane:methanol (20:1); NMR: 9.98 (s,1), 9.05 (d,1), 8.55 (s,1), 7.84 (d,1), 7.48 (d,1), 7.25 (t,1), 4.89 (t,1), 4.8 (dd,2), 2.29 (s,3), 2.22 (m,1), 0.95 (dd,6); MS: m/z=477(M+1).

Analysis for $C_{18}H_{19}F_3N_4O_4S_2.0.75H_2O$: Calculated: C, 44.12; H, 4.22; N, 11.43. Found: C, 44.13; H, 4.24; N, 11.27.

EXAMPLE 105

R=ethylthiocarbonyl, $R^6$=2-thienyl: Purified by trituration with diethyl ether:hexanes (1:5); TLC: $R_f$=0.47, dichloromethane:methanol (20:1); NMR: 9.90 (s,1), 9.07 (d,1), 8.55 (s,1), 7.85 (d,1), 7.48 (d,1), 7.17 (t,1), 4.89 (t,1), 4.84 (dd,2), 1.25 (t,3), 2.87 (q,2), 2.24 (m,1), 0.94 (dd,6); MS: m/z=491(M+1).

Analysis for $C_{18}H_{19}F_3N_4O_4S_2.0.75H_2O$: Calculated: C, 45.28; H, 4.50; N, 11.12. Found: C, 45.44; H, 4.45; N, 11.02.

EXAMPLE 106

R=2,2,2-trifluoroethoxycarbonyl, $R^6$=2-thienyl: Purified by trituration with diethyl ether:hexanes (1:5); TLC: $R_f$=0.49, dichloromethane:methanol (20:1); NMR: 9.47 (s,1), 9.05 (d,1), 8.35 (s,1), 7.87 (d,1), 7.40 (d,1), 7.16 (t,1), 4.98–4.73 (mm,3), 2.26 (m,1), 0.96 (dd,6); MS: m/z=529(M+1).

Analysis for $C_{19}H_{18}F_6N_4O_5S.0.5H_2O$: Calculated: C, 42.46; H, 3.56; N, 10.42. Found: C, 42.52; H, 3.71; N, 10.39.

EXAMPLE 107

R=tert-butylaminosulfonyl, $R^6$=4-fluorophenyl: Chromatography solvent: dichloromethane:methanol (95:5); TLC: $R_f$=0.17, dichloromethane:methanol (95:5); NMR (DMSO/$D_2O$): 7.97 (s,1), 7.55 (m,2), 7.28 (t,2), 4.68 (d,2), 4.47 (d,1), 4.02 (d,1), 2.21 (m,1), 1.23 (s,9), 0.84 (d,3), 0.74 (d,3); MS: m/z=550(M+1).

Analysis for $C_{22}H_{27}F_4N_5O_5S.0.5H_2O$: Calculated: C, 47.3; H, 5.05; N, 12.5. Found: C, 47.4; H, 5.09; N, 12.4.

EXAMPLE 108

R=tert-butylaminosulfonyl, $R^6$=phenyl: Chromatography solvent: dichloromethane:methanol (95:5); TLC: $R_f$=0.21, dichloromethane:methanol (95:5); NMR (DMSO/$D_2O$): 7.94 (s,1), 7.44 (s,5), 4.50 (dd,2), 4.00 (m,1), 2.50 (m,1), 1.19 (s,9), 0.80 (d,3), 0.73 (d,3); MS: m/z=532(M+1).

Analysis for $C_{22}H_{28}F_3N_5O_5S.0.25H_2O$ Calculated: C, 49.3; H, 5.36; N, 13.1. Found: C, 49.3; H, 5.44; N, 12.9.

EXAMPLE 109

2-[5-Dimethylaminooxycarbonylamino-2-(4-fluorophenyl)-6-oxo-1,6-dihydro-1-pyrimidinyl]-N-(3,3,3-trifluoro-1-isopropyl-2-oxo-propyl)acetamide A slurry of the compound from Example 15 (0.414 g) in dry dichloromethane (10 mL) was cooled in an ice/salt bath to an internal temperature of less than 1° C. Bis(trichloromethyl) carbonate (0.1994 g) as a solution in dry dichloromethane (5 mL) was added dropwise at such a rate to maintain the internal temperature below 2° C. After the addition was complete, the reaction was stirred an additional 10 min. Triethylamine (1.18 mL) as a solution in dry dichloromethane was added dropwise, maintaining an internal temperature of less than 4° C.; and, after the addition was complete, the reaction was stirred an additional 20 min. N,N-Dimethylhydroxylamine hydrochloride (0.1983 g) was added as a solid to the reaction mixture and it was stirred for 30 min. The reaction mixture was diluted with ethyl acetate, washed (saturated ammonium chloride, brine), dried and evaporated to yield a solid. This solid was triturated with diethyl ether to give the title compound (0.3338 g) as a white solid; TLC: $R_f$=0.4, dichloromethane:methanol (20:1); NMR: 8.55 (s,1), 7.54 (m,2), 7.29 (m,2), 4.59 (dd,2), 4.02 (dd,1), 2.82 (s,6), 2.22 (m,1), 0.84 (d,3), 0.74 (d,3); MS: m/z=502(M+1).

Analysis for $C_{21}H_{23}F_4N_5O_5$: Calculated: C, 50.30; H, 4.62; N, 13.97. Found: C, 50.32; H, 4.68; N, 13.79.

EXAMPLES 110–112

The following compounds of formula I wherein $R^0$ is isopropyl and R and $R^6$ have the indicated values were prepared using procedures similar to that described in Example 109 by replacing 2-[5-amino-2-(4-fluorophenyl)-6-oxo-1,6-dihydro-1-pyrimidinyl]-N-(3,3,3-trifluoro-1-isopropyl-2-oxo-propyl)acetamide with the compound of formula I wherein R is hydrogen and $R^6$ is the indicated group and by replacing N,N-dimethylhydroxylamine hydrochloride with the required nucleophile.

EXAMPLE 110

R=methylaminocarbonyl, $R^6$=4-fluorophenyl: Using methylamine hydrochloride; chromatography solvent: dichloromethane:methanol (20:1), followed by washing an ethyl acetate solution of the appropriate fractions with 0.1N HCl, drying and evaporation to give a solid; TLC: $R_f$=0.19, dichloromethane:methanol (20:1); NMR: 8.65 (s,1), 7.53 (m,2), 7.26 (t,2), 4.64 (d,1), 4.45 (d,1), 4.04 (d,1), 2.65 (s,3), 2.22 (m,1), 0.86 (d,3), 0.76 (d,3); MS: m/z=472(M+1).

Analysis for $C_{20}H_{21}F_4N_5O_4.0.33H_2O$: Calculated: C, 50.32; H, 4.57; N, 14.67. Found: C, 50.42; H, 4.54; N, 14.77.

EXAMPLE 111

R=isopropylaminocarbonyl, $R^6$=phenyl: Using isopropylamine; chromatography solvent: dichloromethane:methanol (97:3); TLC: $R_f$=0.28, dichloromethane:methanol (95:5); NMR (DMSO/$D_2O$): 8.64 (s,1), 7.46 (m,5), 4.61 (d,1), 4.45 (d,1), 4.08 (d,1), 3.72 (m,1), 2.24 (m,1), 1.09 (d,6), 0.87 (d,3), 0.79 (d,3); MS: m/z=482(M+1).

Analysis for $C_{22}H_{26}F_3N_5O_4$: Calculated: C, 54.88; H, 5.44; N, 14.54. Found: C, 54.60; H, 5.53; N, 14.47.

EXAMPLE 112

R=methylaminocarbonyl, $R^6$=phenyl: Using methylamine hydrochloride; chromatography solvent: dichloromethane:methanol (96:4), followed by crystallization from dichloromethane; TLC: $R_f$=0.21, dichloromethane:methanol (95:5); NMR (DMSO/D$_2$O): 8.66 (s,1), 7.47 (m,5), 4.61 (d,1), 4.45 (d,1), 4.08 (d,1), 2.66 (s,3), 2.25 (m,1), 0.86 (d,3), 0.79 (d,3); MS: m/z=454(M+1).

Analysis for $C_{20}H_{22}F_3N_5O_4.0.5H_2O$: Calculated: C, 51.95; H, 5.01; N, 15.14. Found: C, 51.86; H, 4.98; N, 15.09.

EXAMPLE 113

2-[2-(4-Fluorophenyl)-5-isopropylaminocarbonyl-6-oxo-1,6-dihydro-1-pyrimidinyl]-N-(3,3,3-trifluoro-1-isopropyl-2-oxo-propyl)acetamide To a slurry of 2-[5-amino-2-(4-fluorophenyl)-6-oxo-1,6-dihydro-1-pyrimidinyl]-N-(3,3,3-trifluoro-1-isopropyl-2-oxopropyl)acetamide (0.414 g) in dry tetrahydrofuran (3 mL) and dichloromethane (5 mL) was added isopropyl isocyanate (110 uL). After overnight stiring, dimethylformamide (1.5 mL), triethylamine (100 uL) and isopropyl isocyanate (50 uL) were added. The reaction mixture was heated to reflux for 24 h. The mixture was cooled to room temperature and cuprous chloride (120 mg) followed by three portions of isopropyl isocyanate (50 uL, 50 uL, and 25 uL) were added. The reaction mixture was diluted with diethyl ether and rinsed with dilute hydrochloric acid and brine. The organic phase was dried and evaporated to afford an oil which was purified by chromatography, with chloroform:methanol (gradient 100:0, 97:3) as the eluent. This afforded 160 mg of a yellow-green solid. Analysis by NMR showed line broadening, indicative of contamination by a heavy metal. The remaining 135 mg sample was dissolved in methyl tert-butyl ether and rinsed with 5% disodium EDTA solution followed by dilute aqueous ammonia. The organic phase was dried and evaporated to afford the title compound (120 mg) as an off-white powder; TLC: $R_f$=0.46, chloroform:methanol (9:1); NMR: 8.62 (s,1), 7.52 (dd,2), 7.26 (dd,2), 4.6 (dd,2), 4.04 (d,1), 2.25 (m,1), 1.09 (d,6), 0.85 (d,3), 0.76 (d,3); MS: m/z=500(M+1).

Analysis for $C_{22}H_{25}F_4N_5O_4.0.25H_2O$: Calculated: C, 52.43; H, 5.10; N, 13.90. Found: C, 52.78; H, 5.24; N, 13.58.

EXAMPLE 114

2-(6-Oxo-2-phenyl-5-ureido-1,6-dihydro-1-pyrimidinyl)-N-(3,3,3-trifluoro-1-isopropyl-2-oxo-propyl)acetamide To a solution of the compound from Example 6 (0.40 g) in tetrahydrofuran (10 mL) cooled to 0° C. was added dropwise chlorosulfonyl isocyanate (0.16 g) and the mixture was stirred for 45 min. The reaction mixture was neutralized with saturated aqueous sodium carbonate solution (3 mL), diluted with ethyl acetate (10 mL), and the separated organic phase was washed (water, brine). TLC examination revealed that the major reaction product was present in the aqueous phase. Following saturation of the aqueous phase with sodium chloride, repeated ethyl acetate extractions (4×25 mL) were performed. The combined organic layers were dried (magnesium sulfate) and evaporated. Chromatography with dichloromethane:tetrahydrofuran (10:1) as the eluent, followed by overnight drying (50° C., 27 Pa) gave the title compound (0.061 g) as an off-white solid; TLC: $R_f$=0.36, dichloromethane:methanol (10:1); NMR: 8.85 (d,1), 8.69 (s,1), 8.35 (s,1), 7.48 (m,5), 6.47 (broad s, 2), 4.70 (dd,1), 4.55 (dd,2), 2.2 (m,1), 0.89 (dd,6); MS: m/z=440(M+1).

Analysis for $C_{19}H_{20}F_3N_5O_4.0.60H_2O$: Calculated: C, 50.69; H, 4.75; N, 15.56. Found: C, 50.82; H, 4.83; N, 15.24.

EXAMPLE 115

2-[2-(4-Fluorophenyl)-5-methylsulfonylamino-6-oxo-1,6-dihydro-1-pyrimidinyl]-N-(3,3,3-trifluoro-1-isopropyl-2-oxopropyl)acetamide To a solution of the compound from Example 15 (0.45 g) in tetrahydrofuran (11 mL) was added pyridine (0.89 mL) and the mixture cooled in an ice bath to 0° C. Methylsulfonyl chloride (0.17 mL) was added and the solution warmed to room temperature and allowed to stir for 24 h. The reaction mixture was poured into ethyl acetate and washed with a saturated solution of potassium dihydrogen phosphate, and then H$_2$O. The resulting solution was dried and the solvent removed by evaporation. The resulting material was purified by chromatography, eluting with tetrahydrofuran:dichloromethane (gradient, 10:90, 20:80) to give the title compound (0.48 g) as a white powder; TLC: $R_f$=0.67, tetrahydrofuran:dichloromethane (20:80); NMR (DMSO/D$_2$O): 7.97 (s,1), 7.55 (m,2), 7.27 (t,2), 4.66 (d,1), 4.45 (d,1), 4.00 (d,1), 3.07 (s,3), 2.16 (s,1), 0.83 (d,3), 0.72 (d,3).

Analysis for $C_{19}H_{20}F_4N_4O_5S.0.3H_2O$: Calculated: C, 45.8; H, 4.17; N, 11.3. Found: C, 45.8; H, 4.32; N, 11.0.

EXAMPLES 116–125

Using procedures similar to that described in Example 115 and using the required sulfonyl chloride, the following compounds of formula I wherein $R^0$ is isopropyl and R and $R^6$ have the indicated values were prepared from the corresponding compounds of formula I wherein R is hydrogen.

EXAMPLE 116

R=methylsulfonyl, $R^6$=3-pyridyl: Chromatography solvent: methanol:dichloromethane (gradient, 5:95, 10:90); TLC: $R_f$=0.40, methanol/dichloromethane (7:93); NMR: 8.70 (d,1), 8.81 (t,2), 8.03 (s,1), 7.90 (m,2), 7.48 (m,1), 4.72 (d,1), 4.51 (d,1), 4.00 (d,1), 3.11 (s,3), 2.19 (m,1), 0.82 (d,3), 0.70 (d,3).

Analysis for $C_{18}H_{20}F_3N_4O_5S.0.4H_2O$: Calculated: C, 44.8; H, 4.34; N, 14.5. Found: C, 44.7; H, 4.35; N, 14.3.

EXAMPLE 117

R=methylsulfonyl, $R^6$=2-thienyl: Chromatography solvent: methanol:dichloromethane (gradient, 5:95, 8:92); TLC: $R_f$=0.34, tetrahydrofuran:dichloromethane (10:90); NMR: 7.95 (s,1), 7.83 (d,1), 7.42 (d,1), 7.12 (t,1), 4.85 (d,1), 4.51 (m,2), 4.08 (d,1), 3.06 (s,3), 2.25 (m,1), 0.90 (d,3), 0.75 (d,3).

Analysis for $C_{17}H_{19}F_3N_4O_5S_2$: Calculated: C, 42.5; H, 3.99; N, 11.7. Found: C, 42.1; H, 4.12; N, 11.4.

EXAMPLE 118

R=methylsulfonyl, $R^6$=4-trifluoromethylphenyl: Chromatography solvent: methanol:dichloromethane (5:95); TLC: $R_f$=0.12, methanol:dichloromethane (5:95); NMR (DMSO:D$_2$O): 7.99 (s,1), 7.79 (d,2), 7.67 (d,2), 4.59 (m,2), 3.99 (d,1), 3.09 (s,3), 2.15 (m,1), 0.75 (d,3), 0.63 (d,3).

Analysis for $C_{20}H_{20}F_6N_4O_5S.0.5H_2O$: Calculated: C, 43.5; H, 3.84; N, 10.1. Found: C, 43.6; H, 3.91; N, 10.5.

EXAMPLE 119

R=4-methoxyphenylsulfonyl, $R^6$=4-trifluoromethylphenyl: Chromatography solvent: ethyl acetate:hexane (gradient, 50:50, 100:0); TLC: $R_f$=0.57, ethyl acetate; NMR (DMSO:D$_2$O): 7.89 (s,1), 7.82 (d,2), 7.74 (d,2), 7.60 (d,2), 7.06 (d,2), 4.49 (m,2), 3.88 (d,1), 3.78 (s,3), 2.12 (m,1), 0.71 (d,3), 0.59 (d,3).

Analysis for $C_{26}H_{24}F_6N_4O_6S$: Calculated: C, 49.2; H, 3.81; N, 8.83. Found: C, 49.0; H, 3.77; N, 8.77.

EXAMPLE 120

R=methylsulfonyl, $R^6$=3,5-difluorophenyl: Chromatography solvent: tetrahydrofuran:dichloromethane (gradient, 15:85, 30:70); TLC: $R_f$=0.41, tetrahydrofuran:dichloromethane (10:90); NMR (DMSO:D$_2$O): 7.96 (s,1), 7.40 (m,1), 7.19 (d,2), 4.68 (d,1), 4.40 (d,1), 3.99 (s,1), 3.08 (s,3), 2.20 (m,1), 0.81 (d,3), 0.70 (d, 3).

Analysis for $C_{19}H_{19}F_5N_4O_5S.0.6H_2O$: Calculated: C, 43.8; H, 3.90; N, 10.8. Found: C, 43.8; H, 3.80; N, 10.6.

EXAMPLE 121

R=phenylsulfonyl, $R^6$=3,5-difluorophenyl: Chromatography solvent: tetrahydrofuran:dichloromethane (gradient, 5:95 to 15:85); TLC: $R_f$=0.50, tetrahydrofuran:dichloromethane (17:83); NMR (DMSO/D$_2$O): 7.90 (m,3), 7.60 (m,3), 7.40 (t,1), 7.17 (d,2), 4.60 (d,1), 4.35 (d,1), 3.96 (d,1), 2.20 (m,1), 0.81 (d,3), 0.67 (d,3).

Analysis for $C_{24}H_{21}F_5N_4O_5S$: Calculated: C, 50.4; H, 3.70; N, 9.79. Found: C, 50.0; H, 3.72; N, 9.69.

EXAMPLE 122

R=phenylsulfonyl, $R^6$=4-nitrophenyl: Chromatography solvent: methanol:dichloromethane (5:95); TLC: $R_f$=0.40, methanol:dichloromethane (5:95); 300 MHz NMR (DMSO/D$_2$O): 8.21 (d,2), 7.86 (m,3), 7.63 (m,4), 4.52 (m,2), 3.89 (d,1), 2.12 (m,1), 0.72 (d,3), 0.60 (d,3).

Analysis for $C_{24}H_{22}F_3N_5O_7S$: Calculated: C, 49.6; H, 3.81; N, 12.0. Found: C, 49.4; H, 4.00; N, 12.0.

EXAMPLE 123

R=4-chlorophenylsulfonyl, $R^6$=4-trifluoromethylphenyl: Chromatography solvent: ethyl acetate:dichloromethane (50:50); TLC: $R_f$=0.55, ethyl acetate; 300 MHz NMR (DMSO/D$_2$O): 7.96 (s,1), 7.85 (d,2), 7.76 (d,2), 7.60 (m,4), 4.60 (d,1), 4.38 (d,2), 3.89 (d,1), 2.11 (m,1), 0.71 (d,3), 0.59 (d,3).

Analysis for $C_{25}H_{21}F_6N_4O_5S$: Calculated: C, 47.0; H, 3.31; N, 8.77. Found: C, 46.7; H, 3.36; N, 8.74.

EXAMPLE 124

R=methylsulfonyl, $R^6$=4-methoxyphenyl: Chromatography solvent: methanol:dichloromethane (5:95); TLC: $R_f$=0.28, methanol:dichloromethane (5:95); 300 MHz NMR: 9.30 (s,1), 8.86 (d,1), 7.98 (s,1), 7.46 (d,2), 7.02 (d,2), 4.67 (t,1), 4.58 (m,2), 3.82 (s,3), 3.07 (s,3), 2.17 (t,1), 0.90 (d,3), 0.84 (d,3).

Analysis for $C_{20}H_{23}F_3N_4O_6S$: Calculated: C, 47.6; H, 4.60; N, 11.1. Found: C, 47.4; H, 4.63; N, 11.0.

EXAMPLE 125

R=5-dimethylamino-1-naphthylsulfonyl, $R^6$=phenyl: Chromatography solvent: ethyl acetate:dichloromethane (25:75); TLC: $R_f$=0.16, ethyl acetate:dichloromethane (25:75); NMR: (DMSO/D$_2$O) 8.47 (d,1), 8.33 (d,1), 8.26 (d,2), 7.81 (s,1), 7.61 (m,2), 7.36 (m,5), 7.25 (d,1), 4.39 (dd,2), 2.79 (s,6), 2.17 (m,1), 0.76 (d,3), 0.69 (d,3).

Analysis for $C_{30}H_{30}F_3N_5O_5S.0.5H_2O$: Calculated: C, 56.4; H, 4.89; N, 11.0. Found: C, 56.2; H, 4.94; N, 11.7.

EXAMPLE 126

2-[2-(4-Dimethylaminophenyl)-5-methylsulfonylamino-6-oxo-1,6-dihydro-1-pyrimidinyl]-N-(3,3,3-trifluoro-1-isopropyl-2-oxopropyl)acetamide To a solution of the product from Example 136 (300 mg) in ethanol (50 mL) and tetrahydrofuran (5 mL) was added formaldehyde (2 mL of a 37% solution of formaldehyde in H$_2$O) and 10% (w/w) palladium on carbon (100 mg). The resulting mixture was placed under a hydrogen atmosphere (3.5 bar) and shaken overnight. The solution was filtered, dried, and evaporated. The resulting oil was chromatographed, eluting with methanol:dichloromethane (gradient, 5:95, 10:90), to give a solid which was washed with diethyl ether:hexane (1:1) to provide the title compound (0.23 g); TLC: $R_f$=0.2, methanol:methylene chloride (5:95); NMR (DMSO:D$_2$O): 7.91 (d,1), 7.33 (d,2), 6.87 (d,2), 4.58 (m,2), 3.96 (d, 1), 3.01 (s,3), 2.95 (s,6), 2.20 (m,1), 0.82 (d,3), 0.74 (d,3).

Analysis for $C_{21}H_{26}F_3N_5O_5S.0.3H_2O$: Calculated: C, 48.2; H, 5.12; N, 13.4. Found: C, 48.5; H, 5.53; N, 13.1.

EXAMPLE 127

2-[2-(4-Aminophenyl)-5-methylsulfonylamino-6-oxo-1,6-dihydro-1-pyrimidinyl]-N-(3,3,3-trifluoro-1-isopropyl-2-oxopropyl)acetamide The product from Example 136 was subjected to a hydrogenation procedure similar to the hydrogenolysis described in Example 2.b. to give the title compound; chromatography solvent: methanol:dichloromethane (gradient, 5:95, 15:85); TLC: $R_f$=0.25, methanol:dichloromethane (5:95); NMR (DMSO/D$_2$O): 7.90 (d,1), 7.20 (d,2), 6.58 (d,2), 4.70 (m,2), 4.00 (d,1), 3.01 (s,3), 2.21 (m,1), 0.86 (d,3), 0.78 (d,3).

Analysis for $C_{19}H_{22}F_3N_5O_5S.0.5H_2O$: Calculated: C, 45.9; H, 4.45; N, 14.1. Found: C, 46.0; H, 4.65; N, 13.9.

EXAMPLES 128–129

Using procedures similar to that described in Example 1, the following compounds of formula I, wherein $R^0$ is isopropyl and R and $R^6$ have the indicated values were prepared by oxidation of the corresponding alcohols of formula II.

EXAMPLE 128

R=2,6-dimethylpyrid-4-ylmethoxycarbonyl, $R^6$=phenyl: Chromatography solvent: methanol:dichloromethane (gradient, 5:95, 10:90); TLC: $R_f$=0.50, methanol:dichloromethane (5:95); NMR (DMSO/D$_2$O): 8.41 (s,1), 7.50 (m,5), 7.06 (s,2), 5.11

(s,2), 4.50 (m,2), 4.01 (m,1), 2.20 (m,1), 0.80 (d,3), 0.73 (d,3).

Analysis for $C_{27}H_{28}F_3N_5O_5.0.1H_2O$: Calculated: C, 57.8; H, 5.06; N, 12.5. Found: C, 57.6; H, 5.00; N, 12.4.

EXAMPLE 129

R=2,6-dimethylpyrid-4-ylmethoxycarbonyl, $R^6$=4-fluorophenyl: Chromatography solvent: tetrahydrofuran:dichloromethane (gradient, 10:90 to 40:60); TLC: $R_f$=0.33, tetrahydrofuran:dichloromethane (30:70); NMR (DMSO/D$_2$O): 8.45 (s,1), 7.54 (m,2), 7.26 (t,2), 7.09 (s,2), 5.14 (s,2), 4.68 (d,1), 4.42 (d,1), 4.03 (d,1), 2.41 (s,6), 2.21 (m,1), 0.84 (d,3), 0.74 (d,3).

Analysis for $C_{27}H_{27}F_4N_5O_5.0.5H_2O$: Calculated: C, 55.3; H, 4.81; N, 11.9. Found: C, 55.2; H, 4.85; N, 12.0.

The intermediate alcohols of formula II used in Examples 128-129 were prepared as follows.

EXAMPLES 128.a.–129.a.

The following compounds of formula XIV wherein $R^0$ is isopropyl, Rp is tert-butyldimethylsilyl and R and $R^6$ have the indicated values were prepared from the corresponding compounds of formula XIII by a procedure similar to that described in Example 3.a. except using the required carbinol.

EXAMPLE 128.a.

R=2,6-dimethylpyrid-4-ylmethoxycarbonyl, $R^6$=phenyl: Chromatography solvent: ethyl acetate:dichloromethane (gradient, 50:50, 75:25); TLC: $R_f$=0.5, methanol:dichloromethane (3:97); MS: m/z=676(M+1).

EXAMPLE 129.a.

R=2,6-dimethylpyrid-4-ylmethoxycarbonyl, $R^6$=4-fluorophenyl: Chromatography solvent: ethyl acetate:dichloromethane (gradient, 50:50 to 75:25); TLC: $R_f$=0.38, methanol:dichloromethane (5:95); MS: m/z=694 (M+1).

EXAMPLES 128.b.–129.b.

The following compounds of formula II wherein $R^0$ is isopropyl and R and $R^6$ have the indicated values were prepared from the corresponding compounds of formula XIV, described in Examples 128.a.–129.a., by procedures similar to that described in Example 2.d.

EXAMPLE 128.b.

R=2,6-dimethylpyrid-4-ylmethoxycarbonyl, $R^6$=phenyl: Purified by crystallization from diethyl ether:hexane (1:1); TLC: $R_f$=0.20, ethyl acetate; MS: m/z=562(M+1).

EXAMPLE 129.b.

R=2,6-dimethylpyrid-4-ylmethoxycarbonyl, $R^6$=4-fluorophenyl: Purified by crystallization from diethyl ether:ethyl acetate (1:1); TLC: $R_f$=0.30, ethyl acetate:dichloromethane (75:25); MS: m/z=580 (M+1).

EXAMPLES 130-132

Using procedures similar to that described in Example 1, the following compounds of formula I wherein $R^0$ is isopropyl and R and $R^6$ have the indicated values were prepared by oxidation of the corresponding alcohols of formula II.

EXAMPLE 130

R=4-pyridylmethoxycarbonyl, $R^6$=3-pyridyl: Chromatography solvent: methanol:dichloromethane (gradient, 5:95, 10:90); TLC: $R_f$=0.30, methanol:dichloromethane (10:90); 300 MHz NMR (DMSO/D$_2$O): 8.67 (m,2), 8.55 (m,2), 8.47 (s,1), 7.90 (m,2), 7.44 (m,3), 5.23 (s,2), 4.67 (m,2), 3.99 (m,1), 2.19 (m,1), 0.82 (d,3), 0.69 (d,3).

Analysis for $C_{24}H_{23}F_3N_6O_5.0.6H_2O$: Calculated: C, 53.1; H, 4.49; N, 15.5. Found: C, 53.0; H, 4.53; N, 15.5.

EXAMPLE 131

R=2,6-dimethylpyrid-4-ylmethoxycarbonyl, $R^6$=3,5-difluorophenyl: Chromatography solvent: tetrahydrofuran:dichloromethane (gradient, 15:85, 40:60); TLC: $R_f$=0.37, tetrahydrofuran:dichloromethane (25:75); NMR (DMSO/D$_2$O): 8.45 (s,1), 7.42 (t,1), 7.20 (d,2), 7.08 (s,2), 5.13 (s,2), 4.70 (d,1), 4.45 (d,1), 4.01 (d,1), 2.40 (s,6), 2.23 (m,1), 0.84 (d,3), 0.73 (d,3).

Analysis for $C_{27}H_{26}F_5N_5O_5.0.5H_2O$: Calculated: C, 53.6; H, 4.50; N, 11.6. Found: C, 53.4; H, 4.47; N, 11.6.

EXAMPLE 132

R=2,6-dimethylpyrid-4-ylmethoxycarbonyl, $R^6$=4-methoxyphenyl: Chromatography solvent: methanol:dichloromethane (5:95); TLC: $R_f$=0.21, methanol:dichloromethane (5:95); NMR (DMSO/D$_2$O): 8.44 (s,1), 7.45 (d,2), 7.11 (s,2), 6.99 (d,2), 5.16 (s,2), 4.60 (dd,2), 4.05 (d,1), 3.81 (s,3), 2.44 (s,6), 2.25 (m,1), 0.87 (d,3), 0.78 (d,3).

Analysis for $C_{28}H_{30}F_3N_5O_6.0.7H_2O$: Calculated: C, 55.9; H, 5.25; N, 11.6. Found: C, 55.7; H, 5.27; N, 11.7.

The intermediate alcohols of formula II, used in Examples 130-132, were prepared as follows.

EXAMPLES 130.a.–132.a.

Using procedures similar to that outlined in Example 2.a., the following compounds of formula XII wherein $R^0$ is isopropyl, Rp is tert-butyldimethylsilyl and $R^6$ has the indicated value were prepared from the corresponding compounds of formula II.

EXAMPLE 130.a.

$R^6$=3-pyridyl: Chromatography solvent: diethyl ether:hexane (gradient, 80:20 to 100:0); TLC: $R_f$=0.35, methanol:dichloromethane (5:95); MS: m/z=648(M+1).

EXAMPLE 131.a.

$R^6$=3,5-difluorophenyl: Purified by recrystallization from diethyl ether:hexane (1:1); TLC: $R_f$=0.6, tetrahydrofuran:dichloromethane (5:95); MS: m/z=683(M+1).

EXAMPLE 132.a.

$R^6$=4-methoxyphenyl: Chromatography solvent: ethyl acetate:dichloromethane (10:90); TLC: $R_f$=0.33, ethyl acetate:dichloromethane (10:90); MS: m/z=677(M+1).

EXAMPLES 130.b–132.b

The following compounds of formula XIII wherein $R^0$ is isopropyl, Rp is tert-butyldimethylsilyl and $R^6$ has the indicated value were prepared from the corresponding compounds of formula XII, described in Examples 130.a.–132.a., by procedures similar to that described in Example 2.b.

EXAMPLE 130.b.

$R^6$=3-pyridyl: Chromatography solvent: methanol:dichloromethane (gradient, 5:95, 10:90); TLC: $R_f$=0.20, methanol:dichloromethane (5:95); MS: m/z=514(M+1).

EXAMPLE 131.b.

$R^6$=3,5-difluorophenyl: Purified by recrystallization from diethyl ether:hexane (1:1); TLC: $R_f$=0.44, tetrahydrofuran:dichloromethane (15:85); MS: m/z=549(M+1).

EXAMPLE 132.b.

$R^6$=4-methoxyphenyl: Purified by recrystallization from diethyl ether:hexane (1:1); TLC: $R_f$=0.55, methanol:dichloromethane (10:90); MS: m/z=543(M+1).

EXAMPLES 130.c.–132.c.

The following compounds of formula XIV wherein $R^0$ is isopropyl, Rp is tert-butyldimethylsilyl and R and $R^6$ have the indicated values were prepared from the corresponding compounds of formula XIII, described in Examples 130.b.–132.b., by procedures similar to that described in Example 3.a., except using the required carbinol.

EXAMPLE 130.c.

R=4-pyridylmethoxycarbonyl, $R^6$=3-pyridyl: Chromatography solvent: methanol:dichloromethane (gradient, 5:95, 10:90); TLC: $R_f$=0.3, methanol:dichloromethane (7:93); MS: m/z=649(M+1).

EXAMPLE 131.c.

R=2,6-dimethylpyrid-4-ylmethoxycarbonyl, $R^6$=3,5-difluorophenyl: Chromatography solvent: tetrahydrofuran: dichloromethane (gradient, 5:95, 15:85); TLC: $R_f$=0.43, tetrahydrofuran:dichloromethane (10:90); MS: m/z=712(M+1).

EXAMPLE 132.c.

R=2,6-dimethylpyrid-4-ylmethoxycarbonyl, $R^6$=4-methoxyphenyl: Chromatography solvent: methanol:dichloromethane (5:95); TLC: $R_f$=0.25, methanol:dichloromethane (5:95); MS: m/z=706(M+1).

EXAMPLES 130.d.–132.d.

The following compounds of formula II wherein $R^0$ is isopropyl and R and $R^6$ have the indicated values were prepared from the corresponding compounds of formula XIV, described in Examples 130.c.–132.c., by procedures similar to that described in Example 2.d.

EXAMPLE 130.d.

R=4-pyridylmethoxycarbonyl, $R^6$=3-pyridyl: Chromatography solvent: methanol:dichloromethane (gradient, 5:95 to 10:90); TLC: $R_f$=0.45, methanol:dichloromethane (5:95); MS: m/z=535(M+1).

EXAMPLE 131.d.

R=2,6-dimethylpyrid-4-ylmethoxycarbonyl, $R^6$=3,5-difluorophenyl: Purified by crystallization from diethyl ether:tetrahydrofuran (4:1); TLC: $R_f$=0.17, tetrahydrofuran: dichloromethane (15:85); MS: m/z=598(M+1).

EXAMPLE 132.d.

R=2,6-dimethylpyrid-4-ylmethoxycarbonyl, $R^6$=4-methoxyphenyl: Chromatography solvent, methanol:dichloromethane (5:95); TLC: $R_f$=0.50, methanol:dichloromethane (10:90); MS: m/z=592(M+1).

EXAMPLES 133–134

Using procedures similar to that described in Example 1 the following compounds of formula I wherein $R^0$ is isopropyl and R and $R^6$ have the indicated values were prepared by oxidation of the corresponding alcohols of formula II.

EXAMPLE 133

R=ethoxycarbonyl, $R^6$=3-pyridyl: Chromatography solvent: methanol:dichloromethane (gradient, 4:96 to 8:92) TLC: $R_f$=0.44, tetrahydrofuran:dichloromethane (40:60); NMR (DMSO/$D_2O$): 8.88 (m,2), 8.45 (s,1), 7.90 (m,2), 7.45 (m,1), 4.73 (d,1), 4.50 (d,1), 4.15 (m,2), 3.99 (m,1), 2.20 (m,1), 1.23 (t,3), 0.82 (d,3), 0.70 (d,3).

Analysis for $C_{20}H_{22}F_3N_5O_5.0.6H_2O$: Calculated: C, 50.0; H, 4.87; N, 14.5. Found: C, 49.7; H, 4.88; N, 14.4.

EXAMPLE 134

R=isopropoxycarbonyl, $R^6$=3-pyridyl: Chromatography solvent: methanol:dichloromethane (gradient, 4:96, 8:92); TLC: $R_f$=0.50, tetrahydrofuran:dichloromethane (35:65); NMR (DMSO/$D_2O$): 8.69 (s,2), 8.45 (s,1), 7.91 (d,1), 7.46 (m,1), 4.87 (m,1), 4.6 (m,2), 4.00 (m,1), 2.20 (m,1), 1.26 (d,6), 0.82 (d,3), 0.70 (d,3).

Analysis for $C_{21}H_{24}F_3N_5O_5.1.0H_2O$: Calculated: C, 50.3; H, 5.22; N, 14.0. Found: C, 50.3; H, 5.16; N, 13.6.

The intermediate alcohols of formula II, used in Examples 133–134, were prepared as follows

EXAMPLES 133.a.–134.a.

The following compounds of formula XIV wherein $R^0$ is isopropyl, Rp is tert-butyldimethylsilyl and R and $R^6$ have the indicated values were prepared from the corresponding compounds of formula XIII and the indicated chloroformate using procedures similar to that described in Example 35.

EXAMPLE 133.a.

R=ethoxycarbonyl, $R^6$=3-pyridyl: Using ethyl chloroformate; chromatography solvent: tetrahydrofuran:dichloro-methane (gradient, 10:90 to 30:70); TLC: $R_f$=0.48, methanol:dichloromethane (10:90); MS: m/z=586(M+1).

EXAMPLE 134.a.

R=isopropoxycarbonyl, $R^6$=3-pyridyl: Using isopropyl chloroformate; chromatography solvent: tetrahydrofuran:dichloromethane (gradient, 10:90, 30:70); TLC: $R_f$=0.43, methanol:dichloromethane (10:90); MS: m/z=600(M+1).

EXAMPLES 133.b.–134.b.

The following compounds of formula II wherein $R^0$ is isopropyl, and R and $R^6$ have the indicated values were prepared from the corresponding compounds of formula XIV, described in Examples 133.a.–134.a., by procedures similar to that described in Example 2.d.

EXAMPLE 133.b.

R=ethoxycarbonyl, $R^6$=3-pyridyl: Chromatography solvent: methanol:dichloromethane (gradient, 4:96, 10:90); TLC: $R_f$=0.25, tetrahydrofuran:dichloromethane (35:65); MS: m/z=472(M+1).

EXAMPLE 134.b.

R=isopropoxycarbonyl, $R^6$=3-pyridyl: Chromatography solvent: methanol:dichloromethane (gradient, 4:96, 8:92); TLC: $R_f$=0.24, methanol:dichloromethane (8:92); MS: m/z=486(M+1).

EXAMPLE 135

2-[5-Amino-2-(4-hydroxyphenyl)-6-oxo-1,6-dihydro-1-pyrimidinyl]-N-(3,3,3-trifluoro-1-isopropyl-2-oxopropyl)acetamide To a suspension of the product from Example 28 (0.68 g) in dichloromethane (20 mL) was added boron tribromide (32 mL, 1M solution in dichloromethane) and the resulting solution was allowed to stir for 3 days. The excess boron tribromide was quenched by addition of methanol (5 mL) and the solution was brought to neutral pH by addition of sodium bicarbonate. The product was extracted into ethyl acetate, the solution dried, and the solvent was evaporated. The resulting material was purified by chromatography, eluting with methanol:dichloromethane (5:95), to give the title compound (0.4 g) as a white solid; TLC: $R_f$=0.3, methanol:dichloromethane (5:95); NMR (DMSO/$D_2O$): 7.32 (s,1), 7.22 (dd,2), 6.74 (dd,2), 4.48 (dd,2), 4.1 (m,1), 2.20 (m,1), 0.83 (d,3), 0.76 (d,3).

Analysis for $C_{18}H_{19}F_3N_4O_4$: Calculated: C, 52.4; H, 4.64; N, 13.6. Found: C, 52.4; H, 4.80; N, 13.3.

EXAMPLE 136

2-[5-Methylsulfonylamino-2-(4-nitrophenyl)-6-oxo-1,6-dihydro-1-pyrimidinyl]-N-(3,3,3-trifluoro-1-isopropyl-2-oxopropyl)acetamide The product from Example 33 was subjected to a procedure similar to that described in Example 115 to yield crude material, which was purified by trituration with ether, to give the title compound as a white solid; TLC: $R_f$=0.4, methanol:dichloromethane (5:95); NMR (DMSO/$D_2O$): 8.29 (d,2), 7.97 (s,1), 7.70 (d,2), 4.55 (m,2), 3.92 (d,1), 3.08 (s,3), 2.13 (m,1), 0.73 (d,3), 0.64 (d,3).

Analysis for $C_{19}H_{20}F_3O_7N_5S$: Calculated: C, 43.9; H, 3.88; N, 13.5. Found: C, 43.8; H, 3.95; N, 13.3.

EXAMPLE 137

2-[5-Phenylsulfonylamino-2-(4-methoxyphenyl)-6-oxo-1,6-dihydro-1-pyrimidinyl]-N-(3,3,3-trifluoro-1-isopropyl-2-oxopropyl)acetamide The product from Example 28 was subjected to a procedure similar to that described in Example 115 substituting phenyl sulfonylchloride for methyl sulfonyl chloride to give the title compound as a white solid; chromatography solvent: methanol:dichloromethane (5:95); TLC: $R_f$=0.38, methanol:dichloromethane (5:95); NMR: 10.06 (s,1), 8.81 (d,1), 7.91 (m,3), 7.61 (m,3), 7.40 (d,2), 6.99 (d,2), 4.64 (t,1), 4.50 (dd,2), 3.80 (s,3), 2.15 (m,1), 0.88 (d,3), 0.82 (d,3).

Analysis for $C_{25}H_{25}F_3N_4O_6S$: Calculated: C, 53.00; H, 4.45; N, 9.89. Found: C, 52.95; H, 4.61; N, 9.86.

EXAMPLE 138

2-[2-(4-Fluorophenyl)-6-oxo-5-ureido-1,6-dihydro-1-pyrimidinyl]-N-(3,3,3-trifluoro-1-isopropyl-2-oxopropyl)acetamide A flask was charged with 0.4 g of the product from Example 15 dissolved in a mixture of water (6 mL), tetrahydrofuran (1 mL) and acetic acid (4 mL) at room temperature. To this was added 0.31 g sodium isocyanate and the reaction mixture stirred for 1.5 h at room temperature and then 0.5 h at 55° C. Additional sodium isocyanate, 2×70 mg and 1×35 mg, was sequentially added over an additional 1 h. The mixture was cooled, diluted with ethyl acetate, and partitioned with water. The organic layer was dried over sodium sulfate, filtered and evaporated to afford a residual solid which was triturated with diethyl ether. The residual solid was collected and dried under vacuum to afford the title compound (200 mg) as an off-white solid; TLC: $R_f$=0.20, dichloromethane:methanol (15:1); NMR (DMSO/$D_2O$): 8.65 (s,1), 7.54 (m,2), 7.28 (m,2), 4.56 (dd,2), 4.05 (d,1), 2.24 (m,1), 0.82 (dd,6); MS: m/z=458(M+1).

Analysis for $C_{19}H_{19}F_4N_5O_4 \cdot 0.75H_2O$: Calculated: C, 48.46; H, 4.39; N, 14.87. Found: C, 48.10; H, 4.21; N, 15.16.

EXAMPLES 139-153

Using procedures similar to that described in Example 90 and using the required acyl or sulfonyl chloride, the following compounds of formula I wherein $R^0$ is isopropyl and R and $R^6$ have the indicated values were prepared from the corresponding compounds of formula I wherein R is hydrogen.

EXAMPLE 139

R=methoxyaminocarbonyl, $R^6$=phenyl: Chromatography solvent: dichloromethane:methanol (3:1) followed by trituration with dichloromethane:diethyl ether; TLC: $R_f$=0.29, dichloromethane:methanol (20:1); NMR (DMSO/$D_2O$): 8.63 (s,1), 7.47 (m,5), 4.63 (d,1), 4.06 (d,1), 2.34 (m,1), 0.85 (d,3), 0.77 (d,3); MS: m/z=470(M+1).

Analysis for $C_{20}H_{22}F_3N_5O_5 \cdot 0.5H_2O$: Calculated: C, 50.21; H, 4.84; N, 14.64. Found: C, 50.33; H, 4.54; N, 14.26.

EXAMPLE 140

R=acetylaminosulfonyl, $R^6$=4-fluorophenyl: Purified by crystallization from diethyl ether; TLC: $R_f$=0.14, chloroform:methanol (6:1); NMR (DMSO/$D_2O$): 7.99 (s,1), 7.53 (dd,2), 7.28 (t,2), 4.67 (d,1), 4.50 (d,1), 2.2 (m,1), 1.95 (s,3), 0.84 (d,3), 0.74 (d,3); MS: FAB m/z=536(M+1), m/z=534(M−1).

Analysis for $C_{20}H_{21}F_4N_5O_6S$: Calculated: C, 44.86; H, 3.95; N, 13.08. Found: C, 45.19; H, 4.00; N, 13.21.

EXAMPLE 141

R=acetylaminosulfonyl, $R^6$=phenyl: Purified by crystallization from diethyl ether; TLC: $R_f$=0.23, chloroform:methanol (6:1); NMR (DMSO/$D_2O$): 8.00 (s,1), 7.57-747 (m,5), 4.61 (d,1), 4.50 (d,1), 2.24 (m,1), 1.96 (s,3), 0.85 (d,3), 0.77 (d,3); MS: FAB m/z=518(M+1), 516(M−1); High resolution exact mass analysis for $C_{20}H_{23}F_3N_5O_6S$ (M+1): Calculated: m/z=518.1321, Found: m/z=518.1319.

Analysis for $C_{20}H_{22}F_3N_5O_6S$: Calculated: C, 46.42; H, 4.28; N, 13.53. Found: C, 46.85; H, 4.42; N, 13.60.

EXAMPLE 142

R=benzoylaminosulfonyl, $R^6$=phenyl: Purified by crystallization from ethyl acetate:ether; TLC: $R_f$=0.18, chloroform:methanol (6:1); NMR (DMSO/$D_2O$): 8.07 (s,1), 7.84 (m,2), 7.64 (m,1), 7.54–7.45 (m,7), 4.60 (d,1), 4.46 (d,1), 2.20 (m,1), 0.82 (d,3), 0.72 (d,3); MS: FAB m/z=580(M+1), m/z=578(M−1).

Analysis for $C_{25}H_{24}F_3N_5O_6S \cdot 0.7H_2O$: Calculated: C, 50.71; H, 4.32; N, 11.83. Found: C, 50.62; H, 4.33; N, 11.82.

EXAMPLE 143

R=methoxycarbonylaminosulfonyl, $R^6$=2-thienyl: Purified by trituration with methyl tert-butyl ether; TLC: $R_f$=0.14, chloroform:methanol (6:1); NMR (DMSO/$D_2O$): 7.97 (s,1), 7.82 (d,1), 7.43 (d,1), 7.15 (dd,1), 4.89 (dd,2), 3.64 (s,3), 2.26 (m,1), 0.93 (d,3), 0.78 (d,3); MS: FAB m/z=540(M+1), 538(M−1).

Analysis for $C_{18}H_{20}F_3N_5O_7S_2$: Calculated: C, 40.07; H, 3.74; N, 12.98. Found: C, 39.91; H, 3.74; N, 12.87.

EXAMPLE 144

R=4-acetylaminophenylsulfonyl, $R^6$=4-fluorophenyl: Purified by trituration with diethyl ether; TLC: $R_f$=0.22, dichloromethane:methanol (20:1); NMR (DMSO/$D_2O$): 7.93 (s,1), 7.85 (d,2, J=8.0), 7.74 (d,2, J=8.0), 7.51 (m,2), 7.25 (dd,2, J=8.8, 6.8), 4.60 (d,1, J=17.0), 4.39 (d,1, J=16.8), 3.99 (m,1), 2.20 (m,1), 2.09 (s,3), 0.82 (d,3, J=6.4), 0.71 (d,3, J=6.4); MS: m/z=612(M+1).

Analysis for $C_{26}H_{25}F_4N_5O_6S \cdot 0.5H_2O$: Calculated: C, 50.32; H, 4.22; N, 11.28. Found: C, 50.19; H, 4.15; N, 11.24.

EXAMPLE 145

R=4-acetylaminophenylsulfonyl, $R^6$=phenyl: Purified by trituration with diethyl ether; TLC: $R_f$=0.25, dichloromethane:methanol (20:1); NMR (DMSO/$D_2O$): 7.94 (s,1), 7.86 (d,2, J=8.8), 7.74 (d,2, J=8.8), 7.53 (m,1), 7.45 (m,4), 4.56 (d,1, J=16.8), 4.37 (d,1, J=16.8), 4.02 (d,1, J=2.8), 2.21 (m,1), 2.09 (s,3), 0.80 (d,3, J=6.8); 0.74 (d,3, J=6.8); MS: m/z=594(M+1).

Analysis for $C_{26}H_{26}F_3N_5O_6S$: Calculated: C, 52.21; H, 4.46; N, 11.71. Found: C, 52.24; H, 4.52; N, 11.66.

EXAMPLE 146

R=4-acetylaminophenylsulfonyl, $R^6$=2-thienyl: Purified by recrystallization from ethyl acetate; TLC: $R_f$=0.47, dichloromethane:methanol (10:1); NMR (DMSO/$D_2O$): 7.91 (s,1), 7.83 (d,2, J=8.8), 7.81 (d,1, J=4.7), 7.74 (d,2, J=8.8), 7.38 (d,1, J=4.7), 7.12 (dd,1, J=4.2, 4.6), 4.86 (d,1, J=16.6), 4.74 (d,1, J=16.6), 4.06 (d,1, J=2.7), 2.24 (m,1), 2.09 (s,3), 0.90 (d,3, J=6.8), 0.74 (d,3, J=6.8); MS: m/z=600(M+1).

Analysis for $C_{24}H_{24}F_3N_5O_6S_2 \cdot 0.5H_2O$: Calculated: C, 47.36; H, 4.14; N, 11.51. Found: C, 47.58; H, 4.06; N, 11.56.

EXAMPLE 147

R=benzoylaminosulfonyl, $R^6$=2-thienyl: Purified by trituration with ethyl acetate:diethyl ether; TLC: $R_f$=0.14, dichloromethane:methanol (10:1); NMR (DMSO/$D_2O$): 8.04 (s,1), 7.84 (m,3), 7.65 (dd,1, J=7.2, 7.5), 7.52 (dd,2, J=7.5, 7.8), 7.42 (d,1, J=3.6), 7.13 (dd,1, J=4.0, 4.9), 4.91 (d,1, J=16.8), 4.80 (d,1, J=16.8), 4.08 (d,1, J=2.8), 2.24 (m,1), 0.91 (d,3, J=6.8), 0.74 (d,3, J=6.8); MS: m/z=586(M+1).

Analysis for $C_{23}H_{22}F_3N_5O_6S_2 \cdot 0.5H_2O$: Calculated: C, 46.46; H, 3.90; N, 11.78. Found: C, 46.63; H, 3.85; N, 11.79.

EXAMPLE 148

R=benzylaminosulfonyl, $R^6$=2-thienyl: Purified by trituration with hexane:diethyl ether (20:1); TLC: $R_f$=0.42, dichloromethane:methanol (20:1); NMR (DMSO/$D_2O$): 7.90 (s,1), 7.82 (d,1), 7.40 (d,1), 7.38 (m,5), 7.15 (t,1), 4.83 (q,2), 4.11 (s,2), 2.28 (m,1), 0.95 (d,3), 0.80 (d,3); MS: m/z=572(M+1) also exact mass for $C_{23}H_{24}F_3N_5O_5S_2$, Calculated: 571.1171, Found: 571.1170.

Analysis for $C_{23}H_{24}F_3N_5O_5S_2$: Calculated: C, 48.33; H, 4.23; N, 12.25. Found: C, 48.52; H, 4.19; N, 11.68.

EXAMPLE 149

R=2,2,2-trifluoroethylsulfonyl, $R^6$=2-thienyl: Purified by trituration with diethyl ether; TLC: $R_f$=0.79, dichloromethane:tetrahydrofuran:acetic acid (90:10:1); NMR (DMSO/$D_2O$): 8.01 (s,1), 7.87 (dd,1, J=5.1, 0.9), 7.48 (dd,1, J=3.8, 0.9), 7.16 (dd,1, J=5.1, 3.8), 4.96 (d,1, J=16.8), 4.84 (d,1, J=16.8), 4.57 (q,2, J=9.8), 4.10 (d,1, J=2.9), 2.26 (m,1), 0.93 (d,3, J=6.8), 0.78 (d,3, J=6.8); MS: m/z=549(M+1).

Analysis for $C_{18}H_{18}F_6N_4O_5S_2$: Calculated: C, 39.42; H, 3.36; N, 10.22. Found: C, 39.30; H, 3.36; N, 10.20.

EXAMPLE 150

R=2,2,2-trifluoroethylaminosulfonyl, $R^6$=2-thienyl: Purified by trituration with diethyl ether; TLC: $R_f$=0.56, dichloromethane:tetrahydrofuran:acetic acid (90:10:1); NMR (DMSO/$D_2O$): 7.95 (s,1), 7.84 (dd,1, J=1.0, 5.1), 7.42 (dd,1, J=1.0, 3.8), 7.15 (dd,1, J=3.8, 5.1), 4.94 (d,1, J=16.8), 4.82 (d,1, J=16.8), 4.10 (d,1, J=2.8), 3.70 (q,2, J=9.6), 2.28 (m,1), 0.94 (d,3, J=6.8), 0.79 (d,3, J=6.8); MS: m/z=564(M+1).

Analysis for $C_{18}H_{19}F_6N_5O_5S_2 \cdot 0.5H_2O$: Calculated: C, 37.76; H, 3.52; N, 12.23. Found: C, 37.85; H, 3.48; N, 12.26.

EXAMPLE 151

R=cyanomethylsulfonyl, $R^6$=2-thienyl: Purified by trituration with diethyl ether containing a trace of ethyl acetate; TLC: $R_f$=0.36, dichloromethane:methanol (90:10); NMR (DMSO/$D_2O$): 8.02 (s,1), 7.88 (dd,1, J=0.9, 5.1), 7.48 (dd,1, J=0.9, 3.8), 7.17 (dd,1, J=3.8, 5.1); 4.97 (d,1, J=16.9), 4.86 (d,1, J=16.9), 4.10 (d,1, J=2.8), 2.27 (m,1), 0.94 (d,3, J=6.8), 0.78 (d,3, J=6.8); MS: m/z=506(M+1).

Analysis for $C_{18}H_{18}F_3N_5O_6S$: Calculated: C, 42.77; H, 3.59; N, 13.85. Found: C, 42.63; H, 3/59; N, 13.90.

EXAMPLE 152

R=cyanomethylsulfonyl, $R^6$=4-fluorophenyl: Purified by trituration with diethyl ether containing a trace of ethyl acetate; TLC: $R_f$=0.33, dichloromethane:methanol (90:10); NMR(DMSO/$D_2O$): 8.04 (s,1), 7.58 (m,2), 7.31 (m,2), 4.70 (d,1, J=16.8), 4.50 (d,1, J=16.8), 4.03 (broad s,1), 2.23 (m,1), 0.85 (d,3, J=6.4), 0.74 (d,3, J=6.4); MS: m/z=518(M+1).

Analysis for $C_{20}H_{19}F_4N_5O_5S \cdot 1.0H_2O$: Calculated: C, 44.86; H, 3.95; N, 13.08. Found: C, 44.97; H, 3.67; N, 13.02.

EXAMPLE 153

R=2,2,2-trifluoroethylsulfonyl, $R^6$=4-fluorophenyl: Purified by trituration with diethyl ether containing a trace of ethyl acetate; TLC: $R_f$=0.59, dichloromethane:methanol (90:10); NMR (DMSO/$D_2O$): 7.99 (s,1), 7.56 (dd,2, J=5.4, 5.4), 7.29 (t,2, J=8.8), 4.74 (d,1, J=18) 4.47 (d,1, J=18), 4.04 (d,1, J=2.6), 3.71 (q,2, J=9.4), 2.23 (m,1), 0.85 (d,3, J=6.8), 0.75 (d, J=6.8); MS: m/z=576(M+1).

Analysis for $C_{20}H_{20}F_7N_5O_5S.0.5H_2O$: Calculated: C, 41.10; H, 3.62; N, 11.98. Found: C, 40.98; H, 3.56; N, 11.92.

EXAMPLE 154

2-[5-(2,6-Dimethylpyrid-4-ylmethoxycarbonylamino)-6-oxo-2-(2-thienyl)-1,6-dihydro-1-pyrimidinyl]-N-(3,3,3-trifluoro-1-isopropyl-2-oxopropyl)acetamide Using a similar procedure to that described in Example 1, 2-[5-(2,6-dimethylpyrid-4-ylmethoxycarbonylamino)-6-oxo-2-(2-thienyl)-1,6-dihydro-1-pyrimidinyl]-N-(3,3,3-trifluoro-2-hydroxy-1-isopropylpropyl)acetamide was oxidized to afford the title compound, obtained as a yellow solid; TLC: $R_f$=0.4, methanol:dichloromethane (5:95); 300 MHz NMR (DMSO/$D_2O$): 8.38 (s,1), 7.74 (d,1), 7.34 (d,1), 7.03 (m,3), 5.10 (s,2), 4.82 (m,2), 4.02 (d,1), 3.95 (m,2), 2.38 (s,6), 2.22 (m,1), 0.87 (d,3), 0.74 (d,3).

Analysis for $C_{25}H_{26}F_3N_5O_5S.0.25H_2O$ Calculated: C, 52.7; H, 4.63; N, 12.4. Found: C, 52.7; H, 4.66; N, 12.2.

The intermediate 2-[5-(2,6-dimethylpyrid-4-ylmethoxycarbonylamino)-6-oxo-2-(2-thienyl)-1,6-dihydro-1-pyrimidinyl]-N-(3,3,3-trifluoro-2-hydroxy-1-isopropylpropyl)acetamide was prepared as follows:

a. 2-[5-Benzyloxycarbonylamino-6-oxo-2-(2-thienyl)-1,6-dihydro-1-pyrimidinyl]-N-(3,3,3-trifluoro-1-isopropyl-2-pivaloyloxypropyl)acetamide To a solution of 2-[5-benzyloxycarbonylamino-6-oxo-2-(2-thienyl)-1,6-dihydro-1-pyrimidinyl]-N-(3,3,3-trifluoro-2-hydroxy-1-isopropylpropyl)acetamide (1.95 g), triethylamine (1.4 mL), and 4-dimethylaminopyridine (10 mg) in dichloromethane (35 mL) was added pivaloyl chloride (0.53 mL); and the resulting solution allowed to stir for 2 h. The solution was diluted with ethyl acetate, washed (saturated aqueous sodium bicarbonate (twice), saturated aqueous ammonium chloride, and brine), dried, and evaporated. Purification by chromatography, eluting with ethyl acetate:dichloromethane (10:90), afforded the ester (1.80 g) as a white foam; TLC: $R_f$=0.34, ethyl acetate:dichloromethane (10:90); MS: m/z=623(M+1).

b. 2-[5-Amino-6-oxo-2-(2-thienyl)-1,6-dihydro-1-pyrimidinyl]-N-(3,3,3-trifluoro-1-isopropyl-2-pivaloyloxypropyl)acetamide Using a procedure similar to that described in Example 12, 2-[5-benzyloxycarbonylamino-6-oxo-2-(2-thienyl)-1,6-dihydro-1-pyrimidinyl]-N-(3,3,3-trifluoro-1-isopropyl-2-pivaloyloxypropyl)acetamide was deprotected to afford the amine, obtained as a yellow foam; TLC: $R_f$=0.5, ethyl acetate; MS: m/z=489(M+1).

c. 2-[5-(2,6-Dimethylpyrid-4-ylmethoxycarbonylamino)-6-oxo-2-(2-thienyl)-1,6-dihydro-1-pyridinyl]-N-(3,3,3-trifluoro-1-isopropyl-2-pivaloyloxypropyl)acetamide Using a procedure similar to that described in Example 3.a., but using 2,6-dimethylpyrid-4-ylcarbinol, 2-[5-amino-6-oxo-2-(2-thienyl)-1,6-dihydro-1-pyrimidinyl]-N-(3,3,3-trifluoro-1-isopropyl-2-pivaloyloxypropyl-)acetamide was acylated to provide the urethane, obtained as yellow foam; TLC: $R_f$=0.36, ethyl acetate; MS: m/z=652(M+1).

d. 2-[5-(2,6-Dimethylpyrid-4-ylmethoxycarbonylamino)-6-oxo-2-(2-thienyl)-1,6-dihydro-1-pyrimidinyl]-N-(3,3,3-trifluoro-2-hydroxy-1-isopropylpropyl)acetamide To a solution of 2-[5-(2,6-dimethylpyrid-4-ylmethoxycarbonylamino)-6-oxo-2-(2-thienyl)-1,6-dihydro-1-pyridinyl]-N-(3,3,3-trifluoro-1-isopropyl-2-pivaloyloxypropyl)acetamide (1.44 g) in tetrahydrofuran (10 mL) and methanol (10 mL) was added a solution of lithium hydroxide monohydrate (0.92 g) in water (20 mL). The resulting solution was stirred for 2 h, diluted with saturated ammonium chloride (30 mL), and extracted with ethyl acetate. The ethyl acetate solution was dried and evaporated. The resulting material was chromatographed, eluting with ethyl acetate, to provide the alcohol (0.39 g) as a yellow foam; TLC: $R_f$=0.24, ethyl acetate; MS: m/z=568(M+1).

EXAMPLE 155

2-[5-Ethylamino-2-(4-methoxyphenyl)-6-oxo-1,6-dihydro-1-pyrimidinyl]-N-(3,3,3-trifluoro-1-isopropyl-2-oxopropyl)acetamide Using a procedure similar to that described in Example 80, the title compound was prepared from the product of Example 28. Chromatography solvent: dichloromethane:methanol (gradient, 99.5:0.5, 99.3:0.7), then triturated with hexane:diethyl ether (80:20); TLC: $R_f$=0.41, dichloromethane:acetone (70:30); NMR: 0.73-1.03 (m,6), 1.17 (t,3), 2.07-2.27 (m,1), 3.03-3.20 (m,2), 3.79 (s,3), 4.03-4.73 (m,3), 5.30-5.43 (m,1), 6.96 (d,2), 7.10 (s,1), 7.30-7.47 (m,2), 8.80 (d,1); MS: m/z=455(M+1).

Analysis for $C_{21}H_{25}F_3N_4O_4.0.2H_2O$: Calculated: C, 55.06; H, 5.58; N, 12.23. Found: C, 55.43; H, 5.64; N, 11.80.

EXAMPLES 156-159

Using a procedure similar to that described in Example 89, the following compounds of formula I wherein $R^0$ is isopropyl, R is formyl and $R^6$ is the indicated group were prepared from the corresponding compounds of formula I wherein R is hydrogen.

EXAMPLE 156

$R^6$=4-methoxyphenyl: Chromatography solvent: dichloromethane:methanol (gradient, 99.5:0.5, 97.5:2.5); TLC: $R_f$=0.46, dichloromethane:acetone (70:30); NMR: 0.73-1.00 (m,6), 2.03-2.30 (m,1), 3.81 (s,3), 4.02-4.77 (m,3), 6.87-7.07 (m,2), 7.43 (d,2), 8.36 (s,1), 8.80-8.93 (m,2), 10.00 (s,1); MS: m/z=455(M+1).

Analysis for $C_{20}H_{21}F_3N_4O_5.0.3H_2O$: Calculated: C, 52.24; H, 4.73; N, 12.18. Found: C, 52.24; H, 4.73; N, 12.07.

EXAMPLE 157

$R^6$=2-thienyl: Chromatography solvent: dichloromethane:methanol (gradient, 99.5:0.5, 97.5:2.5); TLC: $R_f$=0.55, dichloromethane:acetone (70:30); NMR: 0.73-1.17 (m,6), 2.13-2.33 (m,1), 4.07-5.07 (m,3), 7.10-7.23 (m,1), 7.30-7.47 (m,1), 7.77-7.90 (m,1), 8.36 (s,1), 8.88 (d,1), 9.05 (d,1), 10.07 (s,1); MS: m/z=431(M+1).

Analysis for $C_{17}H_{17}F_3N_4O_4S.0.3H_2O$: Calculated: C, 46.85; H, 4.07; N, 12.85. Found: C, 46.83; H, 4.05; N, 12.62.

EXAMPLE 158

$R^6$=4-fluorophenyl: Chromatography solvent: dichloromethane:methanol (gradient, 99.5:0.5, 97.5:2.5), then re-chromatographed with dichloromethane:acetone (80:20); TLC: $R_f$=0.47, dichloromethane:acetone (70:30); NMR: 0.60–1.03 (m,6), 2.03–2.27 (m,1), 4.00–4.77 (m,3), 7.27–7.43 (m,2), 7.50–7.70 (m,2), 8.37 (s,1), 9.70–9.90 (m,2), 10.07 (s,1); MS: m/z=443(M+1).

Analysis for $C_{19}H_{18}F_4N_4O_4.0.5H_2O$: Calculated: C, 50.55; H, 4.24; N, 12.41. Found: C, 50.52; H, 4.31; N, 12.20.

EXAMPLE 159

$R^6$=phenyl: Chromatography solvent: dichloromethane:methanol (gradient, 99.5:0.5, 97.5:2.5); TLC: $R_f$=0.51, dichloromethane:acetone (70:30); NMR: 0.73–1.00 (m,6), 2.07–2.30 (m,1), 4.07–4.77 (m,3), 7.37–7.60 (m,5), 8.37 (s,1), 8.85 (d,2), 10.07 (s,1); MS: m/z=425(M+1).

Analysis for $C_{19}H_{19}F_3N_4O_4$: Calculated: C, 53.77; H, 4.51; N, 13.20. Found: C, 53.43; H, 4.63; N, 12.94.

EXAMPLES 160–161

Using a procedure similar to that described in Example 90 but using 4-nitrobenzylaminosulfonyl chloride, the following compounds of formula I wherein $R^0$ is isopropyl, R is 4-nitrobenzylaminosulfonyl and $R^6$ is the indicated group were prepared from the corresponding compounds of formula I wherein R is hydrogen.

EXAMPLE 160

$R^6$=2-thienyl: Chromatography solvent: dichloromethane:methanol (gradient, 99.5:0.5, 98:2); TLC: $R_f$=0.36, dichloromethane:methanol (98:2); NMR: 0.77–1.13 (m,6), 2.17–2.30 (m,1), 4.26 (d,2), 4.70–5.00 (m,3), 7.13–7.20 (m,1), 7.32 (d,1), 7.54 (d,2), 7.86 (d,1), 7.92 (s,1), 8.14 (d,2), 8.27–8.37 (m,1), 9.03 (d,1), 9.24 (s,1); MS: m/z=617(M+1).

Analysis for $C_{23}H_{23}F_3N_6O_7S_2$: Calculated: C, 44.87; H, 3.60; N, 13.65. Found: C, 44.63; H, 3.82; N, 13.70.

EXAMPLE 161

$R^6$=phenyl: Chromatography solvent: dichloromethane:methanol 99.5:0.5, 98:2); TLC: $R_f$=0.35, dichloromethane:methanol (98:2); NMR: 0.70–0.93 (m,6), 2.10–2.30 (m,1), 4.27 (d,2), 4.03–4.70 (m,3), 7.43–7.63 (m,7), 7.95 (s,1), 8.17 (d,2), 8.33–8.43 (m,1), 8.84 (d,1), 9.24 (s,1); MS: m/z=611(M+1).

Analysis for $C_{25}H_{25}F_3N_6O_7S.0.3H_2O$: Calculated: C, 48.74; H, 4.18; N, 13.64. Found: C, 48.69; H, 4.11; N, 13.60.

The intermediate 4-nitrobenzylaminosulfonyl chloride was prepared from 4-nitrobenzylamine hydrochloride and sulfuryl chloride at reflux in acetonitrile. The solvent was evaporated and the crude material used without further purification.

EXAMPLE 162

2-[5-(4-Acetylaminobenzylaminosulfonylamino)-6-oxo-2-thienyl-1,6-dihydro-1-pyrimidinyl]-N-(3,3,3-trifluoro-1-isopropyl-2-oxopropyl)acetamide.

To a solution of 2-[5-(4-nitrobenzylaminosulfonylamino)-6-oxo-2-thienyl-1,6-dihydro-1-pyrimidinyl]-N-(3,3,3-trifluoro-1-isopropyl-2-oxopropyl)acetamide (0.431 g) in acetic acid (12 mL) was added acetic anhydride (0.265 mL), followed by iron powder (0.783 g). The reaction was stirred at room temperature overnight. Methanol was added and the reaction mixture filtered through diatomaceous earth to remove excess iron. Ethyl acetate was added and the resultant solution washed (water (twice), brine), dried (MgSO4) and evaporated. The crude material was purified by chromatography, with dichloromethane:methanol (gradient, 99.5:0.5, 98:2) as the eluent, to provide the title compound (0.247 g); TLC: $R_f$=0.27, dichloromethane:methanol (98:2); NMR: 0.87–0.97 (m,6), 2.17–2.30 (m,1), 3.32 (s,3), 4.02 (d,2), 4.73–4.77 (m,1) 4.77–4.93 (m,2), 7.13–7.20 (m,3), 7.33 (d,1), 7.47 (d,2), 7.80–7.87 (m,1), 7.91 (s,1), 7.97–8.03 (m,1), 9.04 (d,1), 9.09 (s,1), 9.87 (s,1); MS: m/z=629(M+1).

Analysis for $C_{25}H_{27}F_3N_6O_6S_2.0.4H_2O$ Calculated: C, 47.22; H, 4.40; N, 13.21. Found: C, 47.17; H, 4.26; N, 13.11.

EXAMPLE 163

2-[2-(4-Acetylaminophenyl)-5-benzyloxycarbonylamino-6-oxo-1,6-dihydro-1-pyrimidinyl]-N-(3,3,3-trifluoro-1-isopropyl-2-oxopropyl)acetamide 2-[5-Benzyloxycarbonylamino-2-(4-nitrophenyl)-6-oxo-1,6-dihydro-1-pyrimidinyl]-N-(3,3,3-trifluoro-1-isopropyl-2-oxopropyl)acetamide (2.01 g) was reductively acetylated using a similar procedure to that described in Example 162. The crude material was purified by chromatography, with dichloromethane:methanol (gradient 99.5:0.5, 98:2) as the eluent, to provide the title compound (1.51 g) as a white solid; TLC: $R_f$=0.47, dichloromethane:acetone (70:30); NMR: 0.77–1.00 (m,6), 2.00–2.33 (m,1), 2.07 (s,3), 4.03–4.73 (m,3), 5.17 (s,2), 7.30–7.53 (m,7), 7.60–7.77 (m,2), 8.43 (s,1), 9.83–9.03 (m,2), 10.19 (d,1); MS: m/z=588(M+1).

Analysis for $C_{28}H_{28}F_3N_5O_6.0.7H_2O$ Calculated: C, 56.03; H, 4.93; N, 11.66. Found: C, 56.00; H, 5.03; N, 11.45.

EXAMPLE 164

2-[5-Benzyloxycarbonylamino-2-(4-formylaminophenyl)-6-oxo-1,6-dihydro-1-pyrimidinyl]-N-(3,3,3-trifluoro-1-isopropyl-2-oxopropyl)acetamide To a solution of 2-[5-benzyloxycarbonylamino-2-(4-nitrophenyl)-6-oxo-1,6-dihydro-1-pyrimidinyl]-N-(3,3,3-trifluoro-1-isopropyl-2-oxopropyl)acetamide (2.02 g) in 90% aqueous formic acid (56 mL) was added iron powder (3.9 g). The mixture was stirred at room temperature overnight. Methanol was added and the reaction mixture filtered through diatomaceous earth to remove the excess iron. Ethyl acetate was added and the resultant solution washed with water (twice), brine, then dried (MgSO4) and evaporated. The crude material was purified by chromatography, with dichloromethane:methanol (gradient, 99.5:0.5, 98:2) as the eluent, followed by trituration with hexane:diethyl ether (80:20), to provide the title compound (1.12 g) as an off-white solid; TLC: $R_f$=0.39, dichloromethane:acetone (70:30); NMR: 0.67–1.03 (m,6), 2.03–2.33 (m,1), 4.00–4.80 (m,3), 5.17 (s,2), 7.20–7.60 (m,7), 7.57–7.77 (m,2), 8.22 (s,1), 8.43 (s,1), 8.83–9.07 (m,2), 10.30–10.57 (m,1); MS: m/z=574(M+1).

Analysis for $C_{27}H_{26}F_3N_5O_6.0.6H_2O$ Calculated: C, 55.49; H, 4.69; N, 11.98. Found: C, 55.64; H, 4.86; N, 11.59.

EXAMPLES 165–167

Using a procedure similar to that described in Example 12, the following compounds of formula I wherein $R^0$ is isopropyl, R is hydrogen, and $R^6$ is the indicated group were prepared from the corresponding compounds of formula I wherein R is benzyloxycarbonyl.

EXAMPLE 165

$R^6$=4-acetylaminophenyl: After the addition of sodium bicarbonate the product precipitated and was collected by filtration. The crude product was purified by trituration with hexane:diethyl ether (70:30) followed by chromatography, eluting with dichloromethane:methanol (gradient 95:5, 90:10); TLC: $R_f$=0.06, dichloromethane:methanol (98:2); NMR (DMSO/D$_2$O): 0.81 (d,3), 0.88 (d,3), 2.17–2.30 (m,1), 4.08 (s,1), 4.40–4.67 (m,2), 7.37 (d,3), 7.60 (d,2); MS: m/z=454(M+1).

Analysis for $C_{20}H_{22}F_3N_5O_4 \cdot 0.7H_2O \cdot 0.4CH_3OH$: Calculated: C, 51.16; H, 5.26; N, 14.62. Found: C, 51.45; H, 5.31; N, 14.19.

EXAMPLE 166

$R^6$=4-formylamino: After the addition of sodium bicarbonate the product precipitated and was collected by filtration. The crude product was purified by trituration with hexane:diethyl ether (70:30) followed by chromatography, eluting with dichloromethane:methanol (gradient 95:5, 90:10); TLC: $R_f$=0.05, dichloromethane:methanol (95:5); NMR (DMSO/D$_2$O): 0.77 (d,3), 0.87 (d,3), 2.17–2.30 (m,1), 4.03–4.10 (m,1), 4.40–4.67 (m,2), 7.37–7.47 (m,3), 7.61 (d,2), 8.30 (s,1); MS: m/z=440(M+1).

Analysis for $C_{19}H_{20}F_3N_5O_4 \cdot 0.6H_2O \cdot 0.4CH_3OH$: Calculated: C, 50.32; H, 4.96; N, 15.12. Found: C, 50.31; H, 4.93; N, 15.15.

EXAMPLE 167

$R^6$=4-trifluoroacetylaminophenyl: After addition of sodium bicarbonate the product precipitated and was collected by filtration. The crude product was purified by trituration with hexane:diethyl ether (70:30) followed by chromatography, eluting with dichloromethane:methanol (gradient, 95:5, 90:10); TLC: $R_f$=0.10, dichloromethane:methanol (95:5); NMR (DMSO/D$_2$O): 0.70–1.03 (m,6), 2.17–2.33 (m,1), 4.00–4.13 (m,1), 4.37–4.70 (m,2), 7.37 (s,1), 7.48 (d,2), 7.72 (d,2); MS: m/z=508(M+1).

Analysis for $C_{20}H_{19}F_6N_5O_4 \cdot 0.5H_2O$: Calculated: C, 46.51; H, 3.90; N, 13.56. Found: C, 46.62; H, 3.93; N, 13.29.

The intermediate 2-[5-benzyloxycarbonylamino-6-oxo-2-(4-trifluoroacetylaminophenyl)-1,6-dihydro-1-pyrimidinyl]-N-(3,3,3-trifluoro-1-isopropyl-2-oxopropyl)acetamide, which is also an Example of the invention, was prepared from 2-[5-benzyloxycarbonylamino-2-(4-nitrophenyl)-6-oxo-1,6-dihydro-1-pyrimidinyl]-N-(3,3,3-trifluoro-1-isopropyl-2-oxopropyl)acetamide using a procedure similar to that described in Example 165 but employing trifluoroacetic acid in place of acetic acid and trifluoroacetic anhydride in place of acetic anhydride.

FORMULAE

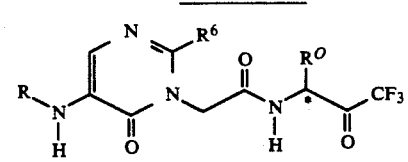

I

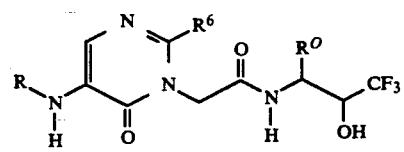

II

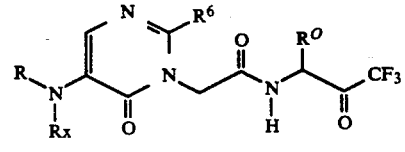

Vb

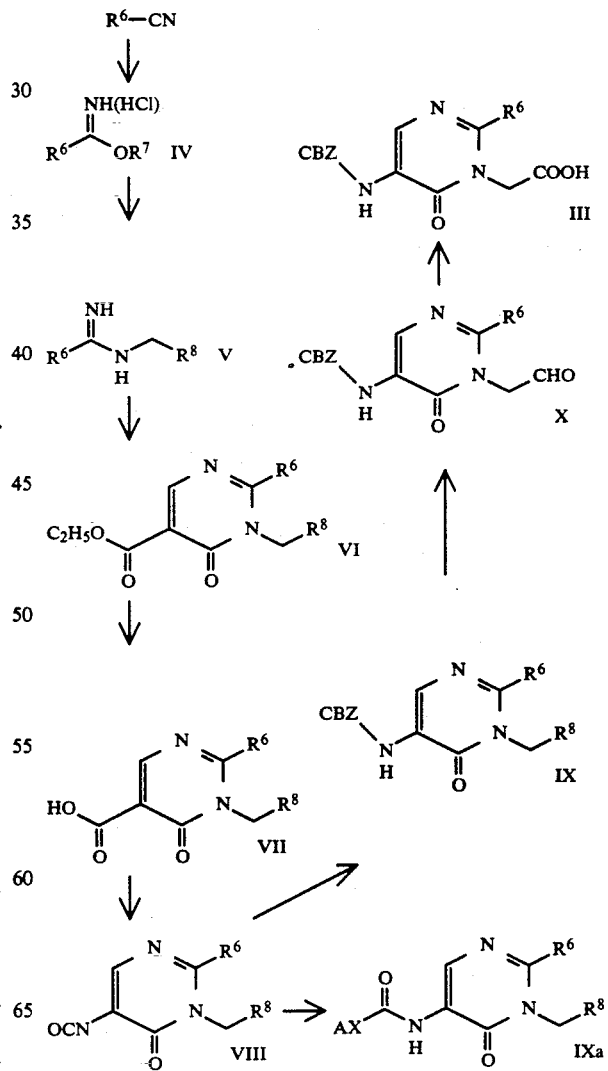

Scheme I

Scheme II

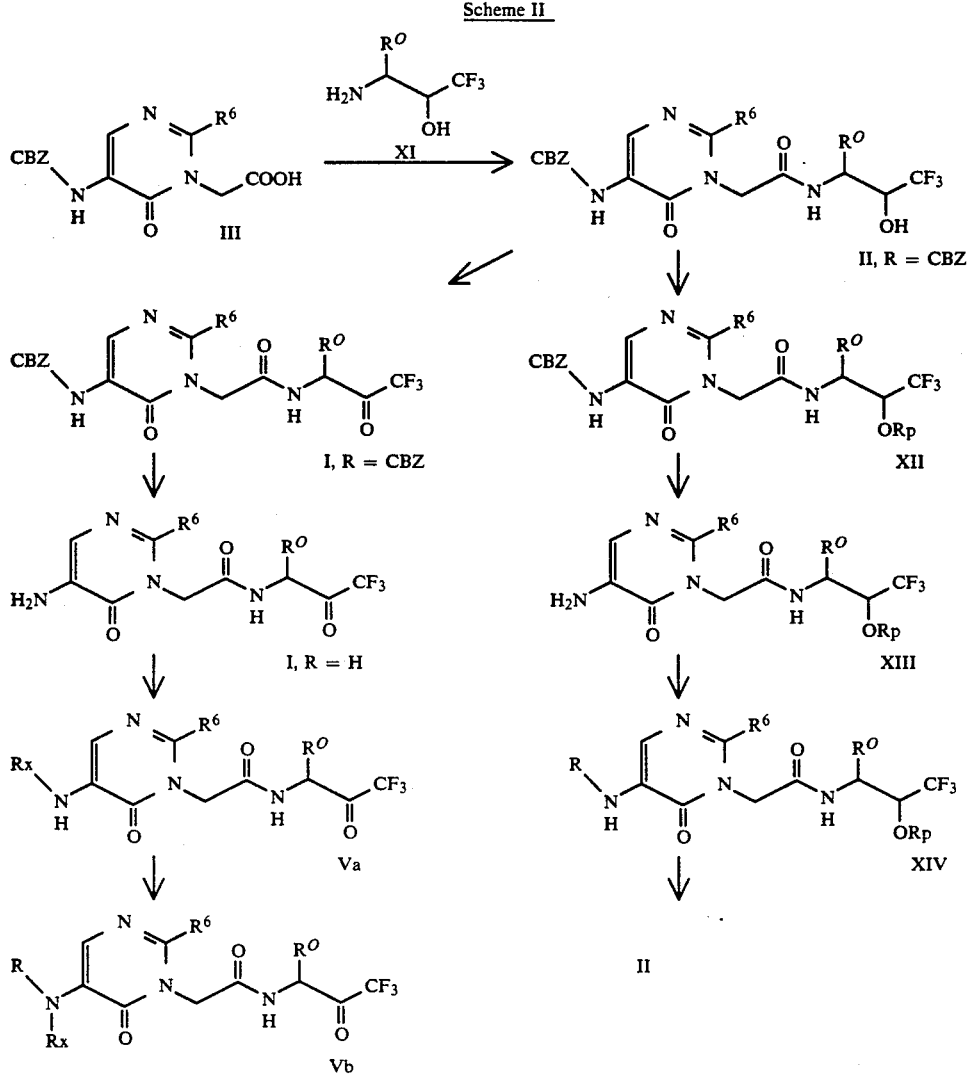

What is claimed is:
1. A compound of formula I

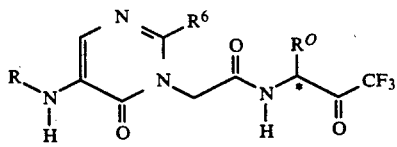

wherein:
$R^0$ is (1-5C)alkyl;
R is hydrogen; or
R is an acyl group of formula A.X.CO— in which
  A.X.—, taken together, is hydrogen, trifluoromethyl, 2,2,2-trifluoroethoxy, amino, methoxyamino, 2,2,2-trifluoroethylamino, RbRcN.O—, RaOCONH—, $R^1SO_2NH$—, RaOCO—, RbRcNVO— or RaCO—; or
R is an acyl group of formula A.X.CJ— in which
J is oxygen or sulfur;
X is a direct bond, imino, oxy or thio; and
A is as defined below or
A is tetrahydropyran-4-yl, 1-methylpiperid-4-yl, or 5-methyl-1,3-dioxacyclohex-5-ylmethyl; or R is a sulfonyl group of formula $D.W.SO_2$— in which
  D.W—, taken together, is hydroxy, amino, di(-lower alkyl)amino, 2,2,2-trifluoroethylamino, 2,2,2-trifluoroethyl, 3,3,3-trifluoropropyl or trifluoromethyl; or
W is a direct bond, imino, carbonylimino, oxycarbonylimino or iminocarbonylimino; and
D is as defined below; or
R is an alkyl, aryl or heteroaryl group G as defined below;
the group A, D or G is (1-6C)alkyl, (3-6C)cycloalkyl, (3-6C)cycloalkyl-(1-3C)alkyl, aryl, aryl(1-3C)alkyl, heteroaryl or heteroaryl(1-3C)alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, CONRbRc, $COO(CH_2)_2$NReRf, cyano, $SO_2R^1$, $CONRdSO_2R^1$, NReRf, NRgCHO, $NRgCOR^2$, $NRgCOOR^2$, NRhCQNRiRj, $NRkSO_2R^3$, $SO_2NRlRm$, $SO_2NRnCOR^4$ and $P(O)(ORa)_2$ in which
Q is oxygen or sulfur;

Ra-Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^1$–$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl; and $R^6$ is (1–5C)alkyl which has no tertiary carbon, (3–7C)cycloalkyl, aryl or heteroaryl, which aryl or heteroaryl independently may bear one or more of the substituents defined for the group A or an aryl or heteroaryl moiety thereof; and provided that no aliphatic carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

2. A compound as claimed in claim 1 wherein:

$R^0$ is methyl, ethyl, propyl, isopropyl or isobutyl;

R is hydrogen, A.X.CO—, A.X.CJ—, D.W.SO$_2$— or G in which

W is a direct bond or imino;

G is (1–3C)alkyl, aryl(1-C)alkyl or heteroaryl(1–2-C)alkyl which may bear one or more substituents as defined in claim 1 for G or a part thereof;

(1–6C)alkyl is methyl, ethyl, propyl, isopropyl, butyl, isobutyl, t-butyl, pentyl, 3-methylbutyl, 1-ethylpropyl, hexyl or 4-methylpentyl; (3–6C)cycloalkyl is cyclopropyl, cyclopentyl or cyclohexyl; the (1–3-C)alkyl portion of (3–6C)cycloalkyl(1–3C)alkyl, aryl(1–3C)alkyl or heteroaryl(1–3C)alkyl is methylene, ethylene or trimethylene; aryl is phenyl, indenyl or naphthyl; heteroaryl is furyl, imidazolyl, tetrazolyl, pyridyl (or its N-oxide), thienyl, pyrimidinyl (or its N-oxide), indolyl or quinolinyl (or its N-oxide); lower alkyl is methyl, ethyl, propyl, isopropyl, butyl, isobutyl or t-butyl; lower acyloxy is acetoxy; lower alkoxy is methoxy, ethoxy, propoxy, isoproxy or t-butoxy; halogeno is bromo, chloro or fluoro; A.X—, taken together, is 2,2,2-trifluoroethoxy; COORa is carboxy or methoxycarbonyl; CONRbRc is carbamoyl or N,N-dimethylcarbamoyl; NRgCOR$^2$ is trifluoroacetylamino; CONRdSO$_2$R$^1$ is N-phenylsulfonylcarbamoyl or N-(4-chlorophenylsulfonyl)carbamoyl; A.X— is tris(hydroxymethyl)methylamino, tris(acetoxymethyl)methylamino or 2,2-bis(hydroxymethyl)propoxy; D.W—, taken together, is 2,2,2-trifluoroethylamino or 3,3,3-trifluoropropyl; and $R^6$ is isopropyl, cyclopentyl, cyclohexyl, phenyl, furyl, thienyl or pyridyl in which a phenyl or heteroaryl may bear one or two substituents as defined in claim 1.

3. A compound as claimed in claim 2 wherein $R^0$ is isopropyl; R is hydrogen, A.X.CO—, A.X.CJ—, D.W.SO$_2$— or G in which A.X—, taken together, is 2,2,2-trifluoroethoxy; J is oxygen; X is a direct bond, imino or oxy; A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl; D.W—, taken together, is 2,2,2-trifluoroethylamino or 3,3,3-trifluoropropyl; D is methyl, ethyl, isopropyl, tert-butyl, cyclohexyl, phenyl, benzyl, phenethyl, pyridyl, thienyl, 5-tetrazolyl, thiazolyl, quinolinyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonylamino, amino, dimethylamino, oxazolidin-2-on-3-yl, acetylamino, trifluoroacetylamino, ureido, methylsulfonyl, sulfamoyl, dimethylphosphoryl or diethylphosphoryl; G is methyl, ethyl, benzyl, phenethyl, pyridyl, pyridylmethyl, thenyl, 5-tetrazolylmethyl, or 2-(pyridyl)ethyl, wherein an alkyl carbon may bear an oxo group and wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

4. A compound as claimed in claim 1, 2 or 3 wherein R is hydrogen, formyl, trifluoroacetyl, 2,2,2-trifluoroethoxycarbonyl, hydroxyoxalyl, methoxycarbonyl, ethoxycarbonyl, isopropoxycarbonyl, 2-methoxyethoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, methylthiocarbonyl, sulfo, aminosulfonyl, dimethylaminosulfonyl, 2,2,2-trifluoroethylaminosulfonyl, 3,3,3-trifluoroethylsulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, formylamino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolinylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

5. A compound as claimed in claim 4 wherein R is hydrogen, formyl, trifluoroacetyl, 2,2,2-trifluoroethoxycarbonyl, methoxycarbonyl, ethoxycarbonyl, isopropoxycarbonyl, 2-methoxyethoxycarbonyl, 4-bromophenoxycarbonyl, benzyloxycarbonyl, 2,6-dimethylpyrid-4-ylmethoxycarbonyl, methylthiocarbonyl, tert-butylaminosulfonyl, 4-acetylaminophenylsulfonyl, 4-{N-(4-chlorophenylsulfonyl)carbamoyl}phenylsulfonyl, benzylsulfonyl, benzylaminosulfonyl or ethyl.

6. A compound as claimed in any one of claims 1–3 wherein $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents.

7. A compound as claimed in claim 1 wherein $R^0$ is methyl, ethyl, propyl, isopropyl or isobutyl; R is hydrogen, formyl, trifluoroacetyl, 2,2,2-trifluoroethoxycarbonyl, hydroxyoxalyl, methoxycarbonyl, ethoxycarbonyl, isopropoxycarbonyl, 2-methoxyethoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, methylthiocarbonyl, sulfo, aminosulfonyl, dimethylaminosulfonyl, 2,2,2-trifluoroethylaminosulfonyl, 3,3,3-trifluoroethylsulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, formylamino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolinylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl; and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents.

8. A compound as claimed in claim 7 wherein $R^0$ is isopropyl; and R is hydrogen, formyl, trifluoroacetyl, 2,2,2-trifluoroethoxycarbonyl, methoxycarbonyl, ethoxycarbonyl, isopropoxycarbonyl, 2-methoxyethoxycarbonyl, 4-bromophenoxycarbonyl, benzyloxycarbonyl, 2,6-dimethylpyrid-4-ylmethoxycarbonyl, methylthiocarbonyl, tert-butylaminosulfonyl, 4-acetylaminophenylsulfonyl, 4-{N-(4-chlorophenylsulfonyl)carbamoyl}phenylsulfonyl, benzylsulfonyl, benzylaminosulfonyl or ethyl.

9. A compound as claimed in claim 1 in which $R^0$ is isopropyl; R is hydrogen, formyl, 2,2,2-trifluoroethoxycarbonyl, isopropoxycarbonyl, methylthiocarbonyl or ethyl; and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents.

10. A compound as claimed in any one of claims 7–9 wherein $R^6$ is phenyl, 4-fluorophenyl or 2-thienyl.

11. A compound as claimed in claim 1 selected from the group consisting of:
(a) 2-[5-amino-6-oxo-2-(2-thienyl)-1,6-dihydro-1-pyrimidinyl]-N-(3,3,3-trifluoro-1-isopropyl-2-oxopropyl)acetamide,
(b) 2-[5-amino-2-(4-fluorophenyl)-6-oxo-1,6-dihydro-1-pyrimidinyl]-N-(3,3,3-trifluoro-1-isopropyl-2-oxopropyl)acetamide,
(c) 2-[5-isopropoxycarbonylamino-6-oxo-2-(2-thienyl)-1,6-dihydro-1-pyrimidinyl]-N-(3,3,3-trifluoro-1-isopropyl-2-oxopropyl)-acetamide,
(d) 2-[5-ethylamino-6-oxo-2-(2-thienyl)-1,6-dihydro-1-pyrimidinyl]-N-(3,3,3-trifluoro-1-isopropyl-2-oxopropyl)acetamide,
(e) 2-[6-oxo-2-phenyl-5-(2,2,2-trifluoroethoxycarbonylamino)-1,6-dihydro-1-pyrimidinyl]-N-(3,3,3-trifluoro-1-isopropyl-2-oxopropyl)acetamide,
(f) 2-(5-methylthiocarbonylamino-6-oxo-2-phenyl-1,6-dihydro-1-pyrimidinyl)-N-(3,3,3-trifluoro-1-isopropyl-2-oxopropyl)acetamide,
(g) 2-[2-(4-fluorophenyl)-5-methylthiocarbonylamino-6-oxo-1,2-dihydro-1-pyrimidinyl]-N-(3,3,3-trifluoro-1-isopropyl-2-oxopropyl)acetamide,
(h) 2-[6-oxo-2-(2-thienyl)-5-(2,2,2-trifluoroethoxycarbonylamino)-1,6-dihydro-1-pyrimidinyl]-N-(3,3,3-trifluoro-1-isopropyl-2-oxopropyl)acetamide,
(i) 2-[5-formylamino-6-oxo-2-(2-thienyl)-1,6-dihydro-1-pyrimidinyl]-N-(3,3,3-trifluoro-1-isopropyl-2-oxopropyl)acetamide, and
(j) 2-(5-formylamino-6-oxo-2-phenyl-1,6-dihydro-1-pyrimidinyl)-N-(3,3,3-trifluoro-1-isopropyl-2-oxopropyl)acetamide.

12. A salt as claimed in claim 1 selected from
(a) for an acidic compound of formula I, an alkalai metal salt, an alkaline earth metal salt, an aluminum salt, an ammonium salt, or a salt made from an organic base which affords a pharmaceutically acceptable cation; and
(b) for a basic compound of formula I, an acid-addition salt made with an acid which provides a pharmaceutically acceptable anion.

13. A compound of formula II,

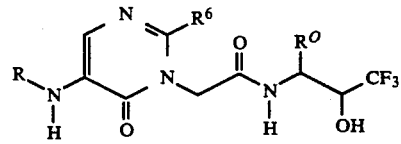

wherein R, $R^0$ and $R^6$ are defined as in claim 1, or a salt thereof.

14. A compound of formula Vb,

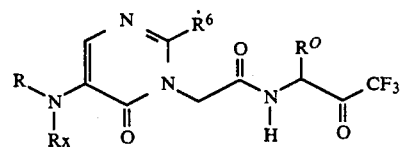

wherein R has a value defined for G in claim 1, $R^0$ and $R^6$ are defined as in claim 1, and Rx is a group which protects and activates a primary amino group for substitution, or a salt thereof.

15. A pharmaceutical composition comprising a human leukocyte elastase inhibiting amount of a compound as defined in claim 1, or a pharmaceutically acceptable salt thereof, and a pharmaceutically diluent or carrier.

16. A method of administering a compound of claim 1, or a pharmaceutically acceptable salt thereof, to a human is need thereof for treatment of a disease or condition in which human leukocyte elastase is implicated.

* * * * *

UNITED STATES PATENT AND TRADEMARK OFFICE
CERTIFICATE OF CORRECTION

PATENT NO. : 5,254,558

DATED : Oct. 19, 1993

INVENTOR(S) : BERNSTEIN ET AL.

It is certified that error appears in the above-identified patent and that said Letters Patent is hereby corrected as shown below:

<u>IN THE CLAIMS</u>:

Column 71, Line 62, "RbRcNVO" should read --RbRcNCO--.

Signed and Sealed this

Fifth Day of July, 1994

Attest:

BRUCE LEHMAN

*Attesting Officer*    *Commissioner of Patents and Trademarks*